(12) United States Patent
Lee et al.

(10) Patent No.: US 12,109,253 B2
(45) Date of Patent: Oct. 8, 2024

(54) USE OF IGFBP7 FOR TREATING MALARIA

(71) Applicant: AGENCY FOR SCIENCE, TECHNOLOGY AND RESEARCH, Singapore (SG)

(72) Inventors: Wenn-Chyau Lee, Singapore (SG); Laurent Renia, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 586 days.

(21) Appl. No.: 17/426,756

(22) PCT Filed: Jan. 30, 2020

(86) PCT No.: PCT/SG2020/050043
§ 371 (c)(1),
(2) Date: Jul. 29, 2021

(87) PCT Pub. No.: WO2020/159444
PCT Pub. Date: Aug. 6, 2020

(65) Prior Publication Data
US 2022/0096604 A1    Mar. 31, 2022

(30) Foreign Application Priority Data
Jan. 30, 2019 (SG) .......................... 10201900872X

(51) Int. Cl.
| | | |
|---|---|---|
| *A61K 38/36* | (2006.01) | |
| *A61K 31/137* | (2006.01) | |
| *A61K 31/155* | (2006.01) | |
| *A61K 31/357* | (2006.01) | |
| *A61K 31/366* | (2006.01) | |
| *A61K 31/4706* | (2006.01) | |
| *A61K 31/4709* | (2006.01) | |
| *A61K 31/506* | (2006.01) | |
| *A61K 31/635* | (2006.01) | |
| *A61K 31/65* | (2006.01) | |
| *A61K 38/18* | (2006.01) | |
| *A61P 33/06* | (2006.01) | |

(52) U.S. Cl.
CPC ............ *A61K 38/36* (2013.01); *A61K 31/137* (2013.01); *A61K 31/155* (2013.01); *A61K 31/357* (2013.01); *A61K 31/366* (2013.01); *A61K 31/4706* (2013.01); *A61K 31/4709* (2013.01); *A61K 31/506* (2013.01); *A61K 31/635* (2013.01); *A61K 31/65* (2013.01); *A61K 38/18* (2013.01); *A61P 33/06* (2018.01)

(58) Field of Classification Search
None
See application file for complete search history.

(56) References Cited

U.S. PATENT DOCUMENTS

| 9,592,271 B2 | 3/2017 | Purcell Ngambo et al. |
|---|---|---|
| 2018/0127752 A1 | 5/2018 | Liu et al. |

FOREIGN PATENT DOCUMENTS

| WO | 2009/036188 A2 | 3/2009 |
|---|---|---|
| WO | 2009/099378 A1 | 8/2009 |
| WO | 2010/113146 A1 | 10/2010 |

OTHER PUBLICATIONS

Extended European Search Report mailed Jul. 13, 2022 for EP Patent Application No. 20747994.0, Applicant: Agency for Science, Technology and Research; Reference No. SJM/P132219EP (7 pages).
Singapore Written Opinion mailed Jul. 7, 2022 for SG11202108022R filed Jan. 30, 2020, Examiner's Reference No. IPOS/FYL; (6 pages).
Rosauro Varo et al: "Adjunctive therapy for severe malaria: a review and critical appraisal", Malaria Journal, vol. 17, No. 1, Jan. 24, 2018, XP055574350, DOI: 10.1186/s12936-018-2195-7.
Mats Wahlgren et al: "Variant surface antigens of Plasmodium falciparum and their roles in severe malaria", Nature Reviews Microbiology, vol. 15, No. 8, Jun. 12, 2017, pp. 479-491, XP055615272, GB ISSN: 1740-1526, DOI: 10.1038/nrmicro.2017.47.
Communication (International Search Report) issued by the International Searching Authority in International Application No. PCT/SG2020/050043 dated Jun. 4, 2020, 4 pages total.
Communication (Written Opinion) issued by the International Searching Authority in International Application No. PCT/SG2020/050043 dated Jun. 4, 2020, 5 pages total.
Havlik, I. et al., "Curdlan Sulphate in Human Severe/Cerebral Plasmodium Falciparum Malaria," Transactions of the Royal Society of Tropical Medicine and Hygiene (2005) vol. 99, pp. 333-340.

*Primary Examiner* — Christina Bradley
(74) *Attorney, Agent, or Firm* — Troutman Pepper Hamilton Sanders LLP

(57) ABSTRACT

The invention relates to a composition comprising insulin growth factor binding protein 7 (IGFBP7) for treating malaria or reducing the phenomenon of IRB C-endothelial cytoadherence. The composition can further comprise Von Willebrand Factor (VWF) and/or thrombospondin-1 (TSP-1). The composition can also be used as an adjunct therapeutic agent alongside other anti-malarial drugs.

14 Claims, 43 Drawing Sheets

Figure 1A:
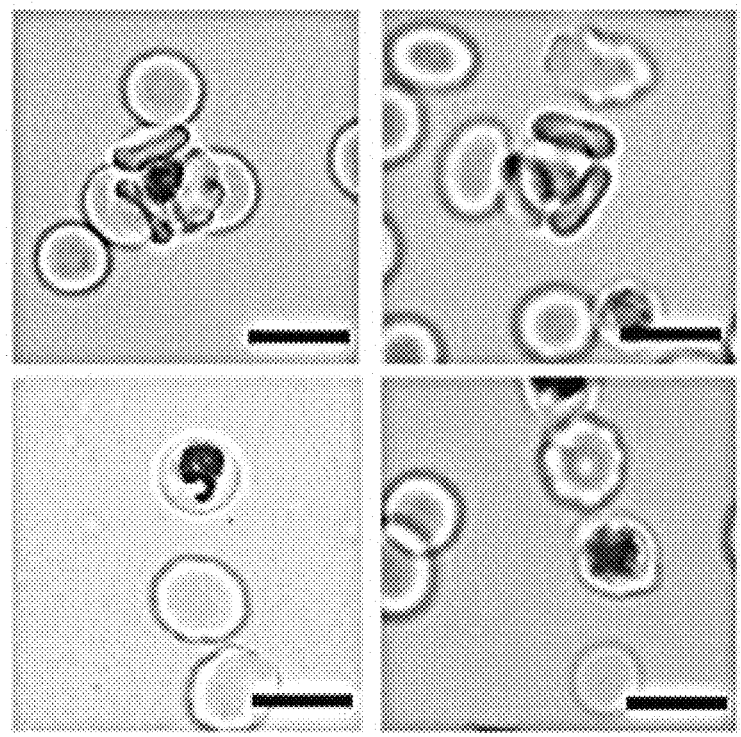

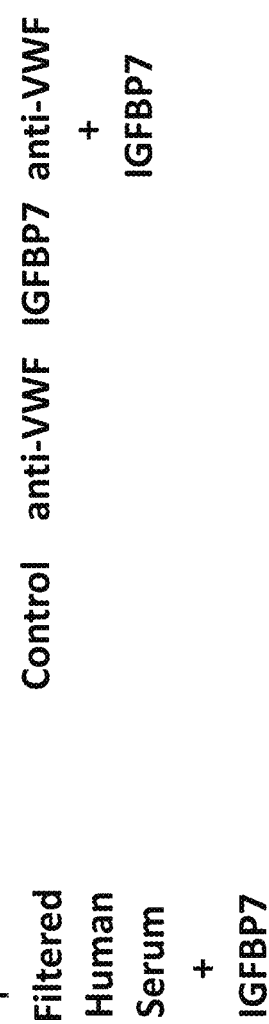
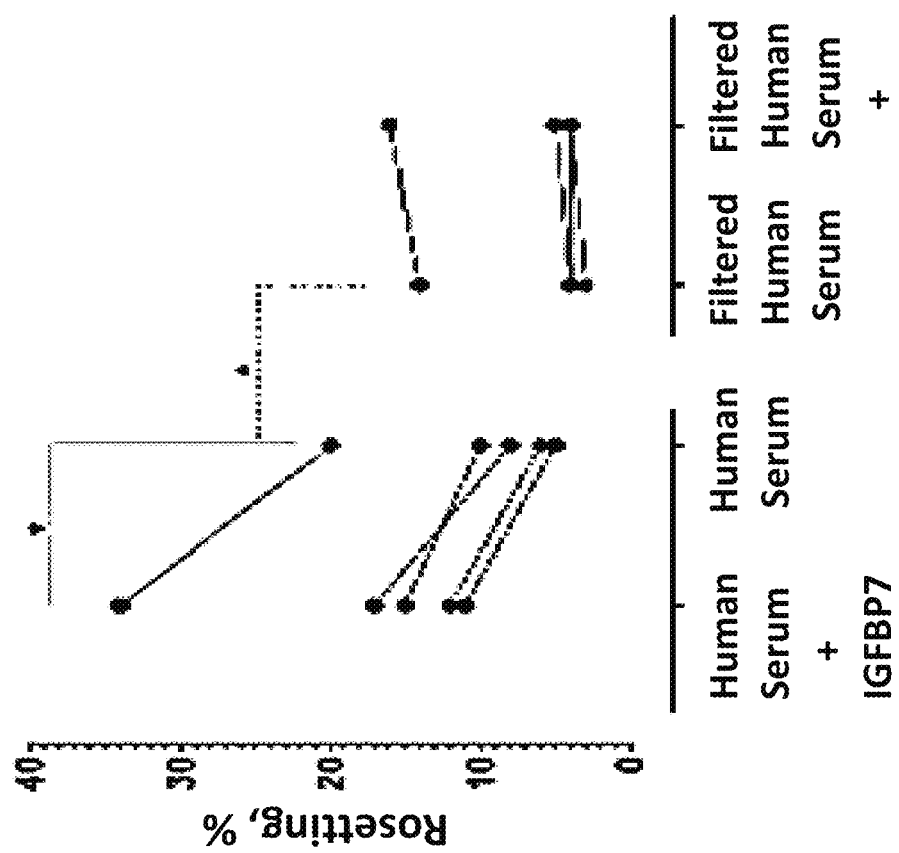
Figure 7A
Figure 7B

USE OF IGFBP7 FOR TREATING MALARIA

CROSS-REFERENCE TO RELATED APPLICATIONS

This application is a U.S. National Phase application under 35 U.S.C. § 371 of International Patent Application No. PCT/SG2020/050043, filed on Jan. 30, 2020, which claims priority to Singapore Patent Application No. 10201900872X, filed on Jan. 30, 2019, both of which applications are incorporated herein by reference in their entireties.

The present invention relates to a protein that is useful for treating malaria.

The listing or discussion of an apparently prior-published document in this specification should not necessarily be taken as an acknowledgement that the document is part of the state of the art or is common general knowledge.

Any document referred to herein is hereby incorporated by reference in its entirety.

Malaria is an infectious parasitic disease transmitted by mosquitoes. It is characterized by periodic fever and an enlarged spleen. Malaria affects some 200 million people a year. Malaria in humans is caused by 6 species of parasitic protozoa belonging to the genus Plasmodium (P. falciparum, P. vivax, P. malariae, P. ovale, P. knowlesi, P. cynomolgi). Of these, P. falciparum is the most fatal cause of malaria.

Malaria is transmitted by infected female Anopheline mosquitoes. The Plasmodia sporozoites develop and mature in the insect, and is then transferred when the mosquito bites a human. Inside the human, the parasite settles first in the liver, multiplies and then invades the red blood cells. This is when the symptoms of malaria become evident.

Despite numerous attempts at eradication, malaria remains a serious endemic disease in many areas of Africa, Latin America and Oceania, with a worldwide mortality rate of approximately 1 million per year (WHO Scientific Group on the Chemotherapy of Malaria 1990). One of the major factors contributing to the continued presence of malaria is the emergence of malaria parasites that are resistant to one or more anti-malarial compounds.

Along its intraerythrocytic development, Plasmodium spp. modifies the infected erythrocyte (IRBC) rheology (increased rigidity for P. falciparum IRBC, reduced rigidity but increased fragility for P. vivax IRBC). Such alteration increases the susceptibility of IRBC to splenic clearance. However, the parasites have developed escape strategies to avoid splenic elimination. For instance, P. falciparum expresses adhesins on the IRBC that mediate adhesion to the endothelial cells, resulting in deep microvasculature sequestration. This triggers endothelial activation, which leads to vascular injury that forms the basis of severe malaria pathology. Additionally, an IRBC can bind directly to uninfected red blood cell (URBC) to form a 'rosette'. This rosetting phenomenon has been described in all human malaria parasites. However, functional importance of rosetting remains ambiguous. Rosetting phenomenon is believed to assist the parasites to sequester in deep microvasculature alongside IRBC-endothelial cytoadherence, where rosette formation can widen the vasculature area coverage that allows the parasites to sequester away from splenic clearance. Rosetting and IRBC-endothelial cytoadherence happen with the same parasite-derived ligand such as PfEMP1. The dynamics between rosetting and IRBC-endothelial cytoadherence is not well studied. However, it has been shown that the pre-formed rosettes hamper IRBCs from cytoadhering to endothelial cells (the very biological event that leads to endothelial activation and inflammation). While the supposed role of rosetting in the facilitation of merozoite invasion of URBC is unlikely; recent studies show that rosette formation may have a role in parasite immune-evasion. Theoretically, the masking of rosetting IRBC with URBC may hamper IRBC recognition and therefore their clearance by the host immune system11. Notably, rosetting has been associated (in some but not all studies) with disease severity13-18. Here, we observed that the addition of leukocytes increased the rosetting rates of various P. falciparum and P. vivax isolates. We next demonstrated that IRBC stimulated monocytes to secrete products capable of stimulating rosetting, the most important being insulin growth factor binding protein 7 (IGFBP7). We further showed that IGFBP7-mediated rosetting was different from the previously described rosetting (defined here as type I rosetting), where it (we referred to as type II rosetting) required additional serum factors to occur, in addition to the interaction between the parasite-derived ligand on IRBC surface and the receptor on the surface of URBC. Functionally, we observed that the IGFBP7-mediated type II rosetting reduced phagocytosis by monocytes, and therefore defined a new escape mechanism for the malaria parasites. Despite the role that seems to enhance the survival of parasites within the host, rosetting event, which can be promoted by the host-derived IGFBP7, can also reduce and prevent the phenomenon of IRBC-endothelial cytoadherence. This may prevent or reduce the endothelial activation, hence the vascular injury. Thus, the potentially fatal malaria-induced complications may be minimised or reversed by this host-derived proteins. The property of this protein may confer survival benefit to both the host and parasite in this parasitism relationship with long evolutionary history.

In a first aspect of the invention, there is provided a protein that is useful for reversing or relieving the vasculature pathology caused by IRBC-endothelial cytoadherence in individuals afflicted with malaria. In particular, in an embodiment of the invention, the protein is IGFBP7 and any compositions comprising IGFBP7 for use for treating individual afflicted with malaria.

More particularly, in various aspects of the invention, there is provided the use of a composition comprising IGFBP7 for use as an adjunct therapeutic agent as part of an overall strategy or regime for treating individuals afflicted with malaria alongside the administration of other potent anti-malarial drugs to kill the malaria parasites by reversing or relieving the vasculature pathology caused by IRBC-endothelial cytoadherence. By using this as an "adjunct treatment" we mean to use it to relief, reduce, reverse or even prevent the severe vasculature pathology within the patient's vasculature while the parasites are killed by the potent anti-malarial agents.

In various embodiments, the composition further comprises a Von Willebrand Factor (VWF) and/or a thrombospondin-1 (TSP-1). The amount of IGFBP7 in the composition is about at least 100 ng/ml. The amounts of VWF and TSP-1 present in the composition may be about between 0.125 to 0.5 IU/ml, and about 10 ng/ml respectively, which are within the physiologic concentration range for humans. If an individual's blood test shows abnormally low levels of VWF and TSP-1, then VWF and TSP-1 may be administered to said individual.

In various embodiments, the IGFBP7 in the composition is in an admixture with one or more other anti-malarial drugs. The anti-malarial drugs are selected from the group comprising artemether/artesunate, chloroquine, mefloquine, pyrimethamine, sulfadoxine, amodiaquine, quinine/quinidine, halofantrine, tovaquone, proguanil and doxycycline In another aspect of the invention, the composition can be used for treatment, e.g. as a pharmaceutical. In use, VWF, TSP-1 and IGFBP7 may be combined as the active ingredient in intimate admixture with a pharmaceutical carrier according to conventional pharmaceutical compounding techniques. In various embodiments, such pharmaceutical compositions may be useful to treat vascular-related inflammatory disorder. The carrier may take a wide variety of forms depending on the form of preparation desired for administration, e.g. oral or parenteral (e.g. intravenous). In preparing the compositions for oral dosage form, any of the usual pharmaceutical media may be employed as carriers, such as, for example, water, glycols, oils, alcohols, flavouring agents, preservatives, colouring agents, and the like in the case of oral liquid preparations (such as suspensions, solutions and elixirs) or aerosols; or carriers such as starches, sugars, micro-crystalline cellulose, diluents, granulating agents, lubricants, binders, disintegrating agents, and the like may be used in the case of oral solid preparations such as, for example, powders, capsules, and tablets, with the solid oral preparations being preferred over the liquid preparations. The most preferred solid oral preparation is tablets.

Because of their ease of administration, tablets and capsules represent the most advantageous oral dosage unit form in which case solid pharmaceutical carriers are employed. If desired, tablets may be coated by standard aqueous or non-aqueous techniques.

In addition to the common dosage forms set out above, the composition of the present invention may also be administered by controlled release means and/or delivery devices such as those described in U.S. Pat. Nos. 3,845,770; 3,916,899; 3,536,809; 3,598,123; 3,630,200; 4,008,719; 4,687,660; and 4,769,027.

Pharmaceutical compositions employed in the present invention suitable for oral administration may be presented as discrete units such as capsules, cachets, or tablets, or aerosol sprays each containing a predetermined amount of the active ingredient as a powder or granules, a solution or a suspension in an aqueous liquid, an oil-in-water emulsion, or a water-in-oil liquid emulsion. Such compositions may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or moulding, optionally with one or more accessory ingredients. Compressed tablets may be prepared by compressing in a suitable machine the active ingredient in a free-flowing form such as powder or granules, optionally mixed with a binder, a lubricant, an inert diluent, and/or a surface active or dispersing agent. Moulded tablets may be made by moulding in a suitable machine a mixture of the powdered compound moistened with an inert liquid diluent.

In addition, or alternatively, the compositions of the invention may also be administered parenterally, for example, intravenously, intra-articularly, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and nonaqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind known in the art.

In another aspect of the invention, there is provided a method of treating an individual afflicted with malaria comprising administering to the individual in need of such treatment an effective amount of a medicament containing IGFBP7.

In order that the present invention may be fully understood and readily put into practical effect, there shall now be described by way of non-limitative examples only preferred embodiments of the present invention, the description being with reference to the accompanying illustrative figures.

In the figures:

FIG. 1. Deciphering leukocyte subpopulation that influences rosetting. (A) Rosette (above) and non-rosetting (bottom) IRBC in culture medium for respective species. Scale bars represent 10 μm; oil immersion (1000×) magnification. Pictures taken with microscope camera Olympus DP21 on light microscope Olympus BX43. (B) Effect of autologous leukocytes on rosetting [$P.$ $falciparum$ (Pf, n=3) (paired t-test P=0.0115) and $P.$ $vivax$ (Pv, n=14) (paired t-test P<0.0001)]. (C) Comparison of effects of monocytes and neutrophils from different healthy individuals (n=3) on Pf (n=4) rosetting, Friedman test with Dunn's multiple comparison test P=0.0003 for comparison between control and monocytes; P=0.7422 between control and neutrophils. (D) Rosetting rates of lab-adapted Pf lines under different experimental conditions (co-incubated with 1×105 purified CD14+ peripheral monocytes and CD14− PBMC fractions from two healthy individuals, 1×105 THP-1s, and control without co-incubation with WBCs). Means and S.D. of triplicate (three biological replicates) experiments shown. Two-way ANOVA with Tukey's multiple comparison test: adjusted P<0.0001 in control vs. both CD14+ and control vs. THP-1 for all parasite lines. No significant difference found in THP-1 vs. CD14+ (P>0.5 for all parasite lines), and control vs. CD14− (P>0.5 for all parasite lines). (E) Plot showing changes of rosetting rates of three laboratory adapted $P.$ $falciparum$ lines when incubated with different numbers of UT and MT separately. Means and S.D. of triplicate experiments shown. (F) Rosetting of lab-adapted Pf lines under different experiment conditions [control, with UT, MT, and with culture supernatant of UT (CSUT) and MT (CSMT)]. One way ANOVA with Tukey's multiple comparison test: control vs. UT: P=0.0072; control vs. MT: P<0.0001; control vs. CSUT: P=0.0293; control vs. CSMT: P<0.0001; control vs. IFNγ: P>0.9999; UT vs. CSUT:

P=0.1411; MT vs. CSMT: P=0.1397. UT vs. CSMT: P=0.033; df=3. *P<0.05, P<0.01, *P<0.001, ****P<0.0001.

FIG. 2. Characterization of the secreted rosette-stimulating factors. (A) Rosetting of clinical isolates (Pf: n=11, Pv: n=9) post-incubation with whole CSMT (paired t-test Pf: P=0.0001; Pv: P=0.0017) and its aqueous (Pf: P<0.0001; Pv: P=0.0002) and lipid (Pf: P=0.0954; Pv: P=0.0905) fractions. (B, C) Pf (n=9) and Pv (n=22) rosetting post-incubated with CMST aqueous fraction of different sizes. From One way ANOVA with Tukey's test, both smaller-size (Pf: P<0.0001; Pv: P<0.0001) and larger-size (Pf: P=0.0007; Pv: P<0.0001) fractions significantly stimulated rosetting, with the smaller-size fraction exerted higher rosette-stimulation than the larger-size fraction (Pf: P=0.0005; Pv: P<0.0001). (D) Effect of heating on rosette-stimulation by the CMST aqueous 30 kDa fraction. Experiment was conducted with laboratory-adapted P. falciparum (n=4). One way ANOVA with Tukey's test: the unheated (P<0.0001) and heat-denatured (A) fractions (P=0.0236) stimulated rosetting, with the unheated fraction exerted higher stimulation than the heated fraction (P=0.0009). *P<0.05, P<0.01, *P<0.001, ****P<0.0001.

Figure 3:
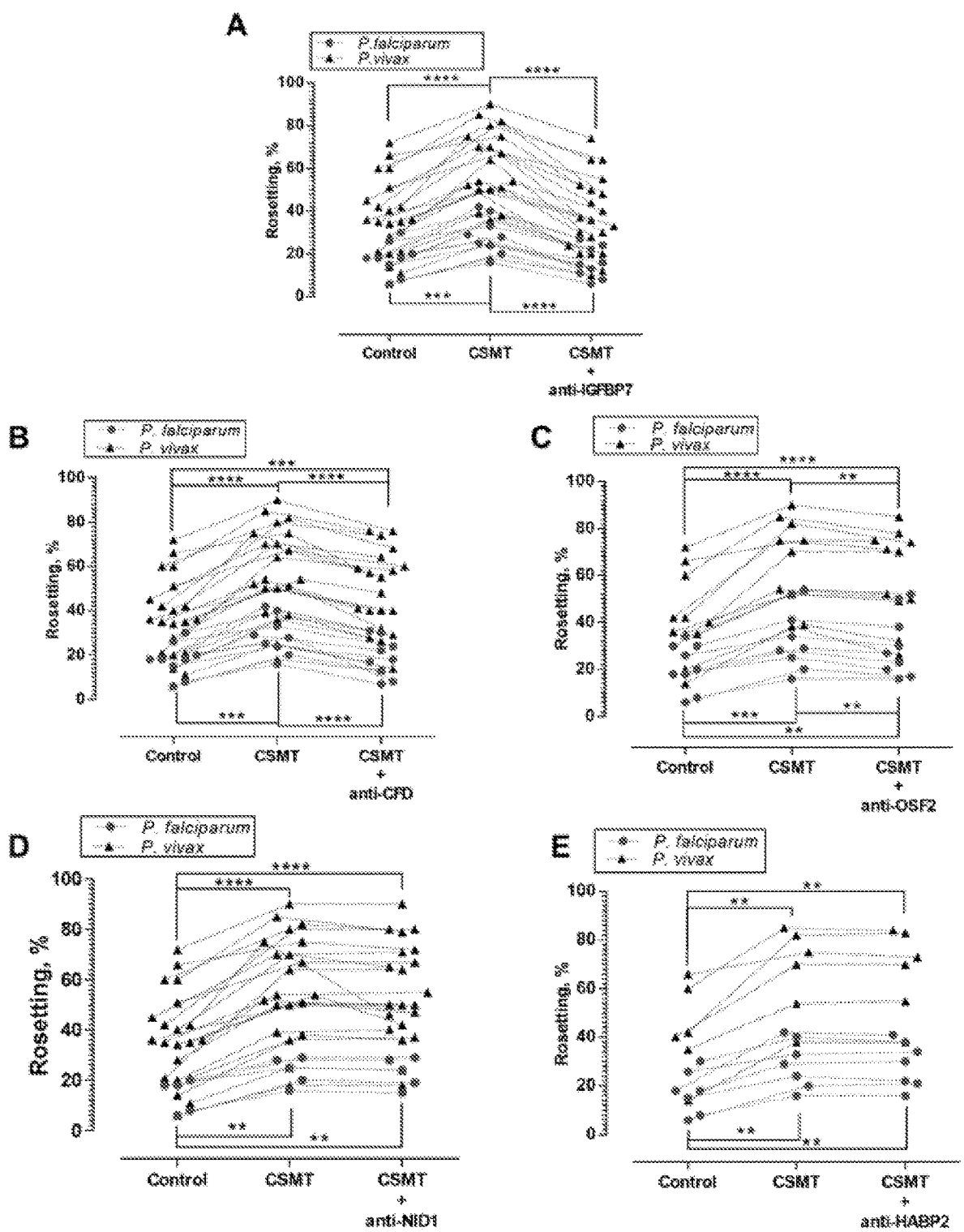

FIG. 3. Antibody blocking assay. One-way ANOVA with Tukey's test was conducted to compare the rosetting rates between the control, CSMT and CSMT+antibodies against proteins of interest. (A) Rosetting rates were significantly increased by CSMT [Pf (n=9): P=0.0008; Pv (n=21): P<0.0001]. Anti-IGFBP7 significantly reduced the CSMT-mediated rosette-stimulation [Pf: P<0.0001; Pv: P<0.0001]. No significant difference found between the control and CSMT+anti-IGFBP7 groups [Pf: P=0.5498; Pv: P=0.8724]. (B) Significant rosette-stimulation was found between control and CSMT [Pf (n=9): P=0.0008; Pv (n=21): P<0.0001]. Anti-CFD significantly reduced CSMT-mediated rosette-stimulation [Pf: P=0.0003; Pv: P<0.0001]. Significant difference detected between control and CSMT+anti-CFD groups for Pv (P=0.0002), but not in Pf (P=0.8494). (C) Rosetting rates were significantly increased by CSMT [Pf (n=9): P=0.0004; Pv (n=11): P<0.0001]. Anti-OSF2 significantly reduced the CSMT-mediated rosette-stimulation [Pf: P=0.0017; Pv: P=0.0038]. Significant difference detected between control and CSMT+anti-OSF2 groups for Pf (P=0.0058) and Pv (P<0.0001). (D) Rosetting rates were significantly increased by CSMT [Pf (n=5): P=0.0038; Pv (n=21): P<0.0001]. Anti-NID1 did not significantly alter CSMT-mediated rosette-stimulation [Pf: P=0.1432; Pv: P=0.1369]. Significant difference found between control and CSMT+anti-NID1[Pf: P=0.0051; Pv: P<0.0001]. (E) Rosetting rates were significantly increased by CSMT [Pf (n=7): P=0.0040; Pv (n=6): P=0.0051]. Anti-HABP2 did not significantly alter CSMT-mediated rosette-stimulation [Pf: P=0.8514; Pv: P=0.9358]. Significant difference found between control and CSMT+anti-HABP2 [Pf: P=0.0045; Pv: P=0.0073]. Of note, anti-human NID1 IgG was of the same subclass and raised in the same animal species as the antibodies used against IGFBP7, CFD and OSF2. Hence, it also acted as a negative control in this set of experiment (see Table 6).*P<0.05, P<0.01, *P<0.001, ****P<0.0001.

FIG. 4. Characterization of IGFBP7-mediated rosetting. (A, B) Rosetting rates post-rhIGFBP7-incubation. Significant rosette-stimulation noted at 50 ng/ml rhIGFBP7 (One-way ANOVA with Dunnett's test: Pf (n=7): P=0.0224; Pv (n=7): P=0.0419) and attain plateau after 100 ng/ml (Pf: P=0.0045; Pv: P=0.0168). (C, D) Comparison of rosette-stimulatory effects between the CSMT and rhIGFBP7 in P. falciparum (n=5) (One way ANOVA with Tukey's test: control vs. CMST: P=0.0019; control vs. rhIGFBP7: P=0.0054; CMST vs. rhIGFBP7: P=0.6866) (C) and P. vivax (n=11) (One way ANOVA with Tukey's test: control vs. CMST: P<0.0001; control vs. rhIGFBP7: P=0.0039; CMST: P<0.0001; control vs. rhIGFBP7: P=0.0108) (D). (E, F) Impact of heat denaturation on rosette-stimulatory effect of rhIGFBP7 in P. falciparum (n=5) (E) (One way ANOVA with Tukey's test: control vs. rhIGFBP7: P=0.0036; control vs. ΔrhIGFBP7: P=0.9721; rhIGFBP7 vs. ΔrhIGFBP7: P=0.0048) and P. vivax (n=4) (F) (One way ANOVA with Tukey's test: control vs. rhIGFBP7: P=0.0006; Control vs. ΔrhIGFBP7: P=0.8008; rhIGFBP7 vs. ΔrhIGFBP7: P=0.0004). (G) Changes of lab-adapted Pf (n=5) rosetting rates following incubation with IGFBP7 up till the 60th minute. One way ANOVA with Dunnett's test: significant increment was detected as fast as the 15th minute (and onwards). P=0.0001. (H) Changes of rosetting rates of lab-adapted Pf (n=5) after IGFBP7-exposure (covered by grey box), followed by removal of IGFBP7 from the system in the span of 60 minutes. One-way ANOVA with Dunnett's test: significant rosetting rate increment was seen after IGFBP7 exposure (P=0.0001). The rosetting rates were still significantly higher than the baseline (control) five minutes (P=0.0001) and 10 minutes (P=0.0265) after IGFBP7-removal. From the 15th to the 60th minute post-IGFBP7 removal, the rosetting rates dropped to levels that were of no significant difference with the baseline values.

FIG. 5. Deciphering rosetting ligands involved in IGFBP7-mediated rosetting. (A) IRBC-trypsin treatments on IGFBP7-mediated rosetting. Dotted lines demonstrate data collected from same isolates. IGFBP7 increased rosetting in the untreated settings (paired t-test Pf (n=5): P=0.0171; Pv (n=4): P=0.0023) but did not significantly alter rosetting in groups treated with 10 µg/ml trypsin (Pf: P=0.3739; Pv: P=0.3910) and 1 mg/ml trypsin (Pf: same values; Pv: P=0.3910). (B) Rosetting rates (mean and S.D. from quintuplicate experiment repeats shown) along rhIGFBP7 concentrations for PfCS2-WT and PfSBP1-KO-CS2. Significant CS2-WT rosette-stimulation was noted from rhIGFBP7 of 100 ng/ml (Friedman with Dunn's test: P=0.0230). No significant changes noted for SBP1-KO-CS2 across the range of IGFBP7 concentrations studied (Friedman with Dunn's test: P>0.9999). (C) Effect of IGFBP7 on rosetting rates of NF54_VAR2CSA_WT and NF54_T934D (mean and S.D. from quintuplicate experiment repeats shown). Mann-Whitney test was conducted. For NF54_VAR2CSA_WT, IGFBP7 significantly increased the rosetting rates (P=0.0079). For NF54_VAR2CSAT934D, IGFBP7 did not cause significant change to the rosetting rates of the parasite (P=0.7619). The rosettes formed by NF54_VAR2CSA_WT (i) and NF54VAR2CSAT934D (ii) are small. (D) Rosetting rates of the late ring forms (means and S.D. of 9 replicates shown) under IGFBP7-free and IGFBP7-supplied conditions. Mann-Whitney test was conducted. Rosetting rates was significantly higher in the IGFBP7-supplied group (P<0.0001). (E) Rosettes formed by the late ring stage (left) and late trophozoite stage (right) of P. falciparum. Scale bar: 10 µm.

FIG. 6. Deciphering rosetting receptors involved in IGFBP7-mediated rosetting. (A) Heparinase (hep) I treatment on U RBC hampered IGFBP7-mediated rosetting. Friedman with Dunn's test: Pf (n=7): untreated vs. hep: P=0.0063; hep vs. hep+IGFBP7: P>0.9999; untreated vs. hep+IGFBP7: P=0.0334. Pv (n=11): untreated vs. hep: P=0.0004; hep vs. hep+IGFBP7: P>0.9999; untreated vs. hep+IGFBP7: P=0.0042. (B) Hep III treatment on U RBC hampered IGFBP7-mediated rosetting. Friedman with Dunn's test Pf (n=7): untreated vs. hep: P=0.0150; hep vs. hep+IGFBP7: P>0.9999; untreated vs. hep+IGFBP7: P=0.0485. Pv (n=11): untreated vs. hep: P=0.0013; hep vs. hep+IGFBP7: P>0.9999; untreated vs. hep+IGFBP7: P=0.0013. (C) Rosette size difference between the untreated (left) and heparinase-treated (right) settings of a *P. vivax* isolate. Rosettes are indicated by green arrow whereas IRBC-autoagglutination-like clustering is indicated by the red arrow. Pictures taken with Samsung Galaxy W phone camera on Nikon Eclipse E200 light microscope. Scale bars represent 10 μm. (D) Anti-CR1 reduced Pf (n=11) rosetting (One way ANOVA with Tukey's test: P<0.0001). With CR1-blockade, IGFBP7 still managed to induced significant rosette-stimulation (P=0.0057), albeit with lower degree than Ab-free setting (P=0.0095). (E) Anti-CR1 did not inhibit Pv (n=5) rosetting [One way ANOVA with Tukey's test: P=0.9947]. IGFBP7 increased rosetting (P<0.0001). No significant difference found between IGFBP7 and anti-CR1+IGFBP7 groups (P=0.9612). Effect of different ABO blood groups on IGFBP7-mediated rosetting for Pf (n=7) (F) and Pv (n=7) (G). Dotted horizontal lines in these plots matched the same isolates used in each of the different ABO blood group experiments. IGFBP7 significantly increase rosetting rates regardless of the blood groups [One way ANOVA with Tukey's test: (Pf: P<0.0001 for all groups); (Pv: P<0.0001 for all groups)]. No significant differences in rosetting rates (control and IGFBP7-supplied) across all blood groups for both species. The degree of rosette stimulation by CSMT on Pf (n=5) (H) and Pv (n=9) (I) with URBC of different ABO blood groups. Dotted lines in these plots matched the same isolates used in each of the different blood group experiments. CSMT increased rosetting regardless of the blood groups [One-way ANOVA with Tukey's test: (Pf: Group O: P=0.0014; Group A: P=0.0018; Group B: P=0.0033; Group AB: P=0.0010); (Pv: P<0.0001 for all blood groups)]. No significant differences in rosetting rates (control and CMST-supplied) across all groups for both species.

FIG. 7. Identification of other serum factors involved in IGFBP7-mediated rosetting using lab-adapted *P. falciparum*. (A) Rosetting rates in filtered human serum (HS) were lower than those of complete HS (One-way ANOVA with Tukey's test: P=0.0368; n=5). IGFBP7 stimulated rosetting in HS-supplied environment (P=0.0276). IGFBP7 did not alter rosetting in filtered HS (P=0.0664). (B) IGFBP7 stimulated rosetting (P=0.0002; n=8), whereas anti-VWF IgG did not significantly alter rosetting (P=0.3039). No significant changes found in "anti-VWF IgG+IGFBP7" (P=0.9096). (C) In 20% HS-enriched medium (20% HSM), "IGFBP7 and IGFBP7+VWF" showed higher rosetting than the control (One way ANOVA with Tukey's test: P=0.003 for both comparisons; n=8). VWF did not alter rosetting (P=0.8652). No significant difference found between "IGFBP7" and "IGFBP7+VWF" (P=0.7853). Rosetting in "IGFBP7" were higher than "VWF" (P<0.0001). In 2% HSM, "IGFBP7" (P=0.1832) and "VWF" (P=0.9876) did not significantly alter rosetting. Rosetting in "IGFBP7+VWF" were increased (P=0.0014), and were higher than "IGFBP7" and "VWF" (P=0.0030 for both comparisons). No significant difference found between "VWF+IGFBP7" from both serum settings (P=0.2861). (D) Rosetting (n=7) in 0.25% Albumax-enriched medium (Alb) supplied with 100 ng/ml IGFBP7 and different concentrations of VWF. No significant difference across the VWF concentrations tested (One way ANOVA with Dunnett's test: P>0.3 for all comparisons with "VWF-free"). (E) In 20% HSM, no significant different between control and "anti-TSP-1" (One way ANOVA with Tukey's test: P=0.9961, n=8). Significant difference was recorded between control and "IGFBP7" (P<0.0001), but not between control and "anti-TSP-1+IGFBP7" (P=0.9125). Significant difference was found in "anti-TSP-1" vs. "IGFBP7" (P<0.0001), and "IGFBP7" vs. "IGFBP7+anti-TSP-1" (P=0.0022). (F) Rosetting (n=8) in Alb were lower than those in 20% HSM (P=0.0047). In HSM, IGFBP7 increased rosetting (P=0.0097). No significant changes from comparisons of Alb-control with: IGFBP7 (P=0.7499), VWF (P>0.9999), TSP-1 10 ng/ml (P>0.9999), TSP-1 500 ng/ml (P=0.9491), IGFBP7+TSP-1 10 ng/ml (P>0.9999), IGFBP7+TSP-1 500 ng/ml (P=0.9341). Rosette-stimulation was noted in "IGFBP7+VWF+TSP-1 10 ng/ml" (P=0.0002) and "IGFBP7+VWF+TSP-1 500 ng/ml" (P<0.0001). No significant difference noted between "IGFBP7+VWF+TSP-1 10 ng/ml" and "IGFBP7+VWF+TSP-1 500 ng/ml" (P=0.9998), and "IGFBP7+VWF+TSP-1 10 ng/ml" vs. "20% HSM+IGFBP7" (P>0.9999). "IGFBP7+VWF+TSP-1 500 ng/ml" were not significantly different from "HSM+IGFBP7" (P=0.9997). (G) In 0.25% Alb supplied with 100 ng/ml IGFBP7, 10 ng/ml TSP-1 and 0.125 IU/ml VWF, rosette-stimulation was noted, as compared to VWF-free group (One way ANOVA with Tukey's test: P=0.0421, n=8). Rosetting increased with VWF concentrations (P<0.0001 for 0.5 and 2.0 IU/ml as compared to VWF-free). No significant difference in rosetting rates between VWF of 0.5 IU/ml and 2.0 IU/ml (P=0.2126).

FIG. 8. IGFBP7 secretion upon parasite exposure and phagocytosis assessment. (A) Parasite (lab-adapted *P. falciparum* strain 3D7) exposure increased IGFBP7 secretions by human peripheral monocytes (from five donors) [paired t-test control vs. IRBC: P<0.0001; URBC vs. IRBC: P<0.0001]. (B) Secretion of IGFBP7 by THP-1 upon exposure to different parasite lines (n=5) at different parasite density. Parasite exposure yielded significantly higher readings than the parasite-free control (One-way ANOVA with Dunnett's test: P=0.0001). (C) IGFBP7 secretion by WT-THP-1 (WT) and IGFBP7-KD-THP1 (KD) exposed to URBC and IRBC for 18 hours. Blue dotted line shows the detection limit. For control groups (incubated with URBC), WT showed significantly higher IGFBP7 secretion than the KD (Mann-Whitney test: P=0.0079, n=5). For the IRBC-exposed groups, WT also showed significantly higher IGFBP7 secretion than the KD (P=0.0079, n=5). IGFBP7 secretion by WT post-IRBC exposure was significantly higher than its control (P=0.0079, n=5). No significant difference in IGFBP7 secretion in the KD between the IRBC-exposed and control settings (P>0.9999, n=5). (D) Significant difference in rosetting (n=5) was found: Control vs. IGFBP7 (One-way ANOVA with Tukey's test: P=0.0001), and IGFBP7 vs. CSKD-I (P=0.0014). No significant difference found: Control vs. CSKD-U (P=0.9944), Control vs. CSKD-I (P=0.4118), and CSKD-U vs. CSKD-I (P=0.2977). (E) A control experiment (n=9) to assess effect of IGFBP7 on phagocytosis ability of THP-1 using zymosan A, with insets showing THP-1 before (i) and after (ii) engulfing zymosan A, in giemsa-wet mount, 1000× magnification; scale bars: 10 μm. IGFBP7 enhanced phagocytosis of THP-1 (Wilcoxin matched pair-signed rank test P=0.0039). (F) Rosetting rates of Pf co-incubated with monocytes and THP-1 under IGFBP7-free and IGFBP7-supplied conditions (means and S.D. of quintuplicates shown). From two-way ANOVA with Sidak's multiple comparison test, IGFBP7 increased rosetting rates (P<0.0001 and P=0.0013 for monocyte and THP-1 respectively). No significant difference found between the controls (IGFBP7- free) (P=0.9968), as well as between the IGFBP7-supplied conditions of the two groups (P=0.3465). (G) IRBC-phagocytosis rates of monocytes and THP-1 under IGFBP7-free and IGFBP7-supplied conditions (means and S.D. of quintuplicates shown). From two way ANOVA with Sidak's multiple comparison test, phagocytosis rates were lower in IGFBP7-supplied group (P=0.0015 and 0.0011 for monocyte and THP1 respectively). No significant difference found between the controls (IGFBP7-free) (P=0.9595), as well as between the IGFBP7-supplied conditions of the two groups (P=0.9873). (H, I) IGFBP7-exposure affects laboratory-adapted pf IRBC rosetting (n=5) (paired t-test P=0.0001, t=14.88, df=4) (H) and phagocytosis (paired t-test P=0.0009, t=8.98, df=4) (I). (J) Engulfment of a non-rosette-forming IRBC by a peripheral monocyte. Pictures taken 10 s apart. (K, L) Phagocytosis (arrow) of rosettes, in giemsa-wet mount, 1000× magnification, using Olympus BX43 light microscope with built-in camera; scale bars: 10 μm.

Figure 9:
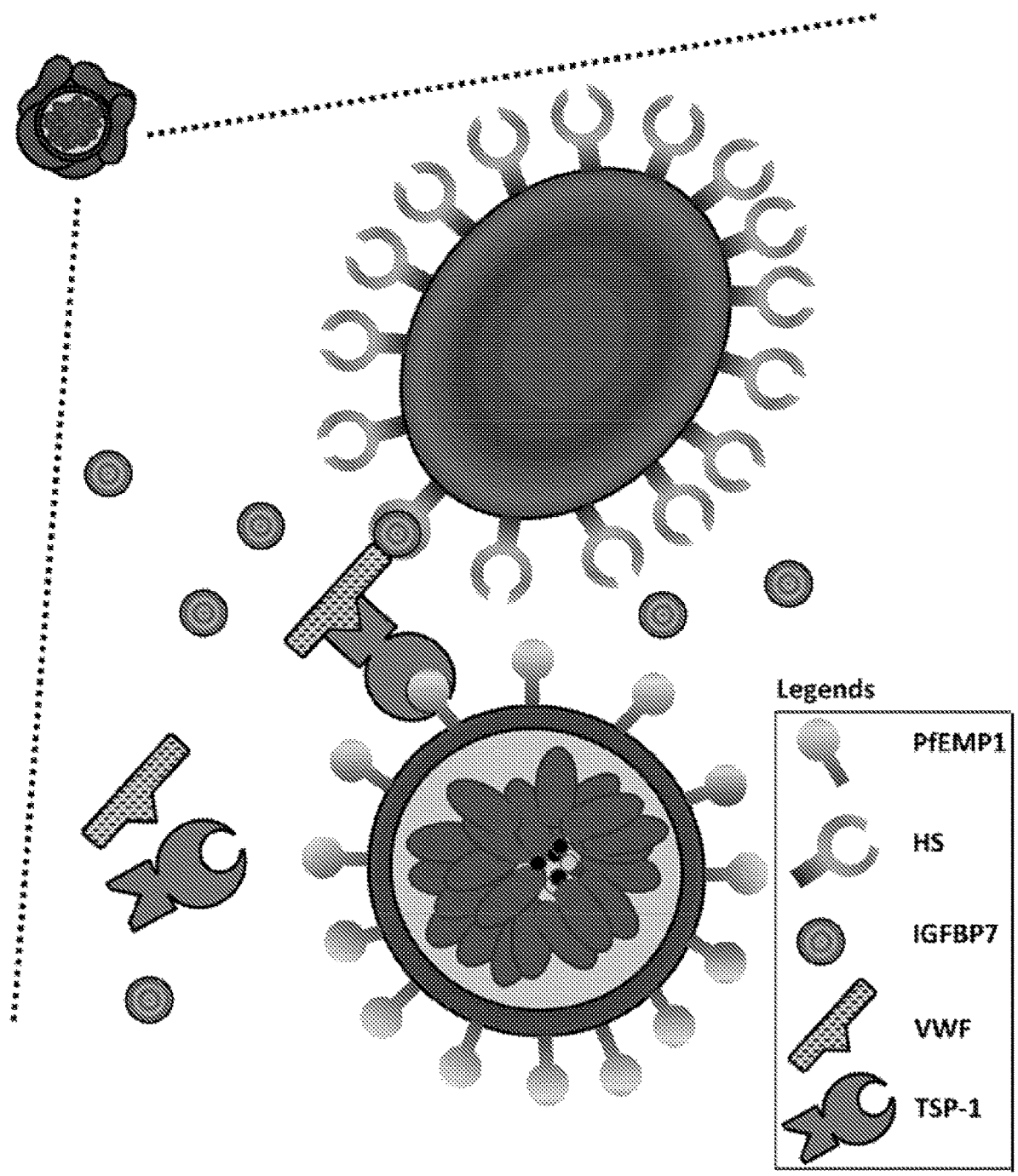

FIG. 9. Schematic diagram illustrating interactions of HS on URBCs, IGFBP7, VWF, TSP-1 and the PfEMP1 on IRBCs. IGFBP7 binds to HS on the surface of URBCs. IGFBP7 also interacts with VWF. VWF can interact with PfEMP1 on the IRBC via TSP1. Without adequate amount of all involving components in the system, this IGFBP7-mediated rosetting may not occur.

Figure 10:
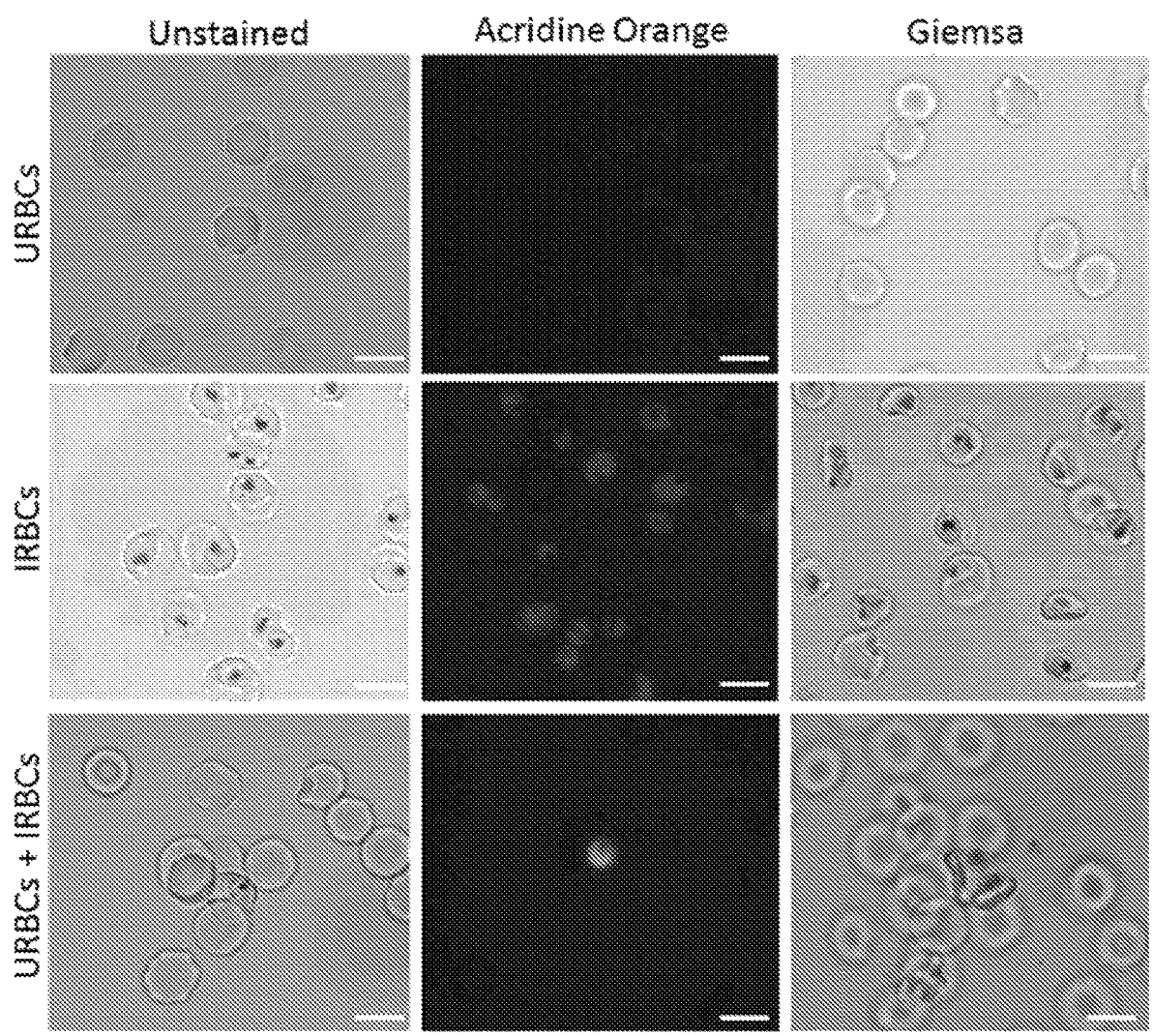

FIG. 10. IRBC, URBC, and IGFBP7. (A). URBC, IRBC, and URBC+IRBC exposed to IGFBP7 visualised with unstained, acridine orange and Giemsa wet mounts, which are the common techniques for rosetting assay. Pictures taken with Nikon Eclipse E200 light microscope. Scale bars represent 10 μm.

Figure 11:
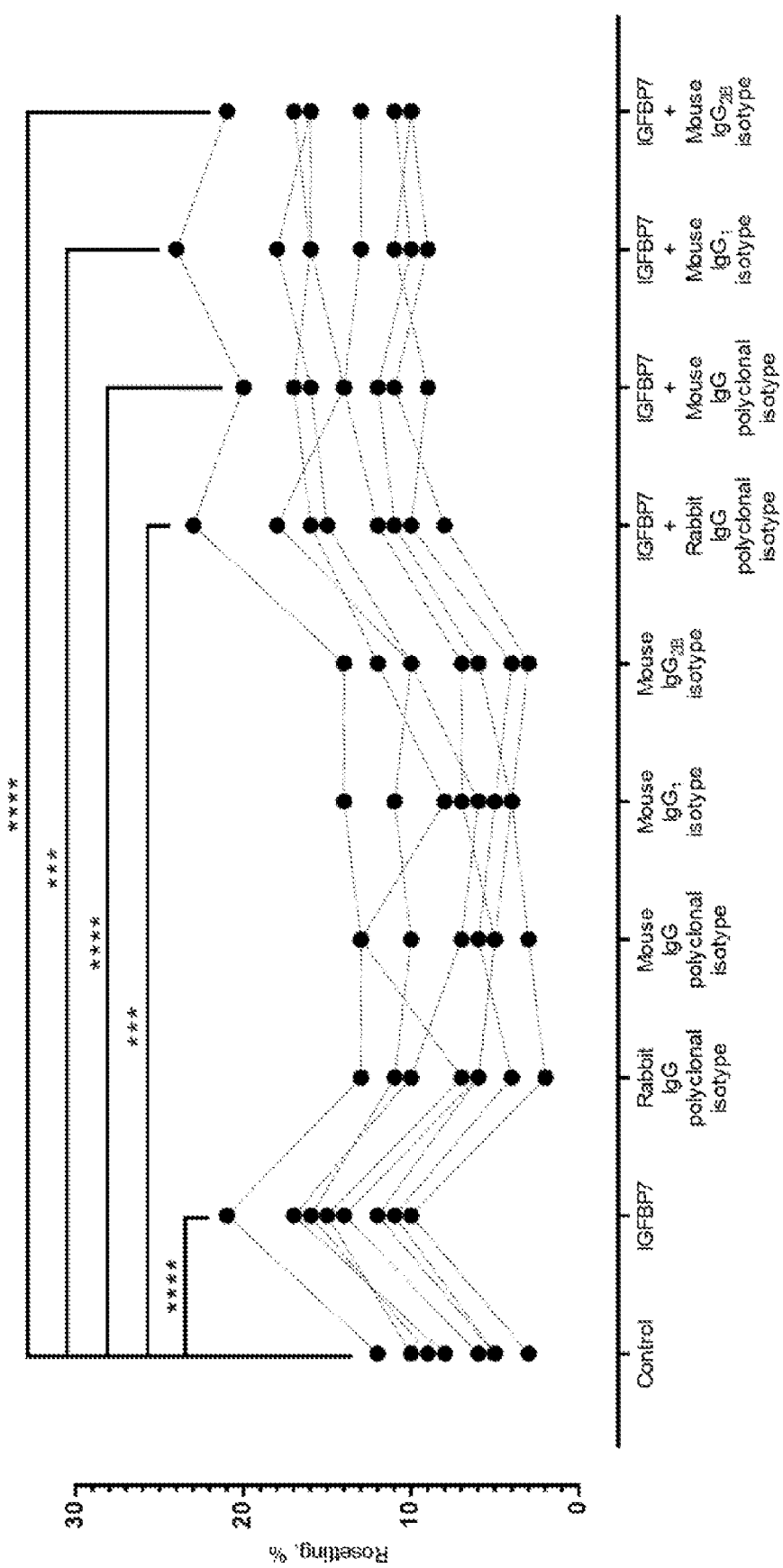

FIG. 11. Rosetting rates of $P.$ $falciparum$ lines (n=8) under different conditions. One way ANOVA with Tukey's multiple comparison test was conducted. IGFBP7 significantly increased rosetting rates (P<0.0001). No significant difference was found between the control and rabbit IgG polyclonal isotype (P>0.9999), mouse IgG polyclonal isotype (P=0.9721), mouse IgG1 isotype (P>0.9999), and mouse IgG2B isotype (P=0.3379). The rosette-stimulatory effect by IGFBP7 was not hampered by these antibody isotypes when compared with the rosetting rates from control group [P=0.0007 for IGFBP7+rabbit IgG polyclonal isotype; P<0.0001 for IGFBP7+mouse IgG polyclonal isotype, P=0.001 for IGFBP7+mouse IgG1 isotype, and P<0.0001 for IGFBP7+mouse IgG2B isotype.

Figure 12:
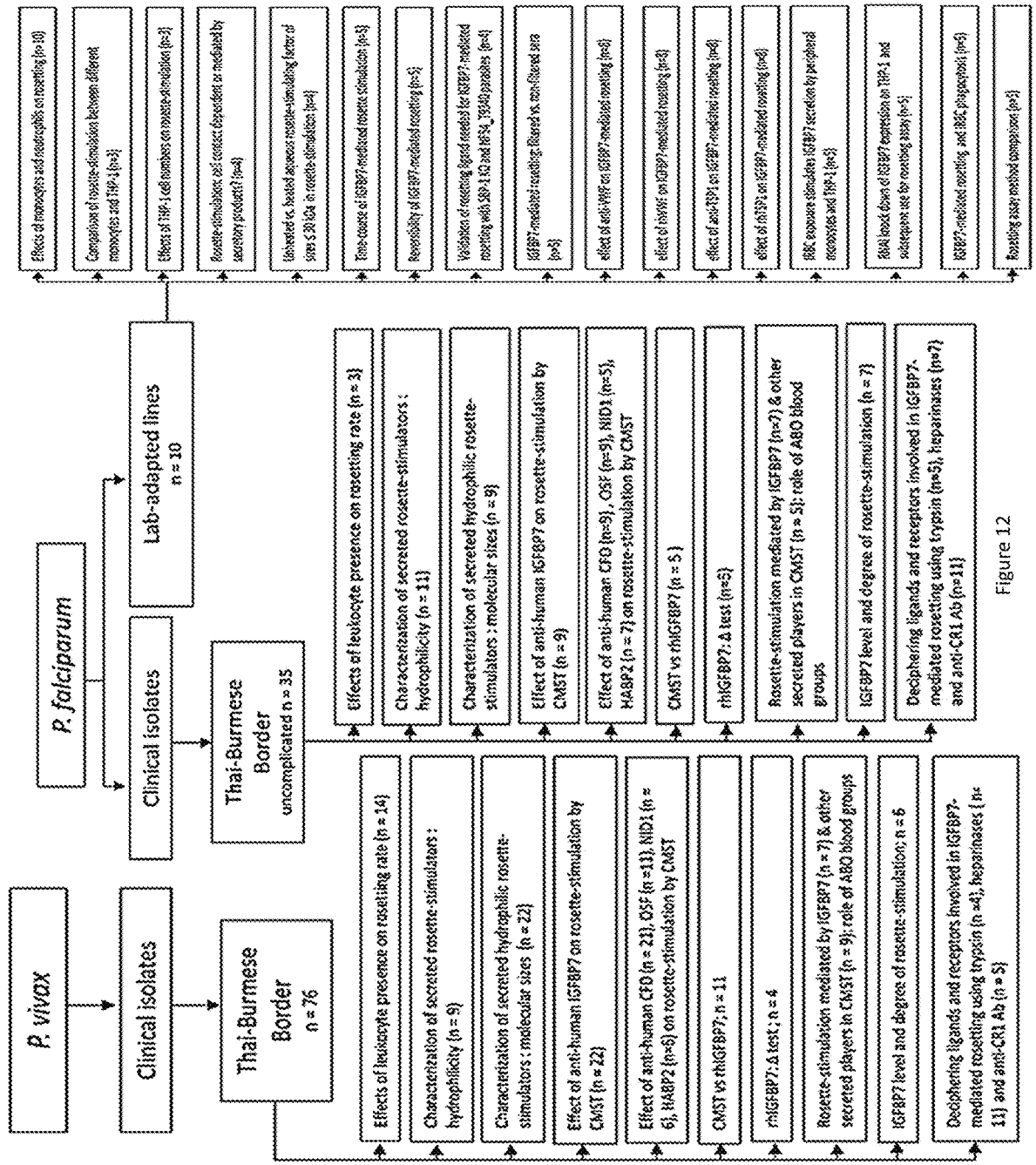

FIG. 12. Experiment flow. Flow chart showing the chronology of experiments done in the project, along with the number of samples recruited for each experiment.

Figure 13:
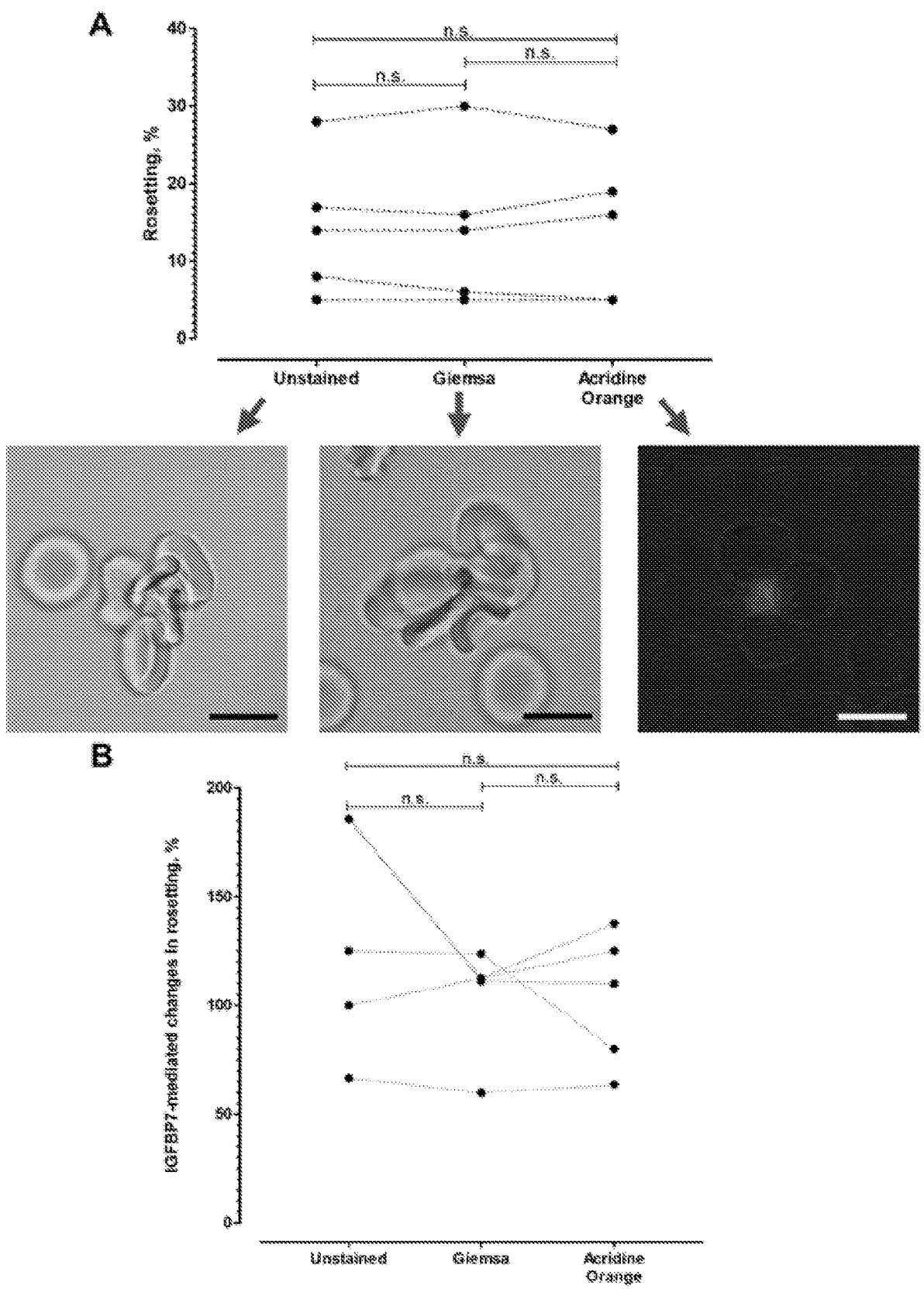

FIG. 13. Method comparison for rosetting assay. (A) Plot of rosetting rates obtained from recruited $P.$ $falciparum$ lines (n=5) using different wet mount methods, with insets underneath the x-axis showing rosettes visualized by respective methods [immersion oil (1000×) magnification, scale bars represent 10 μm]. Pictures of unstained and Giemsa-wet mounts were taken on light microscope Olympus BX43 whereas picture of acridine orange-wet mount was taken on epifluorescence microscope Nikon TS100. One-way ANOVA with Tukey's test: unstained vs. Giemsa: P=0.9517. Acridine orange vs. unstained P>0.9999. Acridine orange vs. Giemsa: P=0.9809. (B) Changes of rosetting rates by IGFBP7 collected using different rosetting assays. Dotted lines were used to show read ups collected from different methods on the same sample. Dataset Giemsa did not pass normality test (Shapiro-Wilk normality test). Friedman with Dunn's test: unstained vs. Giemsa: P=0.3415; unstained vs. acridine orange: P=0.6177; Giemsa vs. acridine orange: P>0.9999. i.e. no significant difference between the methods used. n.s. not significant.

FIGS. 14 to 18 show various data relating to the in vivo experiments described below.

$Plasmodium$ $falciparum$ is responsible for much of the malaria fatalities. During the infection, the parasite modifies the infected erythrocyte architecture, resulting in the infected erythrocytes cytoadhering to the deep microvasculature endothelial cells to escape splenic clearance by the host. However, such escape strategy by the parasite triggers endothelial activation and inflammation, subsequently leads to vascular leakage and damages, hence the severe, potentially fatal malaria complications.

At the moment, few molecules have been suggested as adjunct anti-malarial regime that targets the cytoadhesive properties of infected erythrocytes. Curdlan sulfate is one of the promising adjunct treatment candidates. Curdlan sulfate has 10× lower anticoagulant effect than heparin. The drug has short half-life and low toxicity. Curdlan sulfate has been reported to reduce the severe pathology development of the patients, and has entered phase II clinical trial, as reported in year 2013. The only concern raised regarding usage of this drug was its effect in prolonging blood clotting. While waiting for curdlan sulfate to be officially available for widespread use as an adjunct therapy in malaria treatment, it is important to look for alternative options.

We found that IGFBP7 can stimulate rosetting while preventing and reversing endothelial cytoadhesion of $Plasmodium$ $falciparum$-infected erythrocytes, the pathological phenomenon that leads to severe and potentially fatal outcomes in $falciparum$ malaria. Importantly, we found that in clinical setting, the patients with uncomplicated malaria showed significantly higher plasma IGFBP7 levels than those suffering cerebral malaria. This host-derived protein carries potential to be an adjunct therapeutic regime.

The invention is described in detail in the EXAMPLE below.

EXAMPLE

Methods and Materials

Figures 1B, 1C:
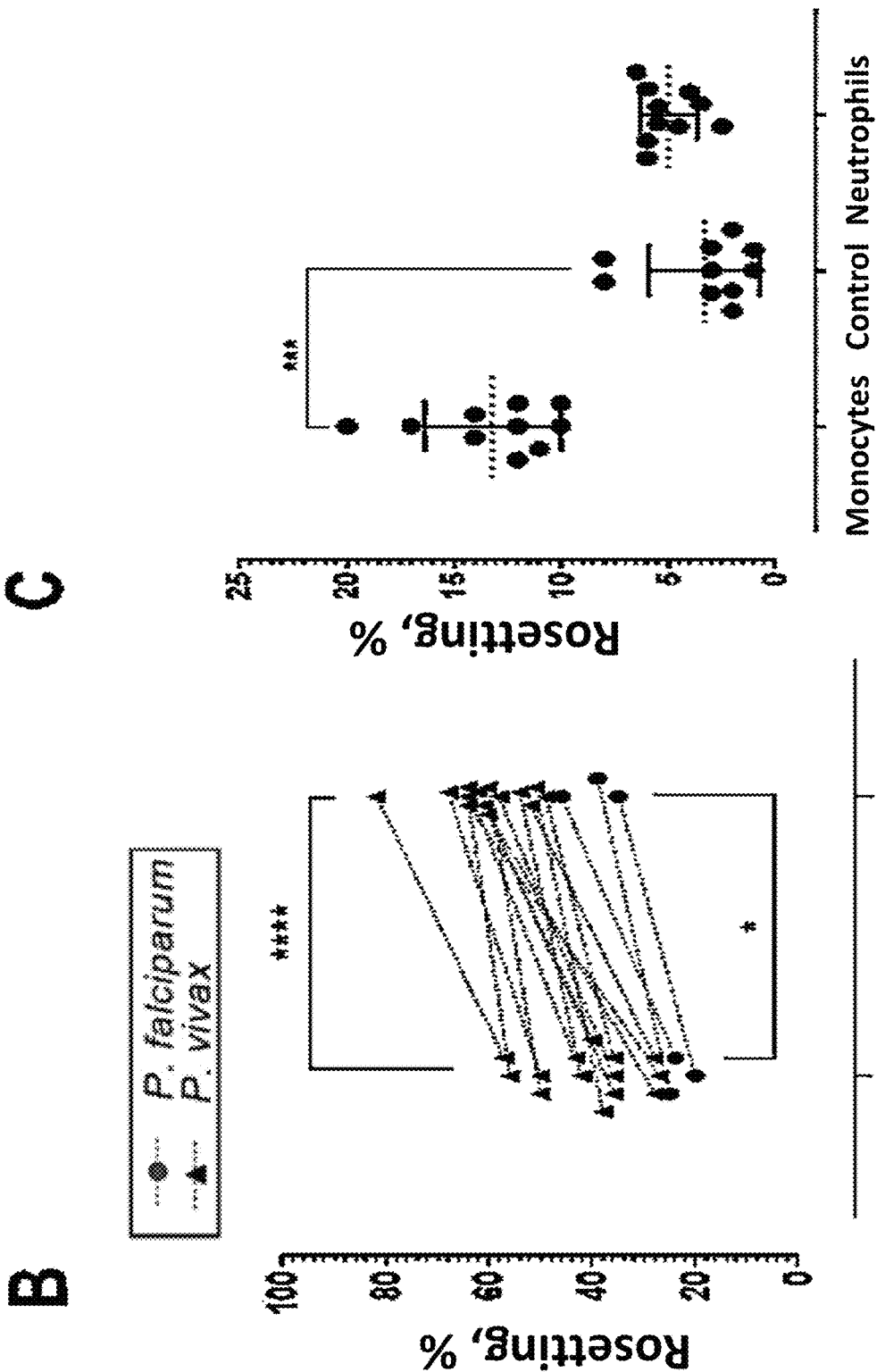

Experiments were performed with isolates of late-stage $P.$ $falciparum$ and $P.$ $vivax$ late stages (experiment flow and materials used in the experiments are available in FIG. 12 and Tables 3-6) unless stated otherwise. The results of the experiments indicated in Tables 3 and 4 are shown in the Figures (e.g. FIG. 1B shows the graph from the experiment designed for 1B using the isolates stated in these tables). Source of the materials (company and Cat #) used are listed in Table 6. All incubations were conducted for one hour at in vitro cultivation conditions unless stated otherwise. Experiments with only one cell line or one parasite line was performed with biological replicates, where the experiments were conducted with multiple sets/batches of the cell/parasite cultures under the same cultivation conditions.

TABLE 3

Recruited $P.$ $falciparum$ isolates from the Thai-Burmese Border.

| Isolate | Gender | Age | Parasit-emia, % | Blood group | Used for experiments |
|---|---|---|---|---|---|
| PID408028 | M | 26 | 1 | B | 1B |
| RDM00036 | M | 63 | 3.4 | O | 1B |

TABLE 3-continued

Recruited *P. falciparum* isolates from the Thai-Burmese Border.

| Isolate | Gender | Age | Parasitemia, % | Blood group | Used for experiments |
|---|---|---|---|---|---|
| RDM00037 | F | 8 | 2.3 | O | 1B |
| RDM103 | M | 41 | 0.4 | B | 2A |
| PID118313 | M | 20 | 0.6 | B | 2A |
| PID403540 | F | 3 | 1 | B | 2A |
| TH004069 | M | 31 | 1 | AB | 2A, 2B, 3A, 3B, 3C |
| MRC0135 | M | 40 | 1.3 | A | 2A, 2B, 3A, 3B, 3C |
| NHP2188 | M | 23 | 19.2 | A | 2A, 2B, 3A, 3B, 3C, 3D, 3E |
| NHP1403 | F | 61 | 9.5 | O | 2A, 2B, 3A, 3B, 3C, 3D, 3E, 4A, 6D |
| NHP1483 | F | 17 | 4.2 | B | 2A, 2B, 3A, 3B, 3C, 3D, 3E, 4C, 4E |
| PID314265 | F | 41 | 0.9 | O | 2A, 2B, 3A, 3B, 3C, 3D, 3E, 4C,4E |
| HP374 | F | 19 | 6.1 | A | 2A, 2B, 3A, 3B, 3C, 3D, 3E, 4C, 4E |
| PID104582 | F | 25 | 0.1 | O | 2A, 2B, 3A, 3B, 3C, 3E, 4C, 4E |
| OZ228 | M | 33 | 0.2 | O | 2B, 3A, 3B, 3C, 3E, 4A, 6A, 6B |
| PID403035 | M | 23 | 0.3 | B | 4A, 6A, 6B, 4C, 4E |
| RDM094 | M | 5 | 1 | B | 4A, 6A, 6B, 6F |
| MMA2156 | F | 58 | 0.7 | O | 4A, 6A, 6B, 6F |
| HP357 | F | 32 | 4.3 | A | 4A, 6A, 6B, 6F |
| OZ234 | M | N/A | 0.1 | O | 6A, 6B, 6F |
| NHP1454 | M | 35 | 4 | A | 4A, 6A, 6B, 6D, 6F |
| HP3069 | F | 17 | 6.3 | B | 6F, 6H |
| MMA4044 | M | 31 | 0.3 | B | 6F, 6H |
| PID423677 | M | 17 | 2.5 | AB | 5A, 6H |
| NHP1338 | M | 35 | 5.2 | AB | 5A, 6H |
| RDM104 | M | 19 | 0.5 | B | 5A, 6H |
| NHP4770 | M | 33 | 4.2 | O | 4A, 6D |
| NHP1481 | F | 4 | 4.4 | B | 4A, 6D |
| NHP0319 | M | 25 | 4.1 | O | 4A, 6D |
| NHP3048 | M | 13 | 6 | A | 4A, 6D |
| NHP4703 | F | 41 | 4.5 | AB | 6D |
| NHP1386 | M | 7 | 15 | A | 6D |
| NHP1401 | F | 19 | 4 | B | 6D, 5A |
| NHP3127 | F | 50 | 4.3 | B | 6D |
| NHP4265 | F | 7 | 8 | B | 6D, 5A |

TABLE 4

Recruited *P. vivax* isolates from the Thai-Burmese Border.

| Isolate | Gender | Age | Parasitemia, % | Blood group | Used for experiments |
|---|---|---|---|---|---|
| BPD 0483 | M | 45 | 0.7 | O | 1B |
| PID411161 | F | 22 | 0.6 | O | 1B |
| PID406704 | M | 33 | 0.6 | B | 1B |
| PID112410 | F | 11 | 0.4 | A | 1B |
| PID416460 | F | 63 | 0.3 | O | 1B |
| PID403915 | F | 41 | 0.6 | O | 1B |
| PID112038 | M | 14 | 0.3 | O | 1B |
| PID416510 | M | 21 | 0.5 | B | 1B |
| BPD491 | M | 10 | 0.3 | O | 1B |
| BPD493 | M | 59 | 0.9 | O | 1B |
| PID403130 | M | 17 | 0.3 | B | 1B |
| PID416546 | M | 21 | 0.4 | A | 1B |
| BPD494 | F | 41 | 0.4 | B | 1B |
| PID100197 | M | 28 | 0.2 | B | 1B |
| PID314183 | M | 16 | 0.03 | O | 2A |
| PID422801 | M | 50 | 0.2 | O | 2A |
| THV004082 | F | 54 | 0.1 | A | 2A |
| PID418099 | M | 17 | 0.03 | O | 2A |
| THV004084 | M | 53 | 0.03 | B | 2A |
| THV004083 | M | 18 | 0.02 | B | 2A |
| PID404586 | F | 6 | 0.4 | O | 2A, 6A, 6B |
| THV004039 | F | 43 | 0.02 | O | 2A |
| PID313030 | F | 57 | 0.3 | O | 2A |
| PID422901 | M | 43 | 0.3 | B | 6A, 6B |

TABLE 4-continued

Recruited *P. vivax* isolates from the Thai-Burmese Border.

| Isolate | Gender | Age | Parasitemia, % | Blood group | Used for experiments |
|---|---|---|---|---|---|
| PID406998 | F | 4 | 0.3 | O | 2C |
| PID409065 | F | 6 | 0.4 | A | 2C, 3A |
| PID424107 | M | 16 | 0.3 | A | 2C, 3A, 3B, 3C, 3D, 3E, 6A, 6B |
| PID416055 | F | 6 | 0.5 | B | 2C, 3A, 3B, 3C, 3D, 3E |
| PID116351 | F | 24 | 0.4 | O | 2C, 3A, 3B, 3C, 3D, 3E, 6A, 6B |
| PID424121 | M | 6 | 0.05 | B | 2C, 3A, 3B, 3C, 3D, 3E |
| PID109874 | F | 28 | 0.03 | O | 2C, 3A, 3B, 3C, 3D, 3E |
| PID423369 | M | 30 | 0.4 | B | 2C, 3A, 3B, 3C, 3D, 3E |
| PID406998 | F | 6 | 0.7 | O | 2C, 3A, 3B, 3C, 3D |
| PID403063 | M | 17 | 0.3 | B | 2C, 3A, 3B, 3C, 3D |
| PID108989 | M | 29 | 0.05 | O | 2C, 3A, 3B, 3C, 3D, 6A, 6B |
| PID423135 | F | 14 | 0.4 | O | 2C, 3A, 3B, 3C, 3D |
| PID418481 | M | 8 | 0.03 | AB | 2C, 3A, 3B, 3D, 4D |
| PID404330 | F | 10 | 0.1 | AB | 2C, 3A, 3B, 3C, 3D, 4D |
| PID409345 | M | 13 | 0.7 | O | 2C, 3A, 3B, 3C, 3D, 4D, 6A, 6B |
| PID423814 | M | 10 | 0.3 | O | 2C, 3A, 3B, 3D, 4D |
| PID111380 | M | 45 | 0.05 | A | 2C, 3A, 3B, 3D, 4D |
| PID423764 | M | 45 | 0.3 | O | 2C, 3A, 3B, 3D, 4D |
| PID105805 | M | 12 | 0.3 | A | 2C, 3A, 3B, 3D, 4D |
| PID412151 | F | 57 | 0.5 | O | 2C, 3A, 3B, 3D, 4D |
| PID415994 | M | 2 | 0.5 | O | 2C, 3A, 3B, 3C, 3D, 4D, 6A, 6B |
| PID414711 | F | 8 | 0.3 | B | 2C, 3A, 3B, 3D, 4D |
| PID424477 | M | 4 | 0.3 | O | 3A, 3B, 3D, 4D, 6A, 6B |
| PID422693 | M | 38 | 0.7 | O | 6A, 6B |
| PID424506 | F | 13 | 0.05 | O | 6A, 6B |
| PID406889 | F | 18 | 0.1 | AB | 6A, 6B |
| PID401131 | F | 13 | 1.1 | A | 4F, 5A, 6I |
| PID425407 | M | 27 | 0.03 | O | 4F, 5A |
| PID425544 | M | 13 | 0.3 | O | 4F, 5A, 6I |
| PID302114 | F | 20 | 0.5 | A | 4F, 5A |
| PID109371 | F | 15 | 0.2 | O | 6G |
| PID108371 | M | 22 | 0.2 | B | 6G |
| PID314653 | M | 20 | 0.8 | B | 6G, 6I |
| PID421209 | M | 4 | 0.5 | O | 6G, 6I |
| PID419197 | F | 2 | 0.5 | O | 6G, 6I |
| THV004096 | F | 47 | 0.5 | O | 6G |
| PID410117 | F | 6 | 0.8 | O | 6G |
| PID406998 | F | 6 | 0.7 | O | 6I |
| PID424601 | F | 5 | 2 | B | 6I |
| BPD472 | F | N/A | 0.5 | A | 6I |
| PID425305 | M | 13 | 0.03 | O | 6I |
| PID427120 | F | 9 | 0.3 | A | 6E |
| PID323623 | F | 12 | 0.3 | B | 6E |
| PID121917 | M | 15 | 0.1 | O | 6E |
| PID122557 | M | 17 | 0.2 | O | 6E |
| PID427316 | M | 51 | 0.1 | B | 6E |
| PID428734 | M | 24 | 0.9 | AB | 4B |
| DMA520 | F | 26 | 0.1 | B | 4B |
| PID427309 | F | 14 | 2.8 | B | 4B |
| PID122775 | N/A | 19 | 0.4 | O | 4B |
| PID428843 | M | 23 | 0.1 | B | 4B |
| PID423539 | M | 14 | 0.5 | A | 4B |

TABLE 5

Recruited laboratory adapted- *P. falciparum* lines.

| Code | Notes |
|---|---|
| 3D7 | maintained in SIgN |
| FVT402 | adapted from SMRU clinical isolate |

TABLE 5-continued

Recruited laboratory adapted- *P. falciparum* lines.

| Code | Notes |
| --- | --- |
| FVT201 | adapted from SMRU clinical isolate |
| MKK183 | adapted from SMRU clinical isolate |
| CS2-SBP1-KO | prepared in ANU and maintained in SIgN |
| CS2-WT | prepared in ANU and maintained in SIgN |
| WPP3065 | adapted from SMRU clinical isolate |
| WPP2803 | adapted from SMRU clinical isolate |
| NHP1106 | adapted from SMRU clinical isolate |
| NHP4770 | adapted from SMRU clinical isolate |
| NF54_VAR2CSA_WT | Provided by Benoit Gamain, INSERM |
| NF54_T934D | Provided by Benoit Gamain, INSERM |

1. Ethical Statement

Malaria-infected samples were collected in Shoklo Malaria Research Unit (SMRU) under approved ethics: OXTREC 04-10 (University of Oxford, UK); TMEC 09-082 (Ethics Committee, Faculty of Tropical Medicine, Mahidol University, Thailand).

2. Cell Lines

Human monocytic THP-1 cell line (Source: ATCC®) was used in this study. The cells were tested Mycoplasma-free using the MycoAlert™ Plus Mycoplasma Detection Kit (Lonza).

3. Blood Sample Processing

Clinical isolates (uncomplicated malaria cases) from SMRU were recruited. Blood (volume: 3 ml) were collected using BD Vacutainer® with lithium heparin anticoagulant. Blood groups were determined with TransClone® Anti-A and Anti-B antibodies. Blood samples were centrifuged at 1500 g for five minutes. Plasma was removed, and the buffy coat was carefully collected. CF11-packed column was used to filter remaining leukocytes. The parasites were matured in vitro with 5% haematocrit culture condition using 20% human homologous serum-enriched RPMI 1640 medium for *P. falciparum*, and McCoy's 5 A for *P. vivax*, under gas condition of 4% $CO_2$ and 3% $O_2$.

4. Human Leukocytes-*Plasmodium* Rosetting Correlation Testing

Leukocytes and red blood cells (RBC) from clinical samples were isolated and divided into two groups. One group consisted of only RBC. In another group, RBC and leukocytes in physiologic ratio of 500:1 were matured in vitro, prior to rosetting assay. There are different wet mount-based techniques for rosetting assay. We compared three commonly used techniques and validated that they can be used interchangeably (FIG. 13), as elaborated in the following sections.

5. Rosetting Assay

Rosetting assay was conducted when 70% of the parasite population reached late stages (late trophozoites and schizonts) unless stated otherwise. The parasite culture suspension was stained subvitally with Giemsa (5% stain working concentration) for 20 minutes. Subsequently, 7.6 µl stained suspension was pipetted onto a clean glass slide, immediately covered with a 22×32 mm glass cover slip. The wet mount was examined with light microscope using 1000× magnification. Rosetting rate (percentage of rosetting IRBCs) was defined as the percentage of IRBC (over 200 recruited IRBC) that form rosettes. Experiments were conducted in blinded manner.

6. Comparison of Different Rosetting Assay Methods

There are different microscopy-based techniques for rosetting assay, namely the unstained, Giemsa-stained, and the fluorescent dye Acridine Orange (AO)-stained wet mounts, and none of them have been thoroughly validated and compared. When majority of the *P. falciparum* culture population (laboratory adapted lines 3D7, CS2-WT, FVT201, MKK183, WPP3065) reached late stages, the culture suspension was used for this experiment. For each parasite line, the culture suspension was divided into three parts. One aliquot was stained with 5% Giemsa subvitally for 15 minutes prior to wet mount preparation for rosetting assay. Another one was stained with Acridine Orange (working concentration 2 µg/ml) for 15 minutes prior to wet mount for rosetting assay. The third aliquot was used for unstained wet mount preparation prior to rosetting assay. Rosetting rates were determined and compared.

The late stage-IRBCs were purified with MACS-LD columns. Only the yields with IRBC purity of at least 90% were used. The purified IRBCs were divided into two groups. One was mixed with URBCs to make a 3% parasitemia packed cell mixture. The other group was used as purified IRBC group. Packed URBCs from two healthy individuals were used as controls. Each of these groups were further divided into two parts, where one was exposed to IGFBP7 (100 ng/ml) whereas the other one acted as IGFBP7-free control. All groups were suspended with culture medium, and incubated for one hour at in vitro cultivation conditions prior to rosetting assay using the Giemsa-wet mount, Acridine Orange-wet mount and unstained wet mount methods described in previous paragraph.

In our hands, these three techniques yielded comparable rosetting rates with or without IGFBP7 (FIGS. 13A and B). Importantly, in all techniques applied, IGFBP7 did not exert clumping effect on groups consisted of only URBC and IRBC (FIG. 10), demonstrating the IRBC-URBC specificity of IGFBP7 interaction. Of note, the formation of some IRBC aggregates when enriched IRBC are cultured has been described previously by Adams et al. However, addition of IGFBP7 did not aggravate the IRBC aggregate formation or enlarge the size of the aggregates (data not shown). Thus, we have validated that the currently available microscopy-based rosetting assays have similar reliability and can be used interchangeably.

7. Human Monocytes and Neutrophils on Rosetting

Three Percoll gradients were prepared from the isotonic Percoll (9 parts of Percoll stock+1 part of 10×PBS), namely the 81% Percoll, 68% Percoll, and 55% Percoll. A 15 ml conical centrifuge tube was layered with 3 ml of 81% Percoll solution, followed by 3 ml of 68% Percoll solution. Blood from healthy donors were centrifuged for 5 minutes at 1500 g. Subsequently, three quarter of the plasma supernatant was removed, followed by careful collection of leukocyte-rich buffy coat layer. Uptake of RBC must be avoided as much as possible. The leukocytes were suspended with 3 ml of 55% Percoll, and carefully transferred onto the Percoll layered column prepared. The gradient tube was centrifuged at 1500 g for 20 minutes. The upper two-third portion of the top layer was removed. The remaining one-third portion (the "55-68" interface zone, i.e. monocyte-rich PBMCs) was collected. After that, the upper two-third portion of the second layer was removed, and the "68-81" interface (neutrophil-rich PMNs) was collected into another conical centrifuge tube. The separated monocytes and neutrophils were washed with RPMI 1640 medium. After that, trypan blue exclusion examination and Giemsa-stained blood smear examination were performed to evaluate viability, cell numbers, and purity of cell population harvested. The cells were suspended in RPMI 1640 and incubated in petri dishes for three hours at 37° C. For the monocyte group, cells that adhered to the petri dish (monocytes) were retained for experiments whereas the non-adhered cells were removed from the petri dishes.

*P. falciparum* (three laboratory adapted lines: 3D7, FVT402, FVT201, and one clinical isolate RDM00036) were cultured (5% haematocrit, 3% parasitemia). Culture suspensions were incubated with or without neutrophil (RBC:neutrophils ratio as 1,000:1) or monocyte (RBC: monocytes ratio as 10,000:1) from individual donors. Rosetting assay was performed afterwards. In a separate experiment, monocytes from two healthy donors were purified via Ficoll density gradient concentration method, followed by $CD14^+$ microbeads sorting. The impacts of purified $CD14^+$ monocytes and $CD14^-$ peripheral blood mononuclear cell (PBMC), as well as the human monocytic THP-1 cell line on rosetting rates of *P. falciparum* lines were assessed using laboratory-adapted *P. falciparum* lines (FVT402, 3D7 and MKK183). For each parasite line, three batches of cultures (thawed from vials that were cryopreserved at different times) were used for three experiment replicates).

8. THP-1 and *P. falciparum* Rosetting

Human monocytic THP-1 cell line (Mycoplasma-free) was cultured [10% FBS-enriched RPMI 1640] and expanded with two methods; one being cultivated with stringent control of cell density below $10^6$ cells/ml as undifferentiated THP1 (UT) cells. The other one was allowed to replicate until the cell population reached $6 \times 10^6$ cells/ml for differentiation into macrophage-like THP-1 (MT) cells. Supernatant (2 ml) collected from *P. falciparum* culture (rich with parasite antigens) was added into the second group, along with Interferon gamma (IFNγ) (final concentration 50 ng/ml). Three days later, culture medium was discarded. $2.5 \times 10^5$ cells were transferred into each well of a 48-well flat bottom culture plate whereas the remaining cells continued to be cultured in the flask. All cell cultures were replenished with fresh culture medium (5% FBS-enriched RPMI 1640) without addition of *P. falciparum* culture supernatant and IFNγ. Two days later, cell counts were performed. The culture supernatant (CS) from the 48-well plate (1 ml for each well, with cell count of $10^6$ cells) was collected as CSMT for subsequent experiments. The preparation was repeated with the UT cells to collect CSUT. The attached, differentiated MT cells in the culture flask were harvested by removing the culture medium, followed by addition of pre-chilled 1×PBS into the culture flask and incubation on ice for 10 minutes. UT and MT of different cells numbers were tested in the rosetting assay in triplicates for each parasite line. CSMT and CSUT (10 μl from culture of $10^6$ cells/ml), and interferon gamma (IFNγ; at 50 ng/ml) were also tested in the rosetting assay.

9. Identification of Mediators Mediating Rosette-Stimulation

CSMT was fractionated into lipophilic (lipid) and aqueous (aq) compartments using Folch's chloroform-methanol extraction method[79]. Briefly, chloroform-methanol extraction mixture (2:1 ratio) was prepared. Washing liquid consisted of chloroform, methanol and distilled water in 3:48:47 ratio was prepared. CSMT (1 ml, from culture with cell density of $10^6$ cells/ml) was mixed with 19 ml extraction mixture. The mixed liquid was washed with 4 ml of distilled water and allowed to settle for a few minutes. Two phases of liquid formed from this. The upper portion (around 40% of the total volume) being the aq fraction whereas the lower part being the lipid fraction. The aq fraction was collected separately. The remaining liquid was washed gently with washing mixture for three times to remove the interphase. After that, the lipid phase was collected. The collected aq and lipid fractions were dried with vacuum concentrator. After that, the pellet was suspended with 500 μl distilled water. Vortexing was applied to facilitate solubilisation of the lipid pellet. These fractions were tested with rosetting assay. The aq fraction was further subjected to size-based fractionation using Vivaspin20 twin PES membrane (30,000 MWCO) concentrator and tested with rosetting assay. A separate experiment was conducted with laboratory-adapted *P. falciparum* lines (3D7, FVT402, FVT201, MKK183) to compare the rosette-stimulating effect of the aq≤30 kDa fraction and the aq≤30 kDa fraction that was heated for one hour at 56° C. Subsequently, the aq fraction 30 kDa) was digested for mass spectrometry analysis using Orbitrap Fusion mass spectrometer.

10. Mass Spectrometry

Sample was in-solution digested. Initial denaturation was done with 8M Urea in 50 mM Tris-HCl pH 8.5. Following denaturation, proteins were reduced in 25 mM Tris-(2-carboxyethyl) phosphine (TCEP), alkylated with 55 mM chloroacetamide (CAA) and further diluted with 100 mM triethylammonium bicarbonate (TEAB) to achieve <1M Urea concentration. Two step enzyme digestion with lysyl Endopeptidase® (LysC) and Trypsin was performed for 4 h (1:100—enzyme/protein ratio) and 18 h (1:100) respectively. After acidification with 1% trifluoroacetic acid (TFA), desalting was done using Sep-Pak C-18 columns. Organic phase was evaporated in the vacuum centrifuge. For High pH reverse phase initial separation sample was re-suspended in 10 mM Ammonium Formate/5% Acetonitrile. Two hundred minutes continuous gradient separation (Solvent A: 10 mM Ammonium Formate pH10.5/Solvent B: 10 mM Ammonium Formate pH10.5/90% Acetonitrile) was performed on ÄKTA Micro system using Gemini 5u/C-18/ 110A, 150 mm×1 mm column. Collected fractions were combined into 14 fractions, evaporated and used for mass spectrometry analysis. Mass spectrometry analysis was performed on Orbitrap Fusion mass spectrometer coupled to nano-ultra-high-performance liquid chromatography (UHPLC) Easy nano liquid chromatography (nLC 1000 system). Fractions were injected and separated on in-house prepared (C-18 ReproSil Pur Basic beads 2.5 um) fused silica emitter column 20 cm×75 μm in 75 min gradient (solvent A: 0.1% formic acid; solvent B: 0.1% formic acid/99.9% acetonitrile) in data dependent mode using Orbitrap (OT) and Ion trap (IT) detectors simultaneously (speed mode −3 sec cycle) with ion targets and resolution (OT-MS 2×E5, resolution 60K, OT-MS/MS 3.5E4, resolution 15 k; IT-MS/MS 2E4, Normal scan). Peak lists were generated with Proteome Discoverer 1.4 software and searches were done with Mascot 2.5 against forward and decoy Human-HHV4 Uniprot database (88,559 entries) with following parameters: precursor mass tolerance [mass spectrum (MS)] 30 ppm, OT-MS/MS 0.06 Da, IT-MS/MS 0.6 Da; 2 miss cleavages; static modifications: carbamidomethyl (C), variable modifications: oxidation (M), deamidated (NQ), acetyl N-terminal protein. Forward/decoy searches were used for false discovery rate (FDR) estimation (FDR 1%). Peak lists were generated.

Following data review, coupled with critical information (i.e. the protein's subcellular location and cellular functions) from UNIPROT, candidates were shortlisted for further validation. The parasite culture suspensions were incubated with CSMT and antibodies against the shortlisted proteins (see Table 6, items 35, 37, 39-41) and tested in rosetting assay at a final concentration of 25 μg/ml.

TABLE 6

Source of materials and products used in the experiments.
Items are listed in alphabetical order.

| No. | Item | Source |
|---|---|---|
| 1 | Acridine Orange | ThermoFisher Scientific Cat #1301 |
| 2 | ÄKTA Micro System | GE Healthcare |
| 3 | Albumax II | Gibco ™ Cat #11021045 |
| 4 | Anti-A (AB01)antibody | TransClone ® Bio-Rad Cat # 470350 |
| 5 | Anti-B (AB02) antibody | TransClone ® Bio-Rad Cat # 470351 |
| 6 | BD Vacutainer ™ with lithium heparin | ThermoFisher Scientific Cat # 02-657-28 |
| 7 | C-18 ReproSil Pur Basic beads 2.5 um | Dr Maisch Cat #r125.b9 |
| 8 | CD14+ microbeads | Miltenyi Biotech Cat # 130050201 |
| 9 | Cellulose acetate syringe filter, pore size 0.45 μm | Sartorius Minisart ®, Sigma-Aldrich Cat # 16555-K |
| 10 | Centrifuge | Sorvall ® Legend ® RT Plus |
| 11 | CF11 cellulose powder | Sigma-Aldrich ® Cat # 318094 |
| 12 | EASY nLC1000 system | ThermoFisher Scientific Cat #LC120 |
| 13 | Epifluorescence microscope | Nikon Eclipse TS100 |
| 14 | Falcon ® Cell Culture Flask T25, filter cap | VWR ™ Cat #29185298 |
| 15 | Fetal Bovine Serum (FBS) | Gibco ™ Cat # 10500 |
| 16 | Ficoll-paque | GE Healthcare Cat # 17-5442-02 |
| 17 | Flat bottom culture plate, 48 well | NUNC ™ Cat #150687 |
| 18 | Flat bottom plate, 96 well | NUNC ™ Cat #44240421 |
| 19 | Gemini 5u/C-18/110A, 150 mm × 1 mm column | Phenomenex Cat #00F-4435-A0 |
| 20 | Giemsa | Merck Cat # HX60416604 |
| 21 | Glass coverslip 22 × 32 mm | Mariendfeld Cat #0101112 |
| 22 | Prism 7.0 | GraphPad |
| 23 | Heparinase I | R&D Systems ® Cat # 7897-GH-010 |
| 24 | Heparinase III | R&D Systems ® Cat # 6145-GH-010 |
| 25 | Hexadimethrine bromide | Sigma-Aldrich ® Cat # H9268 |
| 26 | Human IGFBP7 DuoSet ® ELISA kit | R&D Systems ® Cat # DY009 |
| 27 | IMDM medium | Gibco ™ Cat #31980-030 |
| 28 | Lab-Tek ™ 8-chamber-slides | ThermoFisher Scientific Cat #177445 |
| 29 | Lysyl endopeptidase ® (LysC) | Wako Cat #125-02541 |
| 30 | MACS-LD columns | Miltenyi Biotec Cat # 130042901 |
| 31 | Mascot 2.5 | Matrix Science |
| 32 | McCoy's 5A medium | Gibco ™ Cat #12330-031 |
| 33 | Microplate reader Tecan i-Control | Tecan ® |
| 34 | Mission ™ shRNA Lentiviral transduction particles | Sigma-Aldrich ®, hPGK-Puro__CMV-tGFP; SHCLNV-NM__001553; TRC#TRCN0000077943 |
| 35 | Mouse IgG, polyclonal-anti-human HABP2 | Abnova Cat # H00003026-B01P |
| 36 | Mouse IgG, polyclonal-isotype control | Abcam Cat # ab37355 |
| 37 | Mouse IgG$_1$, anti-human CFD | R&D Systems ® Cat # MAB18241 |
| 38 | Mouse IgG$_1$, anti-human CR1(CD35) | BD Pharmingen ™ Cat # 555451 |
| 39 | Mouse IgG$_1$, anti-human IGFBP7 | SinoBiological Cat # 13100-MM01 |
| 40 | Mouse IgG$_1$, anti-human NID1 | R&D Systems ® Cat # MAB2570 |
| 41 | Mouse IgG$_1$, anti-human periostin/OSF-2 | Sigma-Aldrich ® Cat # SAB4200197 |
| 42 | Mouse IgG$_1$ isotype control | R&D Systems, Cat # MAB002 |
| 43 | Mouse IgG$_{2B}$, anti-human TSP-1 | R&D Systems ®, Cat # MAB 3074 |
| 44 | Mouse IgG$_{2B}$ isotype control | R&D Systems, Cat # MAB004 |
| 45 | MycoAlert ™ Plus Mycoplasma detection kit | Lonza, Cat # LT07-705 |
| 46 | Orbitrap Fusion ™ mass spectrometry | ThermoFisher Scientific Cat # IQLAAEGAAPFADBMBCX |
| 47 | Percoll ® | Sigma-Aldrich ® Cat # P1644 |
| 48 | Proteome Discoverer 1.4 software | ThermoFisher Scientific |
| 49 | Puromycin | Sigma-Aldrich ® Cat # 9620 |
| 50 | Rabbit IgG, polyclonal-anti-human VWF | Abcam Cat # ab6994 |
| 51 | Rabbit IgG, polyclonal-isotype control | Abcam Cat # ab37415 |
| 52 | Recombinant human interferon gamma IFNγ | R&D Systems ® Cat #285-IF |
| 53 | Recombinant human IGFBP7 (rhIGFBP7) | ProSpec Cat # cyt-788 |
| 54 | Recombinant human VWF (rhVWF) | Abcam Cat # ab152801 |
| 55 | RPMI 1640 medium | HyClone ™ Cat # SH30255.01 |
| 56 | Sep-Pak C-18 columns | Waters Cat # WAT051910 |
| 57 | Trypan Blue | Sigma-Aldrich ® Cat #T6146 |
| 58 | Trypsin | HyClone ™ Cat # SV30031.01 |
| 59 | Trypsin Gold, Mass Spectrometry Grade | Promega Cat #V5280 |
| 60 | Vivaspin20 twin PES membrane 30 kDa concentrator | Sartorius Cat # Z629472 |
| 61 | Zymosan A | Sigma-Aldrich ® Cat # Z4250 |

11. IGFBP7 and Rosetting

The parasite culture suspension was divided into three groups, one served as control, the second group was added with recombinant human IGFBP7 (final concentration 100 ng/ml), and the third group was mixed with CSMT (CSMT:parasite culture=1:3). After one hour of incubation under in vitro cultivation conditions, rosetting assay was conducted. Separately, a portion of the IGFBP7 suspension was heat-denatured at 95° C. for one hour, prior to use in rosetting assay.

Parasite cultures were incubated with IGFBP7 (working concentrations 0-25,000 ng/ml) prior to rosetting assay. Time course experiments were performed with laboratory-adapted *P. falciparum* lines (3D7, MKK183, FVT402, FVT201, WPP3065) incubated with IGFBP7 (100 ng/ml). Rosetting assay was conducted after five minutes, using 7 µl of the suspension. The remaining suspension was kept back into the incubator. Rosetting assay was repeated at five minute-intervals until one hour-post-IGFBP7 exposure. Reversibility of IGFBP7-mediated rosette-stimulation was also tested. Parasite lines (3D7, MKK183, FVT402, FVT201, WPP3065) were incubated with IGFBP7 (100 ng/ml) and rosetting assay was conducted with 7 µl of the suspension. The remaining suspension was centrifuged at 1500 g for five minutes. Supernatant was removed, and the pellet was washed thrice with culture medium, followed by re-suspension with culture medium. Five minutes later, 7 µl of the suspension was taken for rosetting assay, subsequently repeated at five minute-intervals up to one-hour post-IGFBP7 removal.

12. Identification of Rosetting Ligands and Receptors that Interact with IGFBP7

Magnetic activated cell sorter (MACS)-sorted late stage-IRBC (purity 95%) were trypsinized at different working concentrations. The first group was mixed with enzyme trypsin (final trypsin concentration of 10 µg/ml), and the second was mixed with enzyme trypsin (final trypsin concentration of 1 mg/ml). The third served as untreated control. The cells were incubated at 37° C. for 30 minutes. After that, the cells were washed with serum-enriched medium for three times. Each group was incubated with or without IGFBP7 (100 ng/ml) prior to rosetting assay. *P. falciparum* line CS2 deficient of SBP1 [(SBP1-KO-CS2), which lacks *P. falciparum* erythrocyte membrane protein 1 (PFEMP1) on its IRBC surface] and its wild type (CS2-WT) counterpart were cultured as described. Their rosetting rates post-incubation with IGFBP7 at different concentrations were determined. *P. falciparum* clones NF54 VAR2CSA_WT and NF54_T934D (cannot express PfEMP1 variant VAR2CSA on IRBC surface[32]) were cultivated. Experiments were conducted when parasite population reached late stages. For each parasite line, two conditions were applied; one was incubated with IGFBP7 (100 ng/ml) whereas the other one acted as IGFBP7-free control. Rosetting assay was conducted afterwards. Five replicates were conducted for each experiment setting. In a separate experiment, a laboratory-adapted clinical isolate from Thai-Burmese border (NHP1106) was cultivated and staging of parasites was tightly synchronised. Experiment was conducted when the parasite population reached late rings (~hour 16-26). Two settings were prepared; one was incubated with IGFBP7 (100 ng/ml) and the other acted as IGFBP7-free control. One hour of incubation under in vitro cultivation conditions was done prior to rosetting assay. Nine replicates (across 3 cycles of cultivations) were conducted.

The role of heparan sulfate (HS) in IGFBP7-mediated rosetting was also tested. URBC (blood group O) were treated with heparinase I (final working concentration of 25 µg/ml) or heparinase III (final working concentration of 25 µg/ml), with the untreated URBC served as control. The enzyme-erythrocyte mixtures and the untreated controls were incubated at 37° C. for 30 minutes. After that, the suspension was centrifuged to remove supernatant.

The treated erythrocytes were washed with 20% human serum enriched-culture medium for three times. Subsequently, cells were suspended in plain culture medium. The prepared cells were kept at 4° C. until use within one week. Late stage-IRBC were concentrated with MACS. The IRBC (IRBC purity: 90-96%) were divided into three groups, each mixed with the control, heparinase I-treated and heparinase III-treated URBC respectively.

The roles of complement receptor 1 (CR1/CD35) and A/B blood antigens were also investigated. Recruited isolates were matured in vitro, subsequently divided into four groups. One group served as the control, another group was added with rhIGFBP7 (final concentration 100 ng/ml). The third group was added with mouse anti-human CR1 (CD35) IgG$_1$ (final concentration 25 µg/ml), whereas the fourth group was added with rhIGFP7 (final concentration 100 ng/ml) and mouse anti-human CR1 IgG$_1$ (final concentration 25 µg/ml). Rosetting assay was conducted after the incubation. Separately, the late stage-IRBCs were sorted with MACS. The sorted cells were divided into four groups, each to be mixed with URBCs of A, B, O, and AB groups respectively. Each of the cell mixture groups was further divided into two groups, where rhIGFBP7 (final concentration 100 ng/ml) was added into one group and the other group served as control. Culture media enriched with 20% AB serum were used. The experiment was repeated with CSMT replacing rhIGFBP7.

13. Identification of Serum-Derived Co-Mediators in IGFBP7-Mediated Rosetting An aliquot of human serum used for culture medium preparation was filtered with cellulose acetate syringe filter (pore size 0.45 µm). The filtered fraction was used to prepare 20% filtered serum-enriched RPMI1640 medium. Packed erythrocytes from cultures (*P. falciparum* laboratory adapted lines: 3D7, C52-WT, FVT201, MKK183, WPP3065) were divided into two groups. The first group was suspended with 20% complete human serum-enriched RPMI 1640 (denoted as "human serum" group). The second group was suspended with the 20% filtered human AB serum-enriched medium (denoted as "filtered human serum" group). Culture was further incubated with or without IGFBP7 (100 ng/ml) before rosetting assessment.

14. Role of Von Willebrand Factor (VWF) and Thrombospondin-1 (TSP-1) in IGFBP7-Mediated Rosetting Culture suspension of the laboratory-adapted *P. falciparum* lines (3D7, MKK183, NHP1106, WPP3065, WPP2803, NHP4770, FVT201, FVT402) was centrifuged, and the packed cells were divided into groups: IGFBP7-free, anti-VWF, IGFBP7, and IGFBP7+anti-VWF groups. Rabbit anti-human VWF polyclonal IgG was used at working concentration of 25 µg/ml whereas IGFBP7 at 100 ng/ml was applied. Rosetting assay was done after incubation. In another experiment, the packed cells of parasite cultures (3D7, MKK183, NHP1106, WPP3065, WPP2803, NHP4770, FVT201, FVT402) were divided into two parts, one was suspended with 20% serum-enriched RPMl1640 whereas the other group was suspended with 2% serum-enriched RPMI 1640. Each group was further divided into four categories i.e. control, IGFBP7, VWF, and IGFBP7+VWF. The working concentration of IGFBP7 was 100 ng/ml. For rhVWF (referred as VWF), final concentration of 1 IU/ml was used. Rosetting assay was conducted after incubation. In a separate experiment, the packed cells of cultures (3D7, MKK183, NHP1106, WPP3065, NHP4770, FVT201, FVT402) were suspended with 0.25% Albumax 11 (Alb)-enriched RPMI1640, and divided into seven groups, each incubated with different concentrations of VWF (0, 0.06, 0.125, 0.25, 0.5, 1.0, 2.0 IU/ml) prior to rosetting assay.

The antibody blocking experiment using anti-VWF was repeated using mouse anti-human TSP-1 IgG$_{2B}$ in place of the anti-VWF antibody. Subsequently, experiments were conducted using rhTSP-1 (referred as TSP-1). The parasite culture packed cells were washed with plain RPMI 1640 medium twice. Each parasite line was divided into 12 groups. Ten groups were suspended with 0.25% Albumax-enriched medium (referred as "Alb" in this experiment) and the remaining two groups were suspended with 20% serum-enriched medium (referred as "20% serum" in this experiment). The groups were as follow: IGFBP7-free Alb (control), Alb+IGFBP7 (100 ng/ml), Alb+VWF (21 U/ml), Alb+10 ng/1 TSP-110 (henceforth referred as TSP-1$_{10}$), Alb+TSP-1$_{10}$+IGFBP7, Alb+TSP-1$_{10}$+IGFBP7+VWF, Alb+500 ng/ml TSP-1 (referred as TSP-1$_{500}$), Alb+TSP-1$_{500}$+IGFBP7, Alb+TSP-1$_{500}$+IGFBP7+VWF, Alb+TSP-1$_{500}$+VWF, 20% serum, 20% serum+IGFBP7. The working concentrations of IGFBP7 and VWF used were 100 ng/ml and 2 IU/ml respectively. Rosetting assay was conducted after incubation.

To quantitate VWF needed in IGFBP7-mediated rosetting, the parasite culture packed cells (3D7, MKK183, NHP1106, WPP3065, NHP4770, FVT201, FVT402) were washed with plain RPMI 1640 medium twice. Subsequently, the cells were suspended with 0.25% Albumax-RPMI. Each isolate was further divided into seven categories, each added with different concentrations of VWF (0, 0.125, 0.5, 2.0 IU/ml). All these groups were given IGFBP7 (working concentrations 100 ng/ml) and TSP-1 (10 ng/ml). Rosetting assay was conducted after incubation.

15. IGFBP7 Secretion Quantification

Peripheral monocytes (CD14$^+$) were purified from blood collected from five healthy donors via Ficoll concentration method, followed by CD14$^+$ beads purification. The purified cells were suspended in 10% FBS-enriched RPMI 1640 medium. Three wells of 96-well flat bottom microplate were allocated to cells harvested from each donor, where 10$^5$ cells were seeded into each well. One well served as plain control, whereas the other well was incubated with URBC, and the third one was incubated with the purified P. falciparum 3D7 IRBCs (monocyte:iRBC ratio=1:1,000). The cells were incubated at in vitro cultivation for 24 hours. Subsequently, supernatant of the cultures were collected separately. During supernatant collection, care was taken to minimize uptake of sedimented cells (RBCS, lysed cell products, hemoglobin may interfere with ELISA). Human IGFBP7 DuoSet® ELISA kit was used to measure the IGFBP7 level in the supernatant of each experiment group using manufacturer's protocol. Measurements were done with microplate reader Tecan i-Control) (Tecan®). The limit of detection for the ELISA kit was 39.1 pg/ml.

The steps were repeated on THP-1 cell line, with slight modifications, where five laboratory-adapted P. falciparum lines (3D7, CS2-WT, FVT201, MKK183, WPP3065) were recruited. The mature stage-IRBCs were purified, and these purified IRBCs were then added with URBCs to make cell mixtures of parasitemia 16%, 8%, 4%, 2%, 1% 0.5% and 0.25%. Packed cells of only URBCs (0% parasitemia) was used as control. The cells were added into the Lab-Tek™ 8-chamber-slides that were already seeded with respective cell lines (1×10$^5$ cells per well), making cellular suspension of 1.5% hematocrit. The cell mixtures were incubated for 24 hours under in vitro cultivation conditions. Subsequently, supernatant was collected for ELISA analysis. During supernatant collection, care was taken to minimize uptake of sedimented cells (RBCS, lysed cell products, hemoglobin etc. may interfere with ELISA). ELISA was conducted on the supernatant collected.

The P. falciparum-exposed peripheral monocytes secreted significantly more IGFBP7 than their unexposed counterparts. Of note, the levels of IGFBP7 secretion by peripheral monocytes exposed to URBCs were insignificantly different from that of the unexposed monocytes, indicating that the stimulation of IGFBP7 was attributed to the presence of IRBCs. Furthermore, THP-1 and hCMEC/D3 also increased their IGFBP7 secretions significantly after parasite exposure. Interestingly, parasitemia as low as 0.25% was adequate to significantly stimulate both cell lines to secrete more IGFBP7. Further increment in parasite density (up to 16% parasitemia) did not significantly increase the IGFBP7 secretion further.

Given that monocytes and endothelial cells increase IGFBP7 secretion upon Plasmodium exposure, could rosetting and malaria pathogenesis be linked via circulatory IGFBP7 level? Our Malawian clinical study showed that the plasma IGFBP7 levels of 17 paediatric uncomplicated falciparum malaria patients (mean 100.5±17.88 ng/ml) were significantly higher than those of paediatric cerebral malaria patients (mean 53.29±18.38 ng/ml) and uninfected controls (mean 54.59±16.80 ng/ml). Remarkably, the pathophysiological relevant levels of plasma IGFBP7 fall within the narrow dynamic concentration range of in vitro IGFBP7-stimulated rosetting. The patients with uncomplicated malaria had significantly higher levels of serum IGFBP7 than those suffering cerebral malaria (the most fatal falciparum malaria complication) and healthy controls. This provides clinical evidence for using IGFBP7 as an adjunct treatment agent in malaria treatment, to reduce or prevent progress of malaria pathogenesis into severe complications.

16. Effects of IGFBP7 on Rosetting and Cytoadhesion to hCMEC/D3

Following this we investigated the relationship between IGFBP7, rosetting and IRBC-endothelial cytoadhesion. As expected, IGFBP7 stimulated rosetting of the recruited laboratory-adapted P. falciparum. Subsequent co-incubation of these "rosette-stimulated" packed cells with the hCMEC/D3 resulted in lower rate of IRBC-endothelial cytoadhesion, as compared with their non-IGFBP7-primed counterparts. How about the already endothelial-cytoadhered IRBCs? Incubation of hCMEC/D3-cytoadhering IRBCs with IGFBP7 reduced IRBC-endothelial cytoadhesion whereas rosetting was stimulated. Clearly, presence of IGFBP7 interfered with the dynamics between IRBC-endothelial cytoadhesion and IRBC-rosetting.

Is the IGFBP7-induced reversal of IRBC-endothelial cytoadhesion mediated via the IGFBP7-stimulated rosetting? Or are the two events occurring concomitantly? Subsequent experiments demonstrated that IGFBP7 requires coexistence of both URBCs and IGFBP7 to significantly reduce IRBC-endothelial cytoadhesion. Interestingly, for all parasite lines recruited, the rosetting rates of IRBCs detached from hCMEC/D3 after co-incubation with URBCs and IGFBP7 were not very high (5-25%). This suggests that IGFBP7-induced reversal of IRBC-endothelial cytoadhesion happens independently of 18 IGFBP7-induced rosetting. The two events are likely to happen in parallel instead of being a cause-effect relationship.

17. Knockdown of IGFBP7 Expression by THP-1 Using RNAi

THP-1 cells were thawed and cultured with RPMI1640 medium enriched with 10% FBS. 96-well plate was used. Each recruited well was seeded with $1\times10^4$ cells. For each well, 110 μl of medium and hexadimethrine bromide (final concentration 8 μg/ml; to enhance transduction) were added. Lentiviral transduction particles to knock down expression IGFBP7 (hPGK-Puro_CMV-tGFP; SHCLNV-NM_001553) were added (MOI 3) based on formulas provided in the kit's user guide. The cells were centrifuged at 1000 g for 60 minutes. In the following day, the medium containing lentiviral particles were removed, and replaced with fresh medium. Care must be taken not to aspirate the cells. The next day, the transduced cells were cultivated with puromycin-added medium (working concentration 3 μg/ml) for selection. A small aliquot of the cells were examined with epifluorescence microscope to check the GFP expression. The cells were used as "IGFBP7-knock down (KD) THP-1" in subsequent experiments.

Late stage-IRBCs (*P. falciparum* lines 3D7, CS2-WT, FVT201, MKK183, WPP3065) were purified. The WT- and IGFBP7-KD THP-1 were used. For each cell types, two groups (each group contains five sets) were prepared. One was added with the purified IRBCs (THP-1 to IRBC ratio of 1:1000) and the other one was added with URBCs from five healthy donors (control). RPMI enriched with 1% serum (to keep the viability of cells long enough for the experiment while minimizing the confounding effect on the protein quantification by the IGFBP7-KD cells) was used. The cells were incubated for 18 hours at in vitro cultivation conditions. The supernatant of the cells was collected. Care must be taken to avoid uptake of cell/cell debris. The supernatant was used for IGFBP7 quantitation using ELISA and subsequent experiment described below.

The parasite culture packed cells (*P. falciparum* lines 3D7, CS2-WT, FVT201, MKK183, WPP3065) were divided into four groups. The first well was exposed to 1×PBS (negative control), the second group was exposed to 100 ng/ml IGFBP7 (positive control), the third group was added with similar volume of culture supernatant collected from the IGFBP7-KD-THP-1 exposed to URBCs (CSKD-U), and the fourth group was added with culture supernatant collected from the IGFBP7-KD-THP-1 exposed to IRBCs (CSKD-I). The suspension was topped up with 20% serum-enriched medium and incubated for one hour prior to rosetting assay.

18. Phagocytosis Assessment

THP-1 is cultivated and expanded into three batches. For each batch of culture, $1\times10^6$ cells were incubated with IGFBP7 (working concentration 100 ng/ml) for one hour at in vitro cultivation conditions. Another set of cells acted as IGFBP7-free control. Subsequently, Zymosan A (working concentration 10 μg/ml) was added to both sets of cells and incubated for another one hour at in vitro cultivation conditions. Supravital staining with Giemsa was done for 15 minutes following this. Using wet mount technique, the percentage of THP-1 cells which has engulfed Zymosan A was determined as phagocytosis rate by recruiting 1,000 THP-1 cells. The experiment was repeated with the other two batches of THP-1 culture. And all the steps were repeated for another two times using THP-1 cultures thawed at different time points. *P. falciparum* lines (3D7, MKK183, FVT402, FVT201, CS2_WT) were incubated with or without IGFBP7 in serum-enriched medium prior to rosetting assay. Subsequently, THP-1 were added. Using wet mount technique, the IRBC phagocytosis rates were determined following the same formula to determine phagocytosis rate in the Zymosan A experiment. Prior to this, an experiment to compare IRBC phagocytosis activity of THP-1 and peripheral monocytes was conducted with a *P. falciparum* line (NHP1106), THP-1 and CD14+ peripheral monocytes from healthy donors, using steps described above (five biological replicates conducted).

19. Statistical Analyses

GraphPad Prism 7.0 was used for data analysis. For normally distributed data (Shapiro-Wilk normality tested), paired t-test was conducted for pairwise comparison. Matched measurement comparison for non-normally distributed datasets was done using Friedman test with Dunn's multiple comparison test. To compare two sets of non-normally distributed data, Mann-Whitney test was used. One-way ANOVA tests were conducted for grouped data set comparison. For normally distributed dataset, Tukey's test was applied for multiple group comparisons. Dunnett's test was used to compare groups against a control. Two-way ANOVA was used to study the effect of multiple experiment conditions on rosetting in different parasite lines, each with different culture batches. P values<0.05 were interpreted as statistically significant.

In Vivo Experiments and Data

Here, we set out to determine the effect of IGFBP7 administration on mice. In particular, we set out to determine the dose and protection from ECM death of mouse IGFBP7 administered i.v. on days 5-12 post-infection (dpi) to *Plasmodium berghei* ANKA line expressing luciferase (PbAluc) infected C57BL/6 mice.

1. Materials

C57BL/6 (~5 wo), parasite PbAluc, recombinant mouse IGFBP7 (R&D systems), Accu-Chek Performa 100 blood glucose Test Strips.

2. Methods (a). rmIGFBP7 Suspension

IGFBP7 was suspended in 1×PBS (concentrations: 0, 50, 100, 200, 1000, and 5000 ng/ml). A separate aliquot of IGFBP7 (5000 ng/ml) was prepared and boiled for one hour, to be used as control.

For each protein concentration group, I.V. administration of 100 μl per mouse was done.

(b). Mouse Infection

Mice were infected with PbAluc. Prior to infection, an aliquot of serum was collected for each mouse using blood collected through orbital bleeding. Sera were also collected on days 3 and 6 post-infection (dpi) for further testing in future.

A few mice were used as uninfected control.

Peripheral parasitemia of each infected mouse was monitored with flow cytometry from 4 dpi.

Only mice with similar progress of parasitemia and similar demonstration of signs prior to IGFBP7 administration were recruited for the experiment (e.g. mice that were already in paralysis state on 5 dpi were not recruited, mice whose parasitemia were either too low or too high were excluded).

(c). Administration of rmIGFBP7

I.V. administration was done on daily basis from 5-12 dpi. The n number for each concentration group was 8 except group 5 ng/mouse (n=7) and group 500 ng/mouse (n=5).

(d). Blood Glucose Quantification

On 4 dpi, the "before treatment" profiling was done whereas the "after treatment" profiling was done two hours after administration of rmIGFBP7. For each concentration, 5 mice were recruited for profiling. For the uninfected mice, 3 mice were recruited as uninfected, untreated controls, and 5 mice were recruited as uninfected control treated with 100 ng/mice IGFBP7.

The edge of the commercial test kit strip was exposed to the blood at the mouse tail. blood will move up by capillary mechanism. The readings were recorded.

It is important to note that the mice should be exposed to minimal stress. Isofluorane should not be used prior to the measurements. As blood from retro orbital and those exposed to anesthetic gas will have higher blood glucose levels, only blood from tail bleeding when the mice are conscious is used for this assay.

(e). Monitoring the Mouse's Survival

The mice were monitored daily, and their signs and symptoms were observed. Dead mice were removed.

Survival of mice within the experimental cerebral malaria (ECM) period (6-12 dpi) across the experimental groups was recorded.

Mice that survived the ECM period were monitored until their death by malaria-induced anemia.

3. Results (a). Effect of IGFBP7 on Blood Glucose Level of Uninfected Mice

Administration of IGFBP7 (100 ng/mice) did not significantly alter the blood glucose level of uninfected mice (One way ANOVA with Kruskal-Wallis test).

Figure 14:
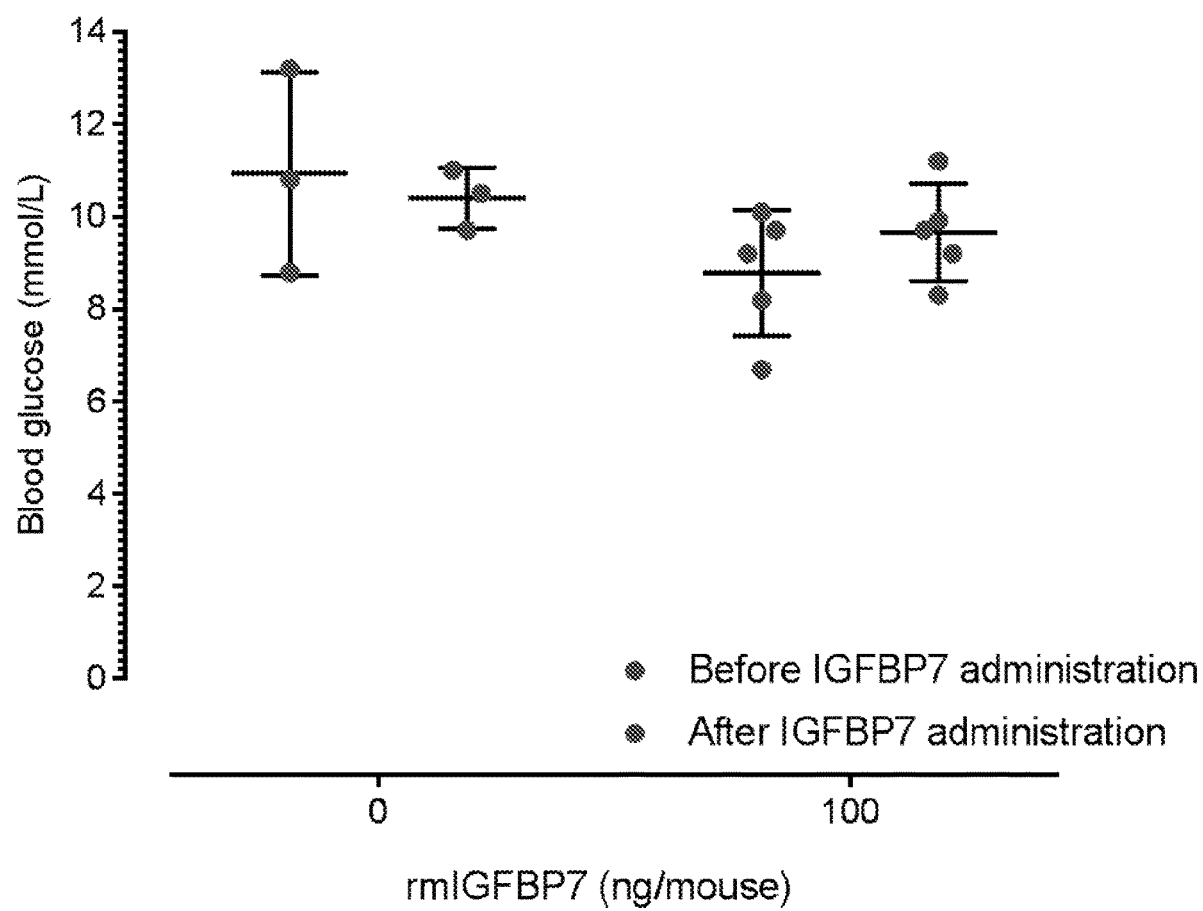

FIG. 14 shows blood glucose levels of uninfected mice before and two hours after injection of IGFBP7. Untreated controls were included. No significant differences noted from comparison across the groups.

Subsequently, the experiment was repeated with infected mice, using IGFBP7 of different working concentrations. No significant difference noted across the groups (two-way ANOVA with Tukey's multiple comparison test).

Figure 15:
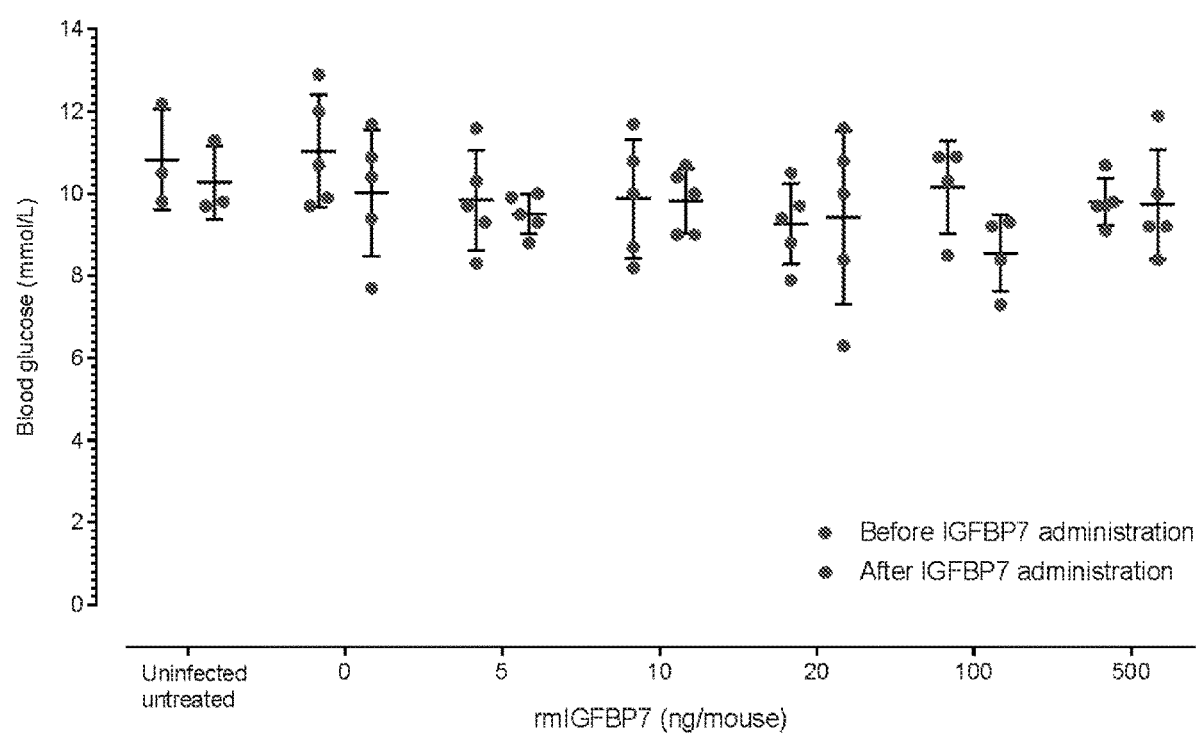

FIG. 15 shows blood glucose level of PbAluc-infected mice before and two hours after administration of IGFBP7. Uninfected, untreated control was recruited as a control. No significant changes noted across all groups (two-way ANOVA with Tukey's multiple comparison test).

Administration of IGFBP7 as high as 500 ng/mouse did not significantly alter blood glucose level of PbAluc-infected mice.

(b). Parasitemia Monitoring

Figure 16:
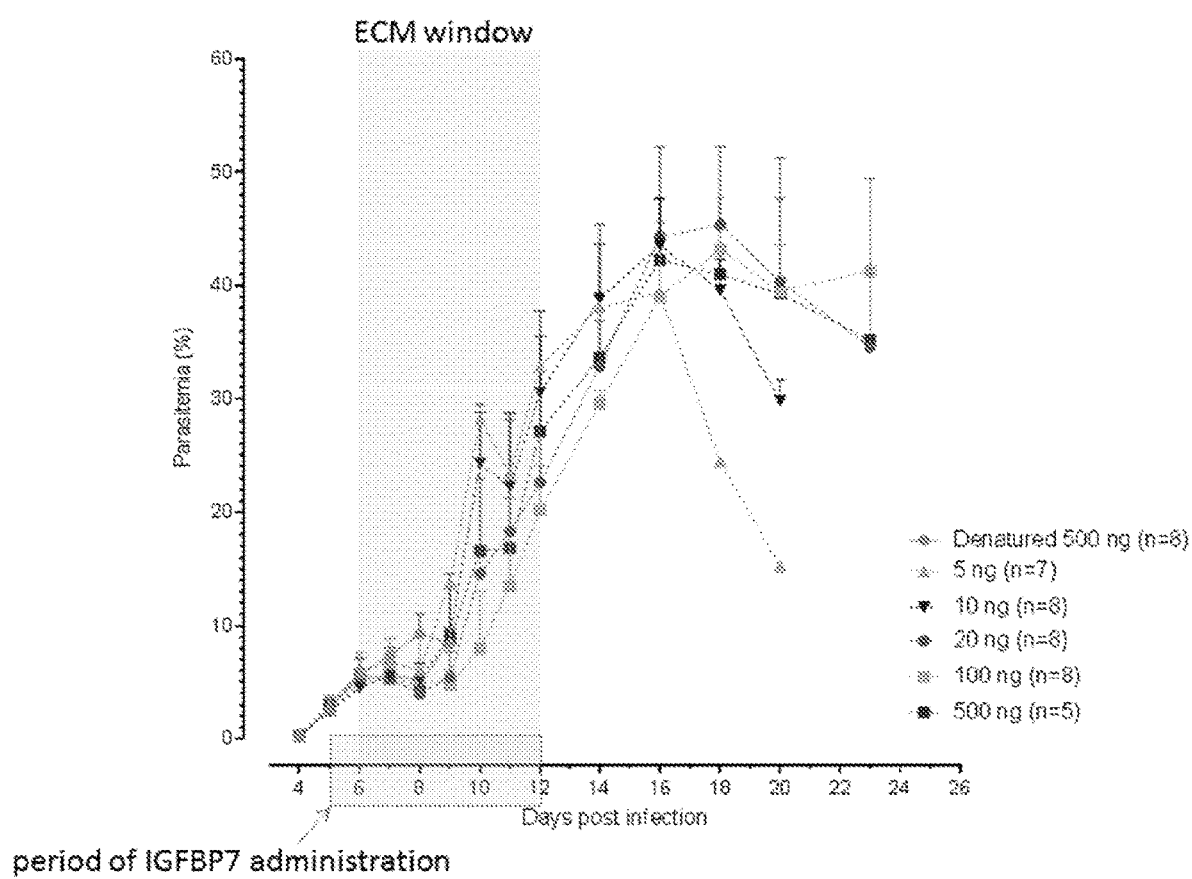

FIG. 16 shows the progress of peripheral parasitemia of infected mice from 4 dpi till 25 dpi. The region in turquoise box represents the window of ECM, where death happened within this period is attributed to cerebral malaria, in parallel with the symptoms observed on the mice. The yellow box represents duration of IGFBP7 administration.

Figure 17:
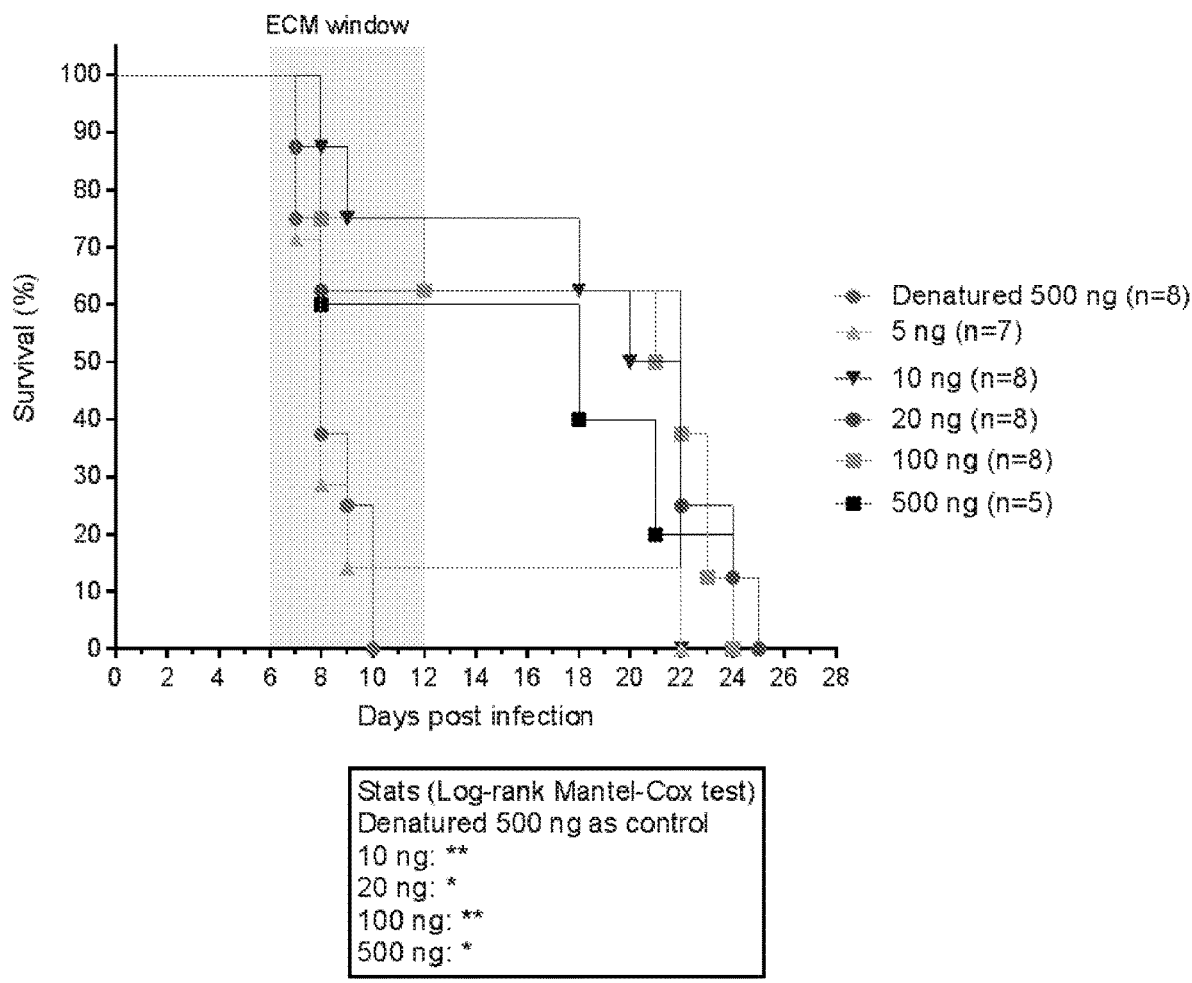

FIG. 17 shows survival curve of infected mice till 25 dpi. The region in turquoise (shaded) box represents the window of ECM, where death happened within this period is attributed to cerebral malaria, in parallel with the symptoms observed on the mice. When compared with the control (treated with denatured 500 ng/mouse IGFBP7), significant difference in survival rate was recorded for groups treated with 10, 20, 100 and 500 ng/mouse (Log-rank Mantel-Cox test P values=0.0025, 0.0235, 0.0032 and 0.0403 respectively).

Figure 18:
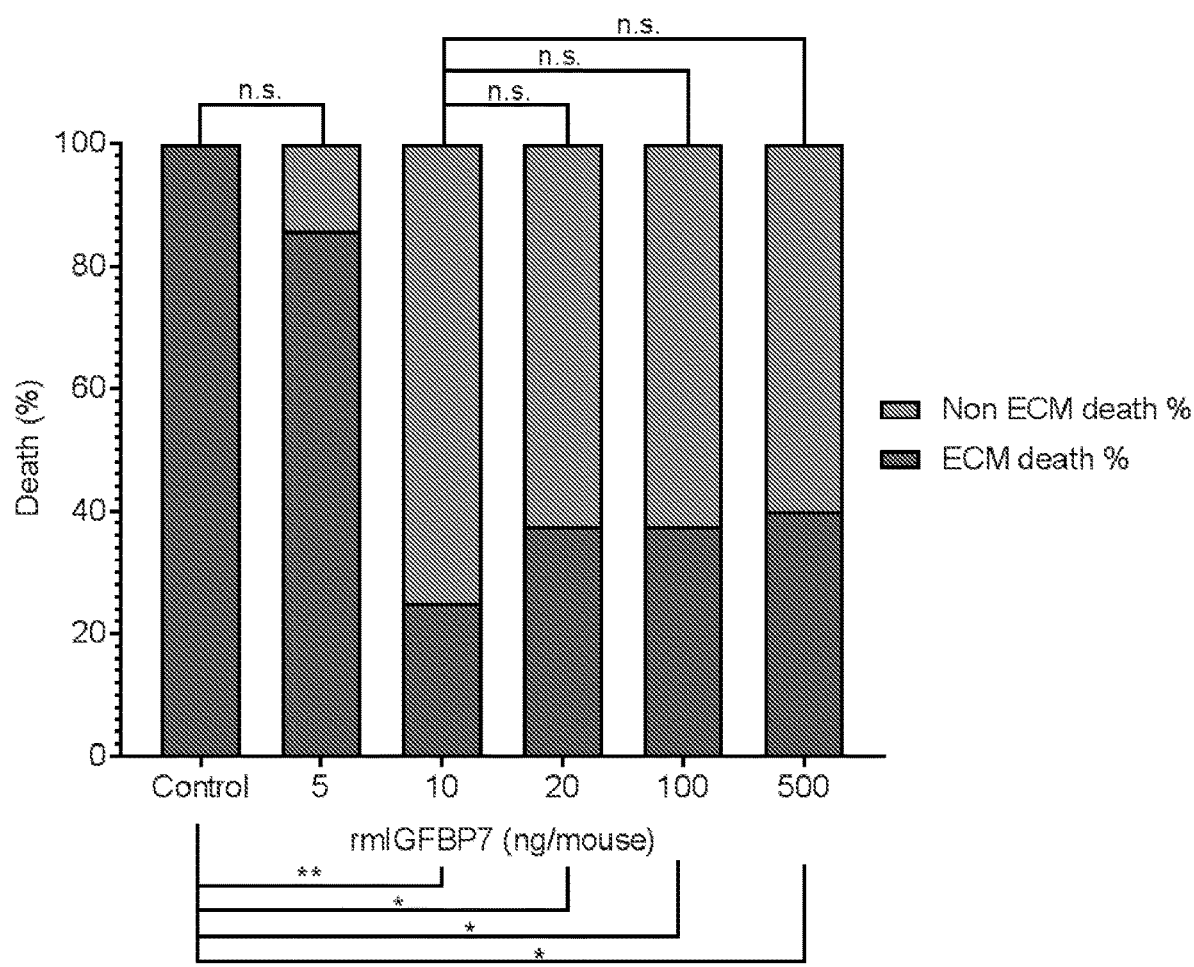

FIG. 18 shows eventual fate of deaths for mice from different experimental groups. Red bars represent fraction of population died of ECM whereas the green bars represent fraction of population died of non-ECM complications. When compared with the control group (treated with denatured IGFBP7), the groups treated with IGFBP7 of 10, 20, 100, and 500 ng/mouse showed significantly lower ECM death (Exact Fisher test P=0.007, 0.0256, 0.0256 and 0.035 respectively).

On 5 dpi, prior to administration of IGFBP7, the infected mice showed affected sense of balance, marking the early signs of cerebral malaria development.

On 6 and 7 dpi the conditions of most mice (untreated control & treatment groups) worsened, with some showing paralysis. From 7 dpi, deaths were noted.

After 8 dpi, mice from the IGFBP7 treatment groups 10, 20, 100 and 500 ng/mouse showed reversal of CM signs and signs (severe compromise of balance control, paralysis etc). The mice were able to move around normally.

IGFBP7 as low as 10 ng/mouse is adequate to confer protection to the mouse from cerebral malaria.

Due to lack of anti-malarial intervention in this experiment, mice that survived ECM continued to have increasing parasitemia, eventually died of other malaria-induced complications such as severe anemia.

4. Conclusion

The experiments and results show that the administration of IGFBP7 for a period of 8 days before the onset of ECM significantly reduces the ECM deaths of mice.

Results

1. Effects of Human Leukocytes on Rosetting

Figure 1D:
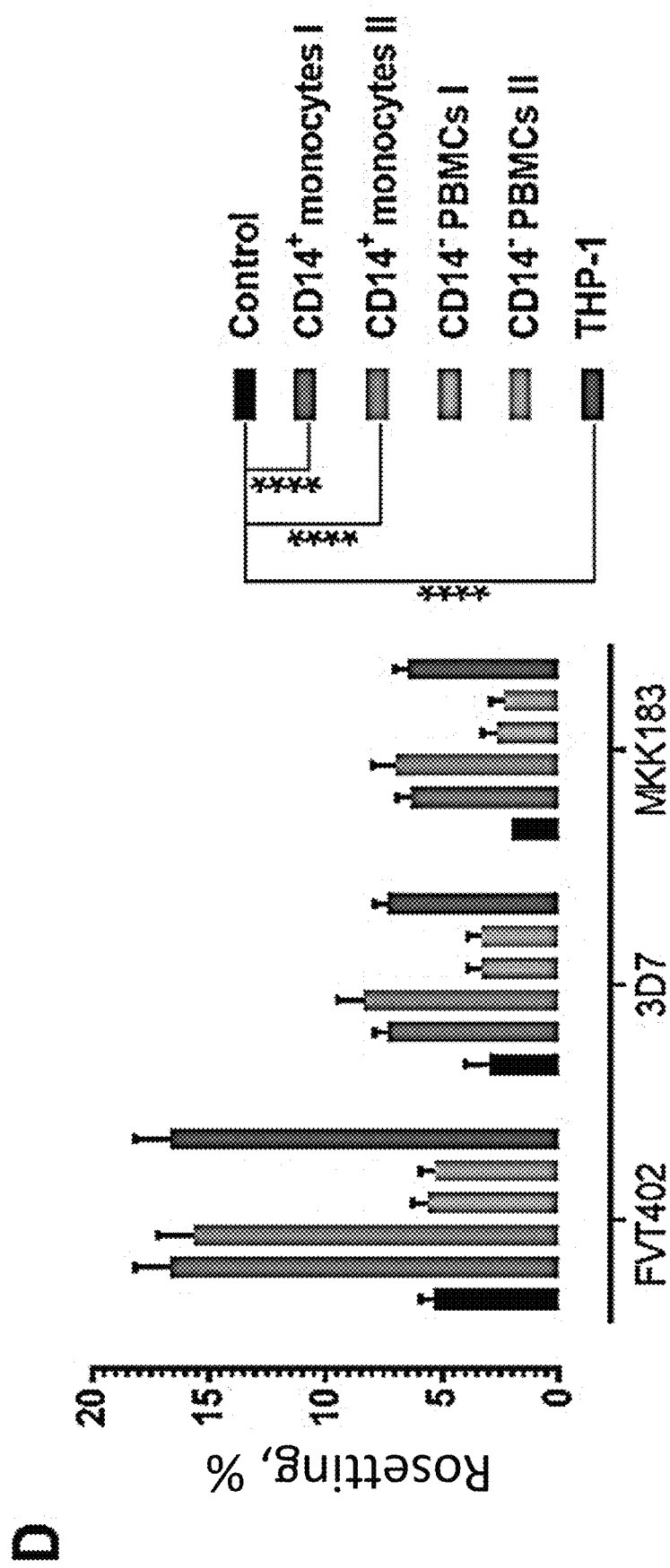
Figure 1E:
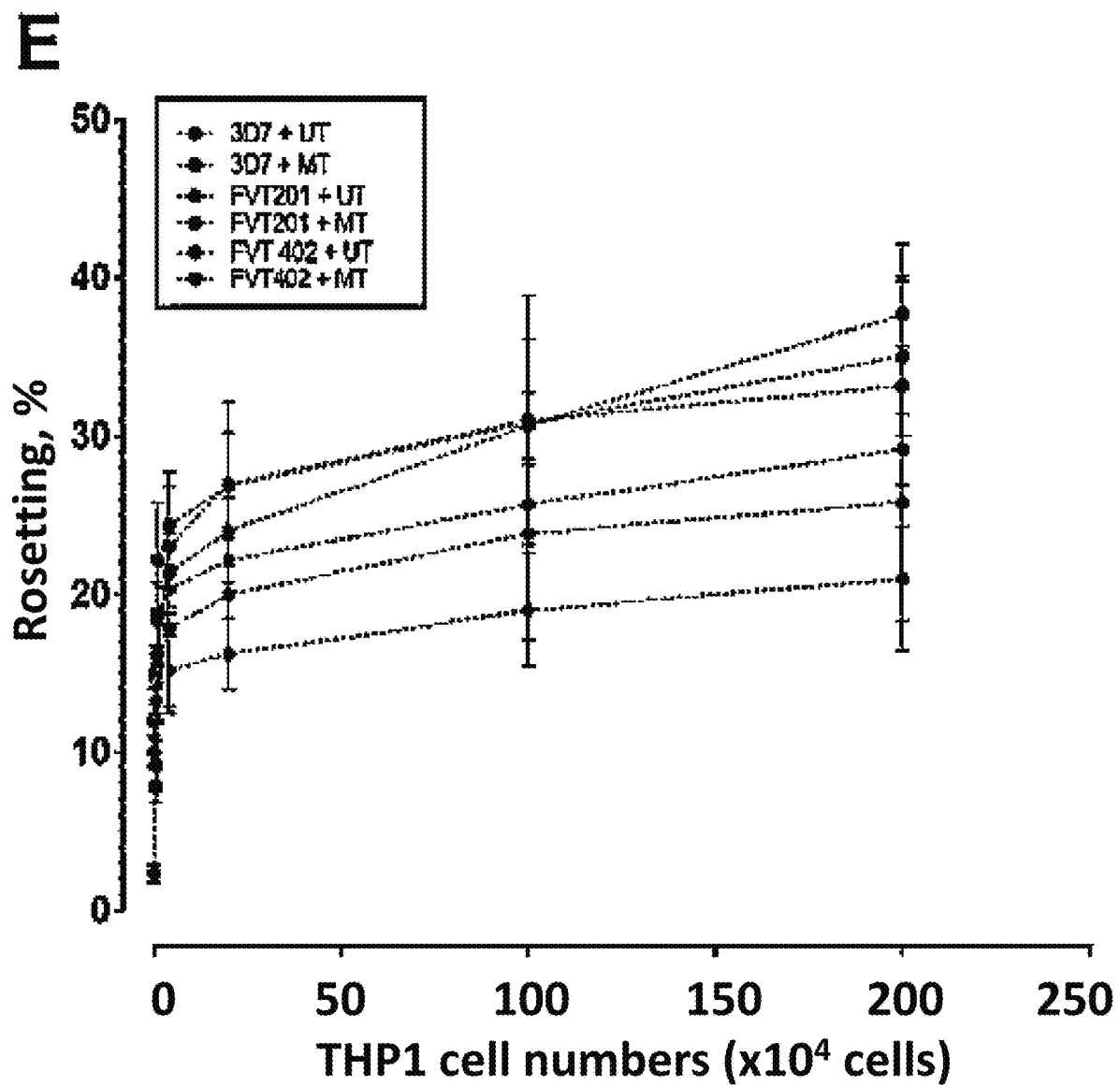
Figure 1F:
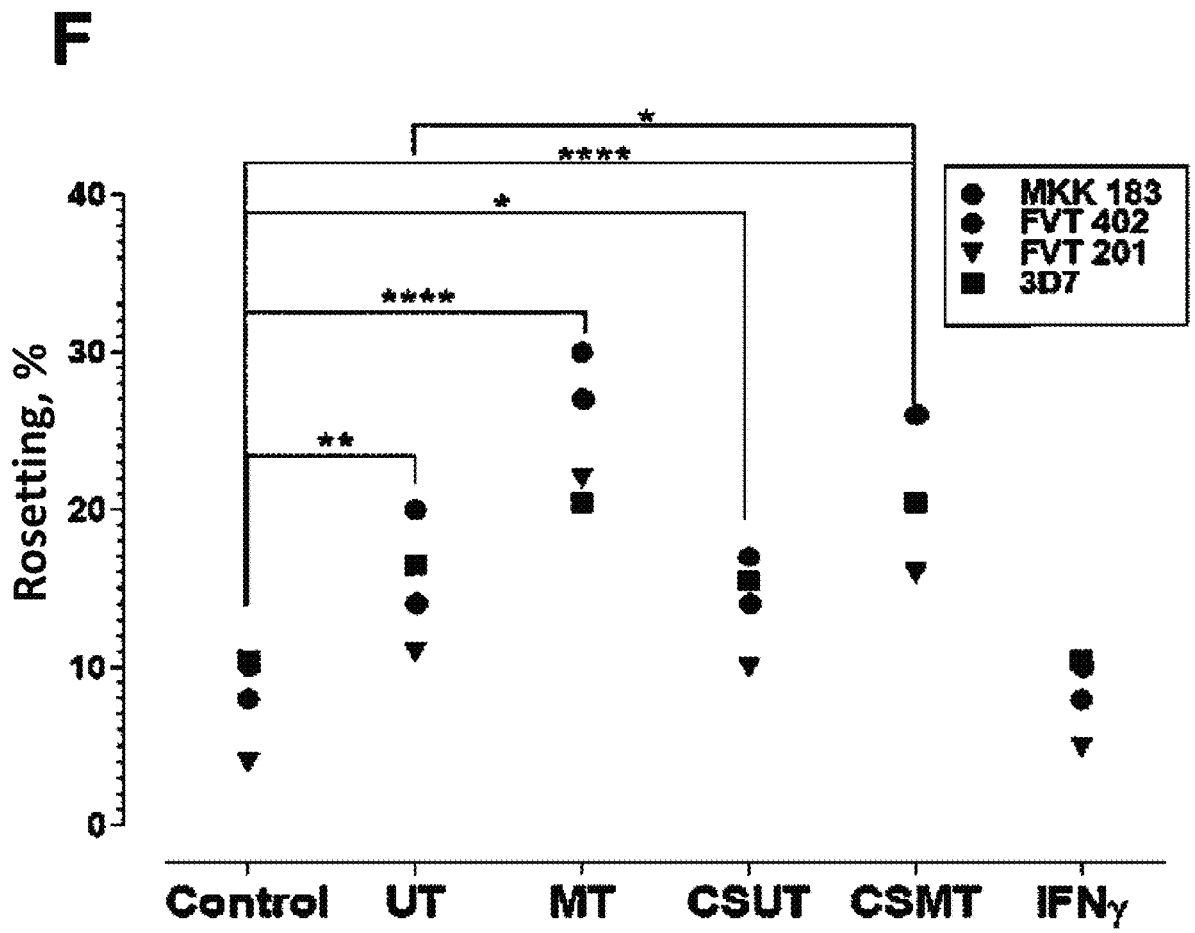

*P. falciparum*- and *P. vivax*-IRBC formed rosettes (FIG. 1A, top panel) in the presence of 20% autologous human serum and the extent of rosetting at baseline is variable depending on the parasite isolates9. When autologous blood leukocytes were incubated with clinical isolates, the rosetting rate increased by 10-40% depending on individual isolates for both parasite species (FIG. 1B). This effect was mediated primarily by monocytes (FIG. 1C). To exclude donor variability as a confounding factor, we repeated the experiment with THP-1 cell line, which is derived from the peripheral circulation of an acute monocytic leukaemia patient 19. The rosette-stimulation mediated by THP-1 was similar to that of peripheral monocytes (FIG. 1D and see Table 7). Addition of undifferentiated THP-1 (UT) and macrophage-like THP-1 (MT) increased rosetting rates in a dose-dependent manner. MT were more potent than UT, where the difference increased with the number of cells added (FIG. 1E).

TABLE 7

Raw data (rosetting rates, %) for the data set presented in bar graph (1D). R = biological replicate (same parasite line, but different flasks of cultures, using the same URBCs and culture media).

| P. falciparum lines | Control | | | CD14+ monocytes I | | | CD14+ monocytes II | | | CD14+ PBMCs I | | | CD14+ PBMCs II | | | THP-1 | | |
|---|---|---|---|---|---|---|---|---|---|---|---|---|---|---|---|---|---|---|
| | R1 | R2 | R3 | R1 | R2 | R3 | R1 | R2 | R3 | R1 | R2 | R3 | R1 | R2 | R3 | R1 | R2 | R3 |
| PVT402 | 5.0 | 5.0 | 6.0 | 15.0 | 17.0 | 13.0 | 14.0 | 16.0 | 17.0 | 6.0 | 6.0 | 5.0 | 5.0 | 6.0 | 5.0 | 18.0 | 17.0 | 15.0 |
| 3D7 | 3.0 | 4.0 | 2.0 | 7.0 | 8.0 | 7.0 | 7.0 | 9.0 | 9.0 | 3.0 | 3.0 | 4.0 | 3.5 | 4.0 | 3.0 | 8.0 | 7.0 | 7.0 |
| MKK183 | 2.0 | 2.0 | 2.0 | 6.0 | 6.0 | 7.0 | 7.0 | 8.0 | 6.0 | 2.0 | 3.0 | 3.0 | 2.0 | 3.0 | 2.0 | 6.5 | 7.0 | 6.0 |

2. Effect of THP-1 Culture Supernatants and Supernatant Fractionation

Figure 2A:
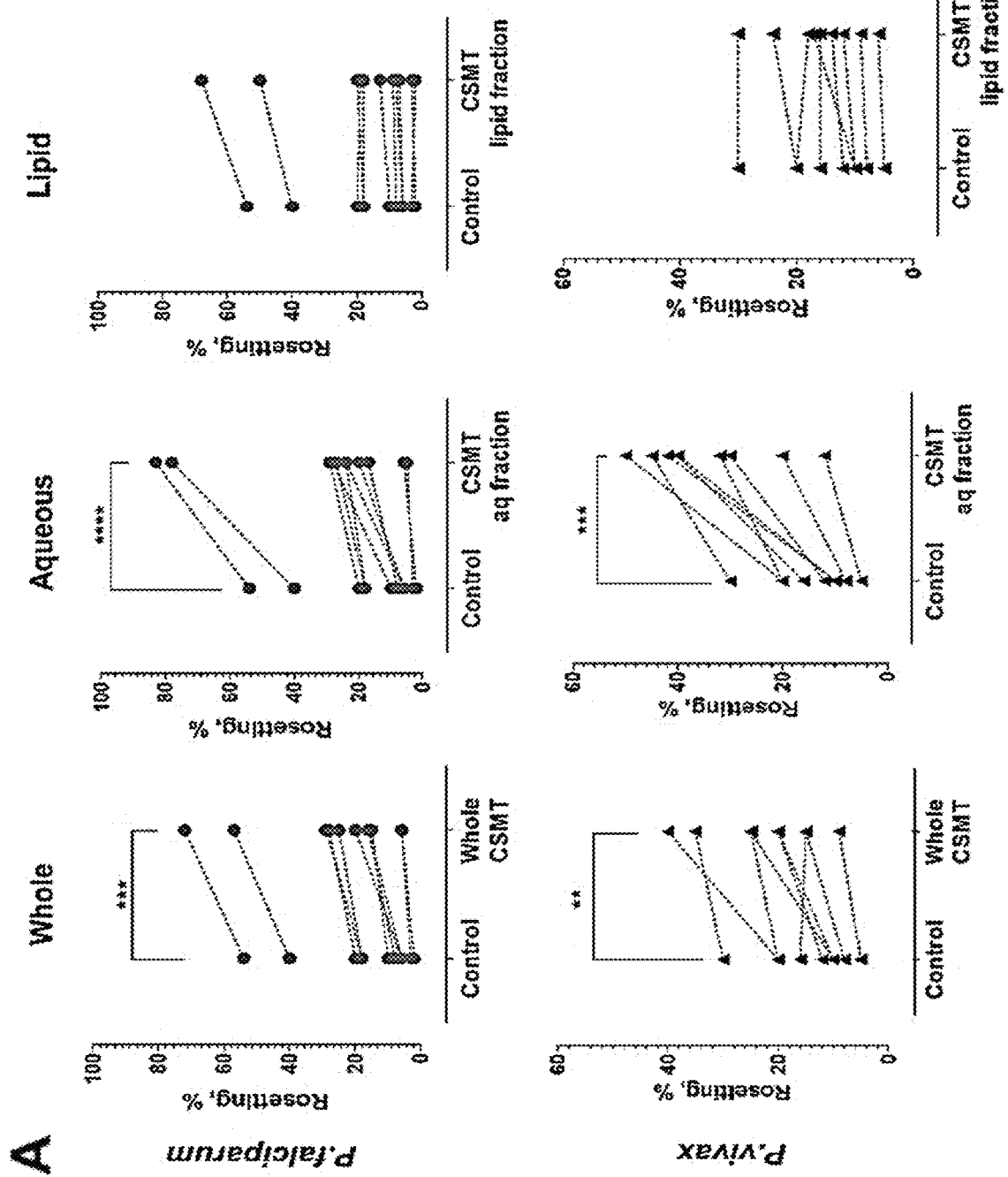
Figure 2B:
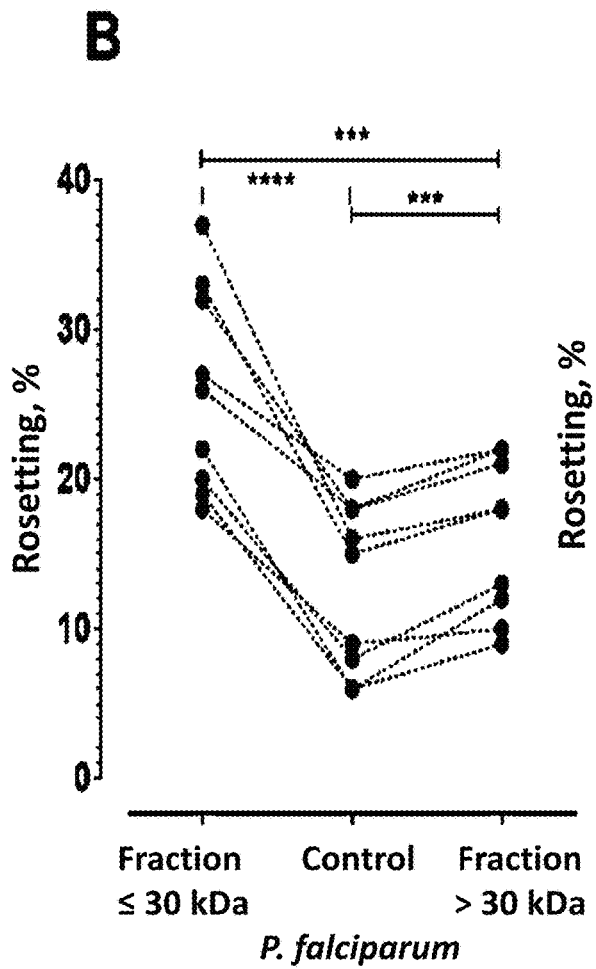
Figure 2C:
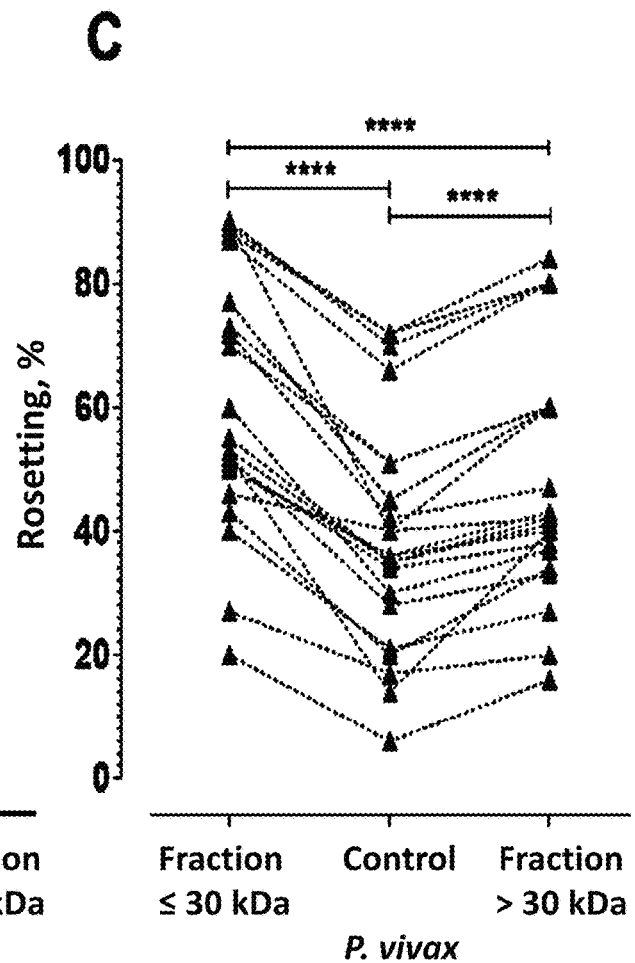
Figure 2D:
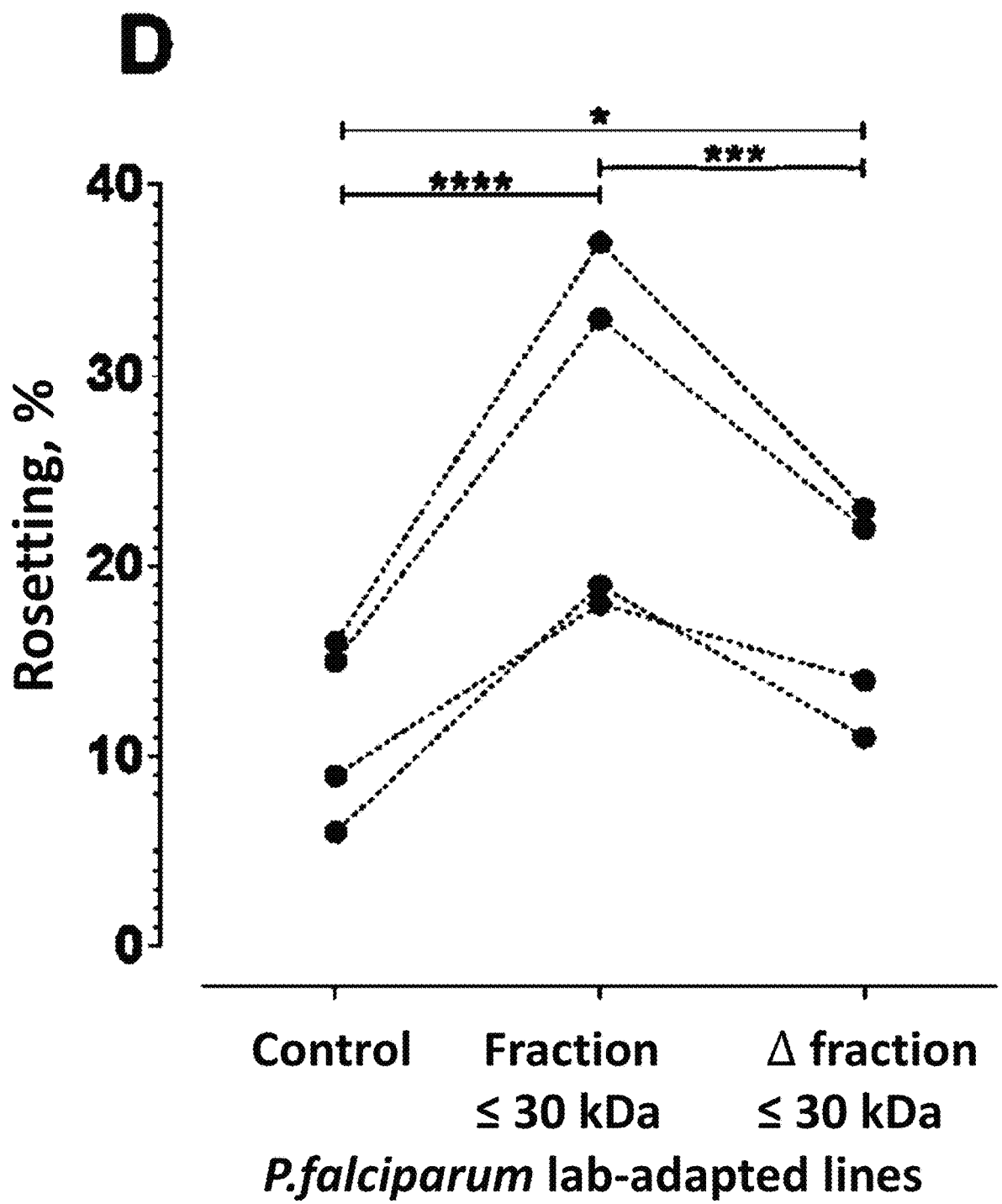

Culture supernatants (CS) of both THP-1 cell types showed similar rosette-stimulation effect, (FIG. 1F) with CSMT exerting a higher degree of rosette-stimulation than CSUT. Fractionation of CSMT into aqueous and lipid fractions revealed that the rosette-stimulating factors were in the aqueous fraction (FIG. 2A). Subsequently, we further fractionated the aqueous fraction into high and low molecular weight sub-fractions (with the cut-off of 30 kDa). Both aqueous sub-fractions induced rosetting of *P. falciparum* and *P. vivax* (FIGS. 2B and 2C), demonstrating that the rosetting stimulation was mediated by multiple secreted hydrophilic factors, predominantly of sizes 30 kDa (particularly for *P. falciparum*). Heating of CSMT's≤30 kDa aqueous fraction at 56° C. for one hour did not completely abolish its rosette-stimulating effect (FIG. 2D), indicating the presence of heat-stable factors. To further investigate the potential stimulating factors, mass spectrometry analysis was performed on this fraction. We identified 694 proteins (Table 1), of which complement factor D (CFD), insulin-like growth factor binding protein 7 (IGFBP7), nidogen 1 (NID1), hyaluronan-binding protein 2 (HABP2), and periostin (OSF2) were shortlisted (see Table 2). Apart from having high scores in the mass spectrometry analysis (Table 1), these molecules were selected because they are secreted proteins and possess cell adhesion-related properties associated with pathological changes such as vascular injuries, inflammation, cancer development, and leukocyte recruitment.

TABLE 1

Shortlisted candidates from a list of 694 compounds identified by mass spectrometry.

| Name | Score A (3, 6) | Coverage A (3, 6) | #Peptides A (3, 6) | Σ# unique peptides | #PSM A(3, 6) |
|---|---|---|---|---|---|
| Insulin-like growth factor-binding protein 7 (IGFBP7) | 175.31 | 17.56 | 6 | 6 | 7 |
| Complement factor D (CFD) | 59.50 | 8.70 | 1 | 1 | 1 |
| Nidogen 1 (NID1) | 312.18 | 8.35 | 8 | 8 | 17 |
| Hyaluronan-binding protein 2 (HABP2) | 18.08 | 8.21 | 2 | 2 | 2 |
| Periostin (POSTN) | 65.82 | 5.32 | 5 | 1 | 8 |

TABLE 2

Shortlisted candidates from a list of 694 compounds identified by mass spectrometry.

| Name | Score A (3, 6) | Coverage A (3, 6) | #Peptides A (3, 6) | Σ# unique peptides | #PSM A(3, 6) |
|---|---|---|---|---|---|
| Insulin-like growth factor-binding protein 7 (IGFBP7) | 175.31 | 17.56 | 6 | 6 | 7 |
| Complement factor D (CFD) | 59.50 | 8.70 | 1 | 1 | 1 |
| Nidogen 1 (NID1) | 312.18 | 8.35 | 8 | 8 | 17 |
| Hyaluronan-binding protein 2 (HABP2) | 18.08 | 8.21 | 2 | 2 | 2 |
| Periostin (POSTN) | 65.82 | 5.32 | 5 | 1 | 8 |

3. Antibody Neutralisation Assay

Antibody neutralisation of IGFBP7 significantly reduced (by ~40%) the rosette-stimulation by CSMT for both parasite species (FIG. 3A). Rosette-stimulation by CSMT was also reduced by anti-CFD (FIG. 3B) and anti-OSF2 (FIG. 3C) antibodies, albeit to a lesser extent. Antibodies against NID1 (FIG. 3D) and HABP2 (FIG. 3E) had no effect on CSMT-mediated rosette-stimulation. Since anti-IGFBP7 had the largest inhibitory effect, further experiments focused on IGFBP7.

4. Effect of IGFBP7 on Rosetting

Figures 4A, 4B:
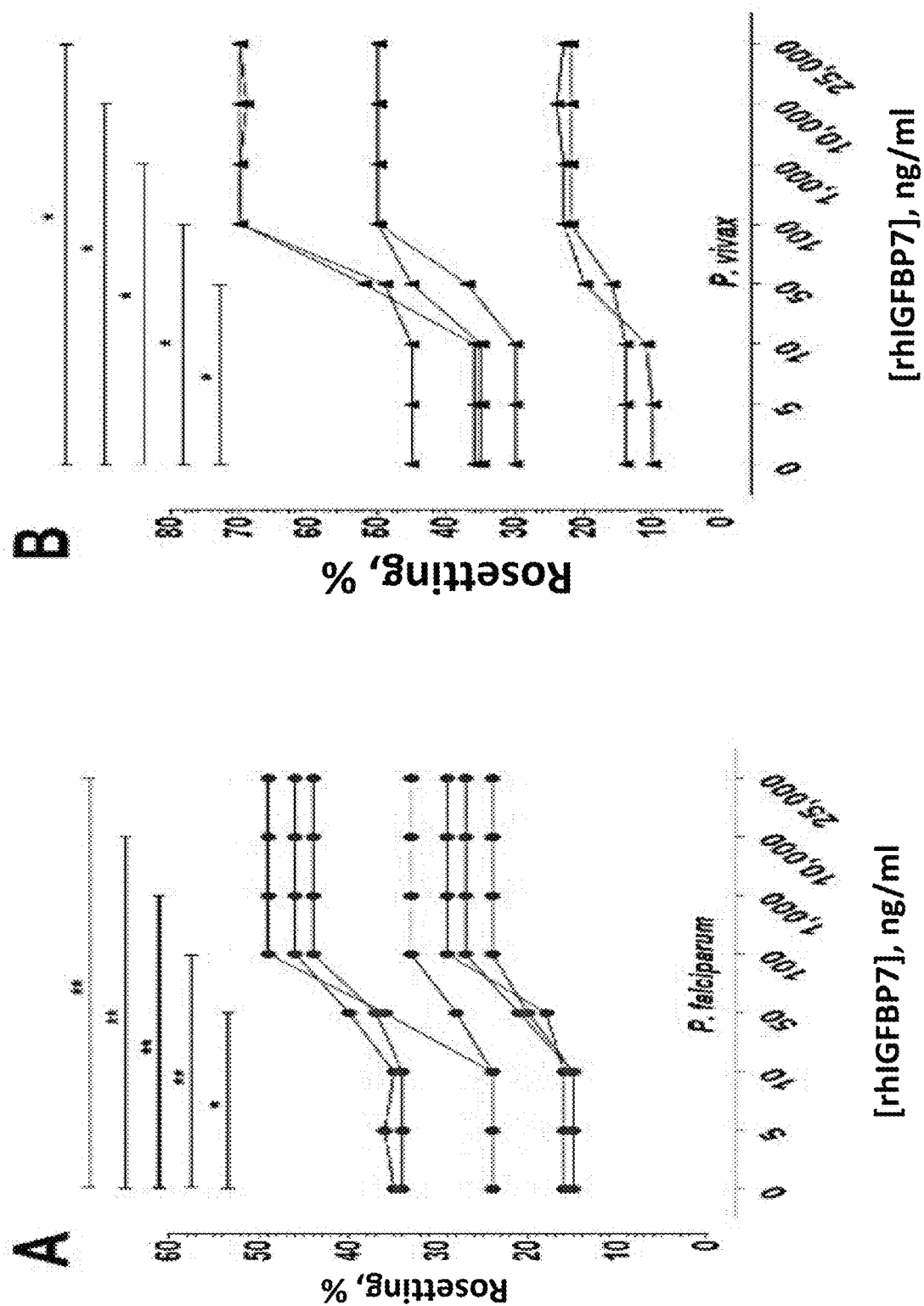
Figures 4C, 4D:
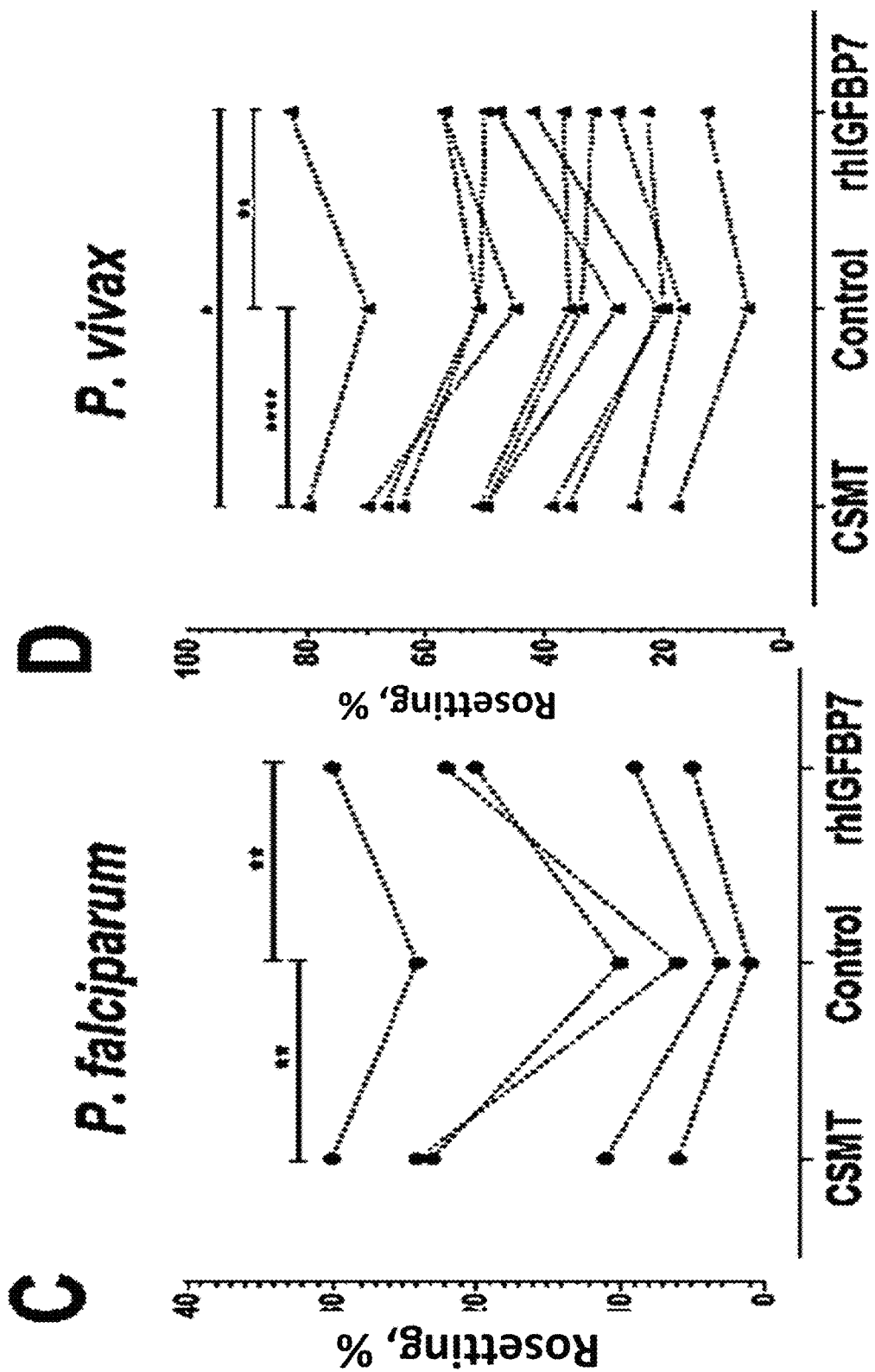
Figures 4E, 4F:
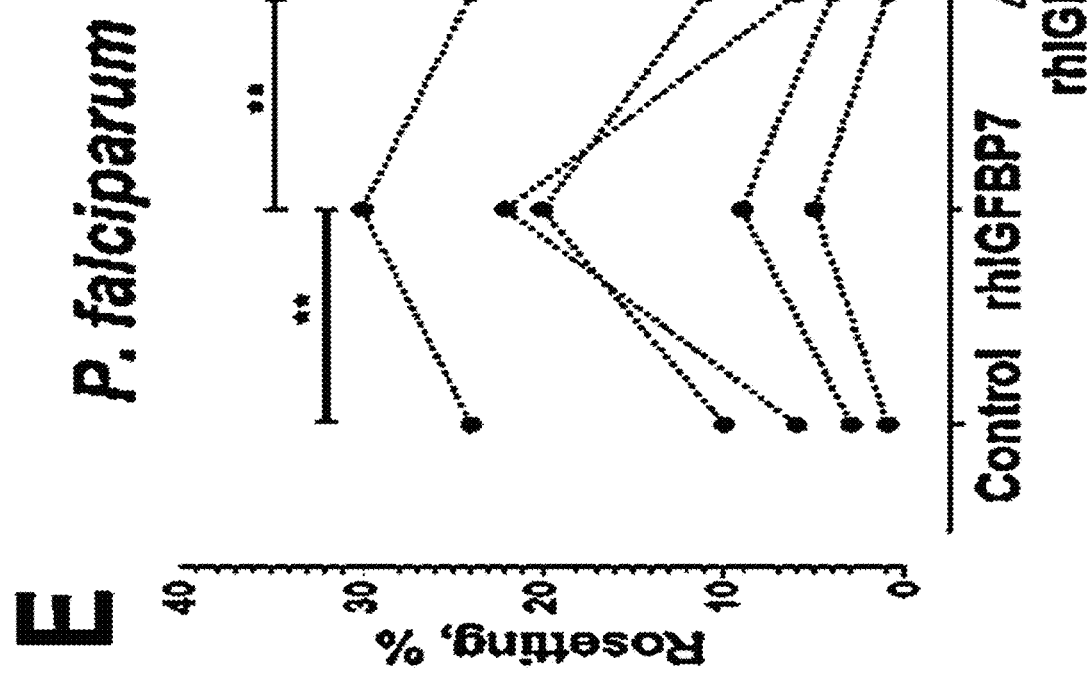
Figure 4G:
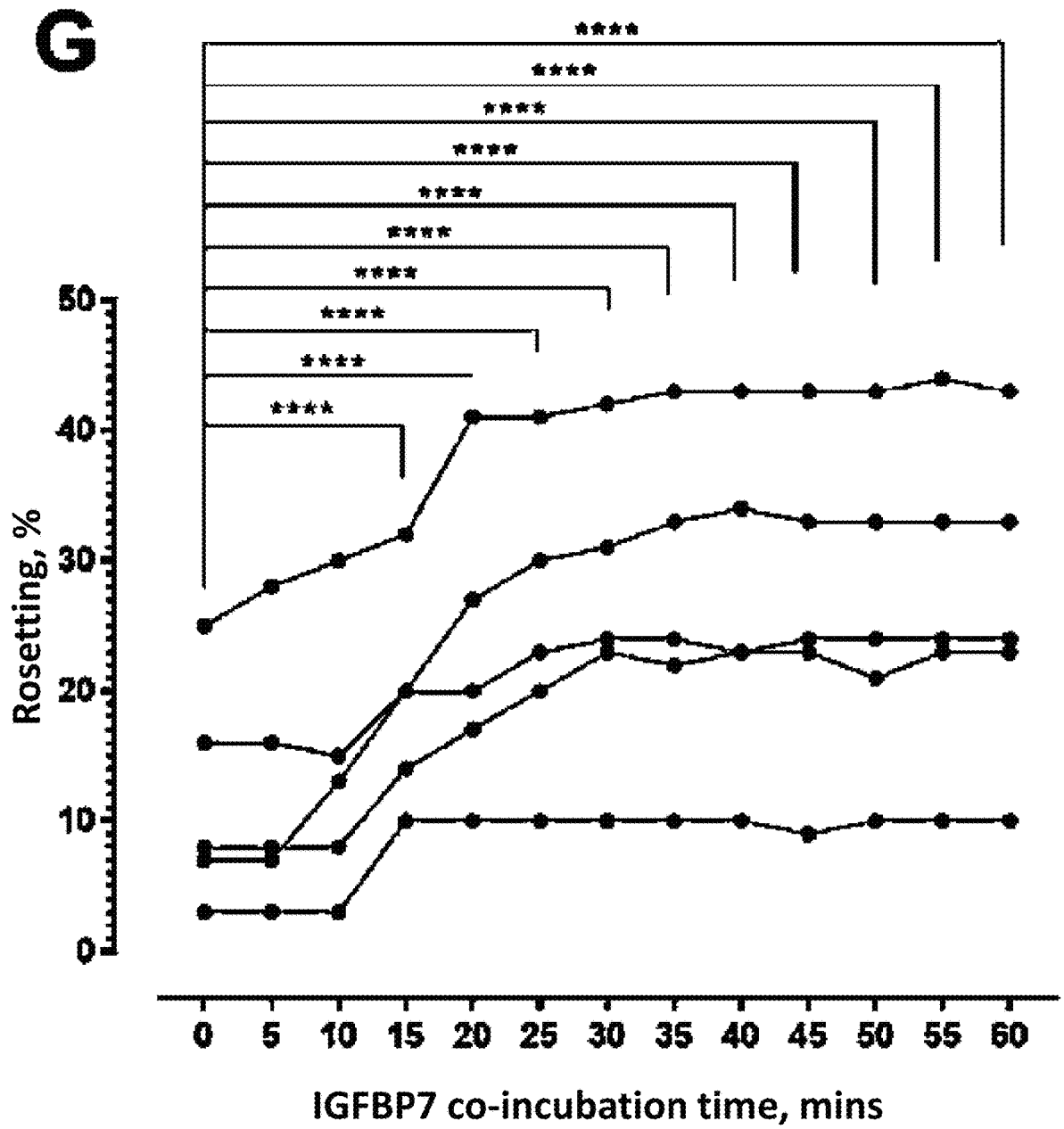
Figure 4H:
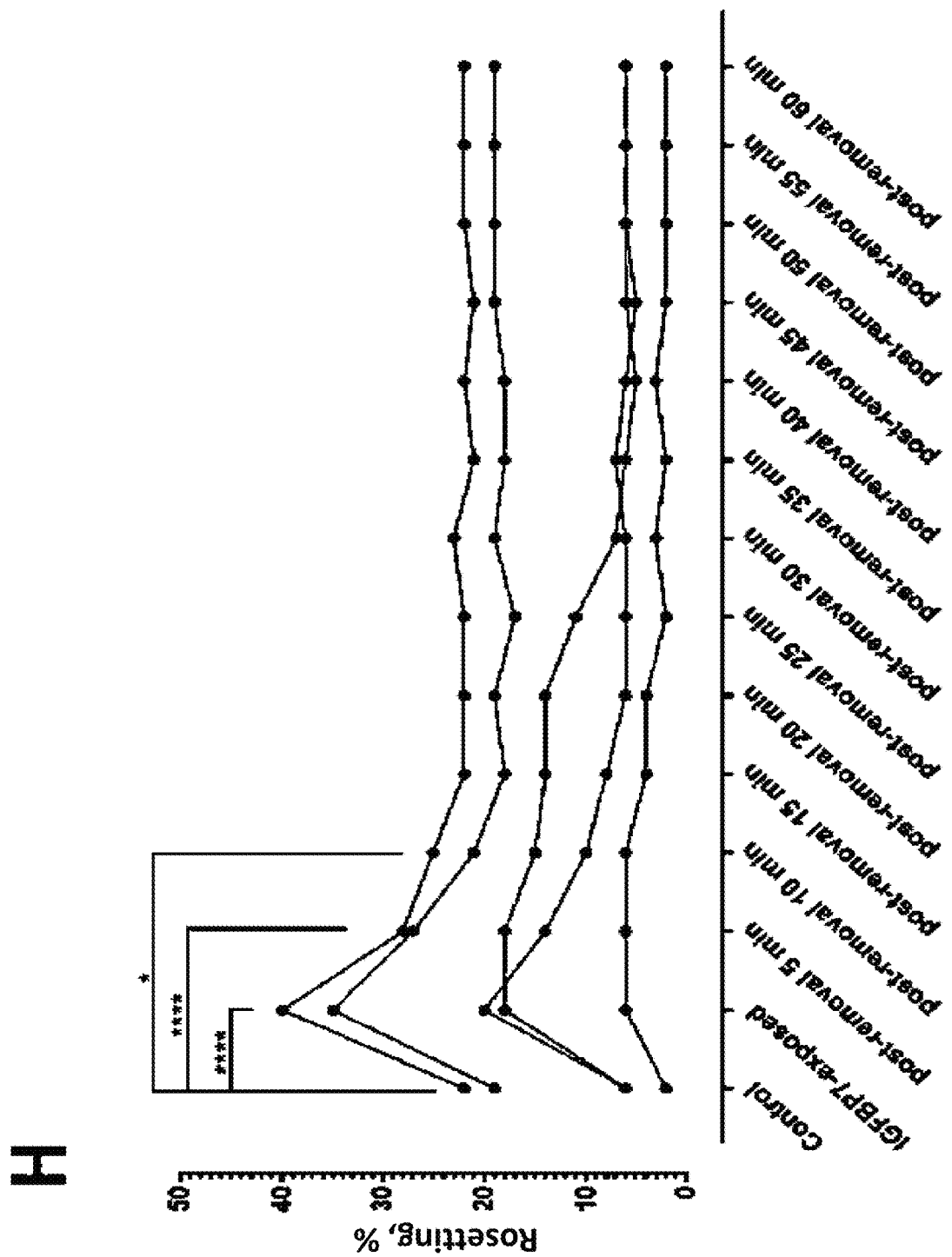

Addition of human recombinant IGFBP7 to leukocyte-free parasite culture stimulated rosette formation in a dose-dependent and satiable manner for *P. falciparum* and *P. vivax* isolates, reaching a plateau at 100 ng/ml (FIGS. 4A and B). For *P. falciparum*, no significant difference in rosette-stimulatory effect between the CSMT and IGFBP7 was found (FIG. 4C). On the contrary, *P. vivax* rosette-stimulation by CSMT was significantly higher than that by recombinant IGFBP7 alone (FIG. 4D). The rosette-stimulating capacity of IGFBP7 was abolished by heat denaturation at 95° C. for one hour (FIGS. 4E and F), thus eliminating the possibility that the effect was due to a non-protein contaminant in the recombinant protein preparation. Furthermore, the IGFBP7 binding-inducing effect was only observed when URBC and IRBC were present in the culture. Incubation of URBC alone with IGFBP7 did not induce clustering effect on the cells (FIG. 10, top panel). IGFBP7 required a minimum of 15 minutes to significantly stimulate rosetting. However, the rosette-stimulating effect did not significantly increase further afterwards (FIG. 4G). Importantly, IGFBP7-mediated rosetting was a reversible event, where removal of the protein from the system reverted the rosetting rates to their baseline values (rosetting rates recorded prior to IGFBP7 exposure) as fast as 15 minutes post-protein removal (FIG. 4H).

Figure 5A:
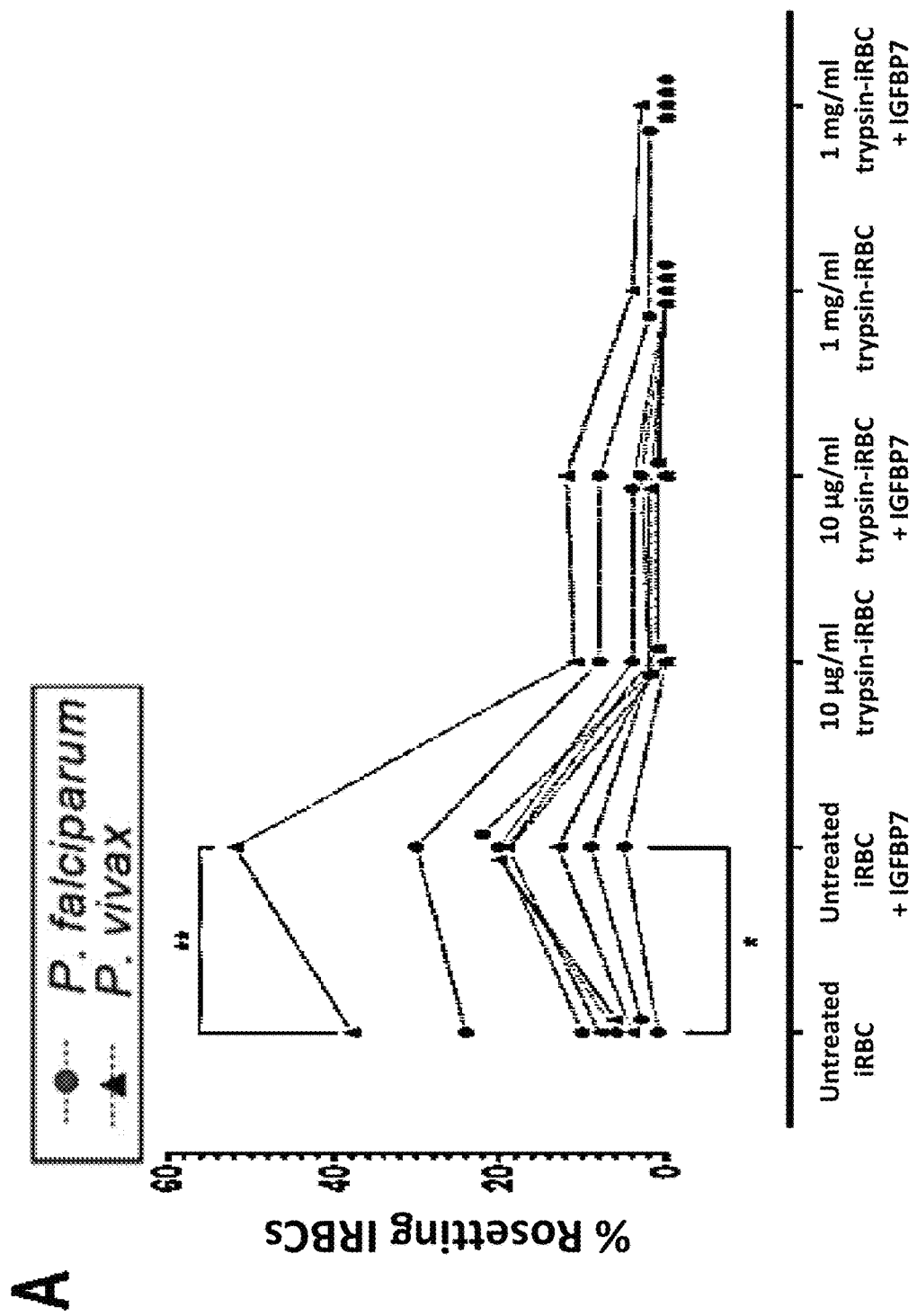
Figure 5B:
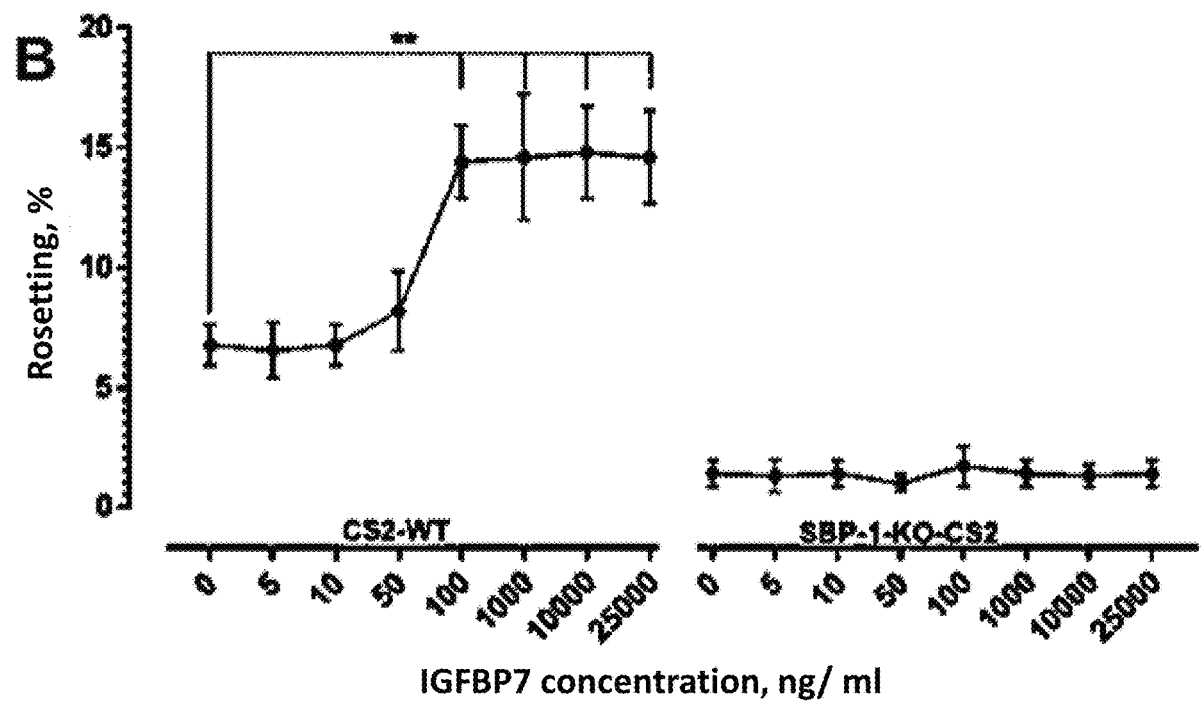
Figure 5C:
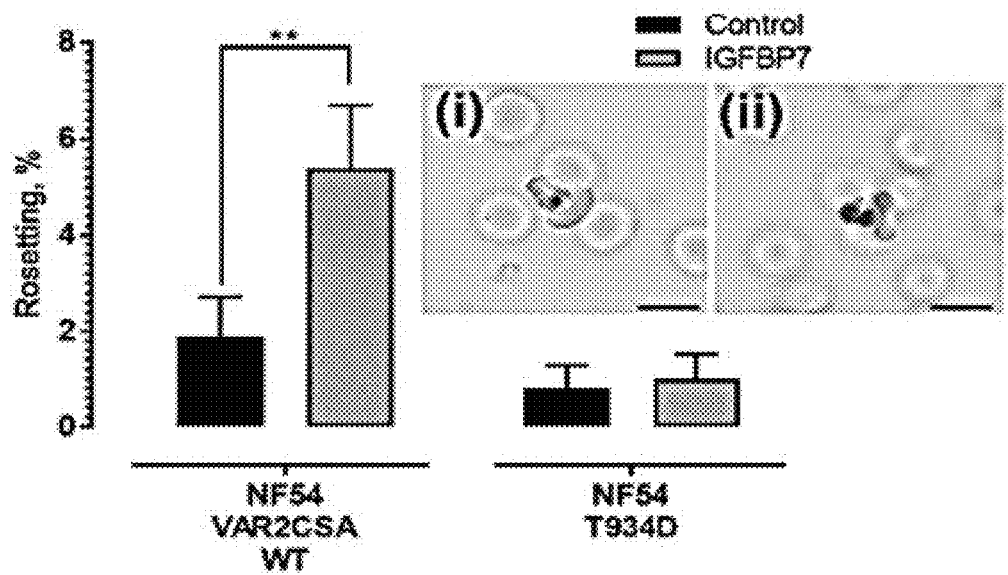
Figure 5D:
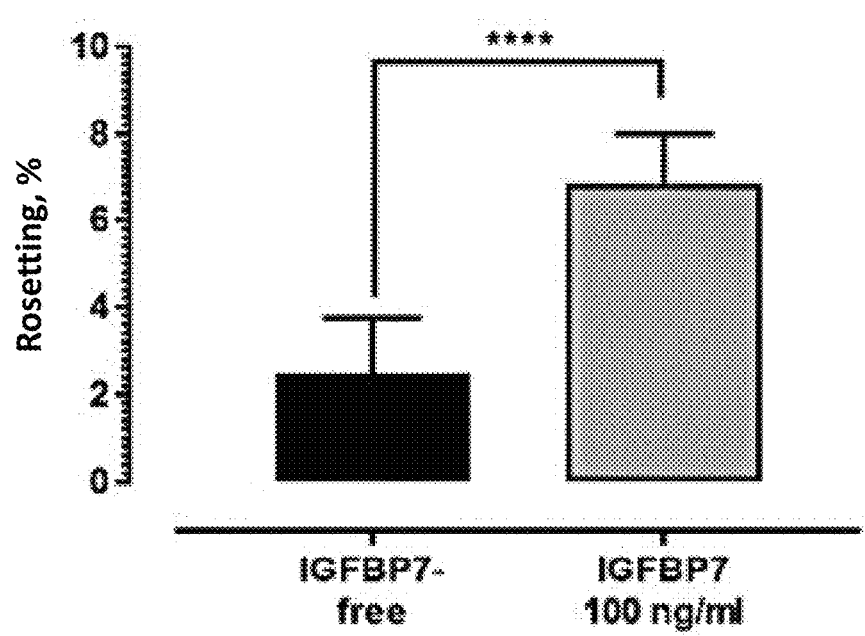

5. Parasite-Derived Rosetting Ligands Essential to IGFBP7-Mediated Rosetting Trypsinisation of IRBC abrogated the rosette-stimulating effect of IGFBP7 (FIG. 5A), suggesting the involvement of parasite-derived proteins expressed on the surface of IRBC. *P. falciparum* expressed different surface antigens including rosetting ligands such as the *P. falciparum* erythrocyte membrane proteins 1 (PfEMP1), STEVOR and RIFIN27. The sensitivity to low level of trypsin treatment (10 μg/ml) used here suggested that PfEMP1, instead of STEVOR or RIFIN was likely the adhesin involved28,29. We further validated this hypothesis by using the *P. falciparum* SBP1-KO-CS2 line, in which the skeleton binding protein 1 (SBP1) gene has been knocked out. SBP1 transports PfEMP1 from the parasitophorous vacuole to the Maurer's cleft for subsequent assembly and export to the surface of IRBC. Therefore, the SBP1-KO-CS2 line is unable to express PfEMP1 on the surface of the IRBC. However, knock out of this gene does not affect the surface expression of STEVOR and RIFIN30,31. IGFBP7 increased rosetting rate of CS2 wild-type parasite but had no effect on SBP1-KO-CS2 rosetting (FIG. 5B). Subsequently, we used two other clones of the *P. falciparum* NF54 line, NF54_VAR2CSA_WT clone and the mutant clone, NF54_T934D, whose PfEMP1 variant VAR2CSA is not exported onto the surface of the IRBCs 32. The rosetting machinery of NF54_VAR2CSA_WT responded positively to the presence of IGFBP7. On the other hand, the rosetting rates of NF54_T934D clone (lacking PfEMP1 on the surface of IRBC) were not significantly altered by IGFBP7 (FIG. 5C and see Table 8). Of note, IRBCs with surface expression of PfEMP1 variant VAR2CSA (which include the CS2_WT and NF54_VAR2CSA_WT) did not form many rosettes, which was in parallel with earlier report33. In addition, the rosettes formed by NF54_VAR2CSA_WT (FIG. 5C, inset i) and NF54_T934D (FIG. 5C, inset ii) were small.

TABLE 8

Raw data (rosetting rates, %) for the data set presented in bar graph (5C). R = biological replicate (same parasite line, but different flasks of cultures using the same URBCs and culture media).

| | *P. falciparum* lines | | | |
|---|---|---|---|---|
| | NF54 VAR2CSA_WT | | NF54 T934D | |
| R | Control | IGFBP7 | Control | IGFBP7 |
| 1 | 1.5 | 6.5 | 1.0 | 1.5 |
| 2 | 1.0 | 5.0 | 1.5 | 0.5 |
| 3 | 3.0 | 7.0 | 0.5 | 0.5 |
| 4 | 2.5 | 4.5 | 0.5 | 1.5 |
| 5 | 1.5 | 4.0 | 0.5 | 1.0 |

Figure 5E:
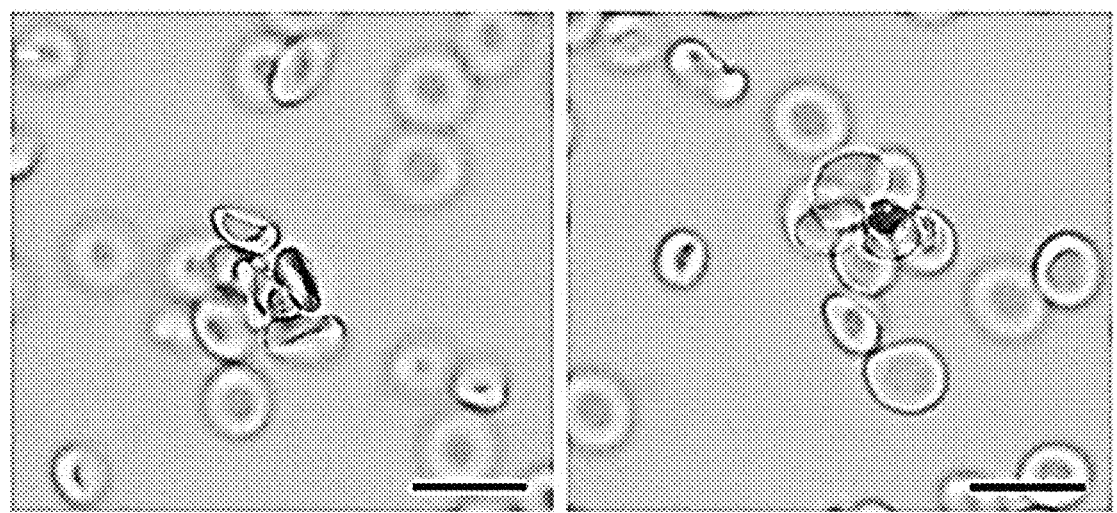

The expression of the parasite-derived, IRBC-surface proteins such as rosetting ligands are sequential and parasite stage-specific. For example, PfEMP1 is the first rosetting ligand to be expressed on the surface of IRBC (as early as late ring stage), followed by RIFIN, and finally STEVOR (which are at the much more mature stages) 34-38. In other words, PfEMP1 is the only rosetting ligand available on the surface of late ring-IRBCs. We performed the IGFBP7-rosetting assessment on the late ring stages (~hour 16-26) of a laboratory-adapted clinical isolate (nine replicates across three different cycles) and found that IGFBP7 significantly increased the rates of rosette formation (FIG. 5D and see Table 9) by the late ring stages (FIG. 5E). Taken together, these results suggest strongly that PfEMP1 is essential for IGFBP7-mediated rosetting in *P. falciparum*. On the other hand, we could not identify which *P. vivax* proteins were involved in IGFBP7-mediated rosettes since the *P. vivax*-IRBC membrane-associated proteins have yet to be fully characterized.

TABLE 9

Raw data (rosetting rates, %) for the data set presented in bar graph (5D). R = biological replicate (same lab-adapted parasite, but conducted on three cycles of ring stages from three different flasks of cultures using the same batch of URBCs and culture media). F = flask, C = cycle

| R (F/C) | IGFBP7-free | IGFBP7 100 ng/ml |
|---|---|---|
| 1/1 | 3.0 | 6.0 |
| 2/1 | 4.5 | 8.5 |
| 3/1 | 4.0 | 7.0 |
| 1/2 | 3.0 | 8.0 |
| 2/2 | 2.5 | 6.0 |
| 3/2 | 1.5 | 7.0 |
| 1/3 | 2.0 | 8.0 |
| 2/3 | 1.0 | 5.0 |
| 3/3 | 1.0 | 6.0 |

6. Host-Derived Rosetting Receptors Essential to IGFBP7-Mediated Rosetting

Figures 6A, 6B:
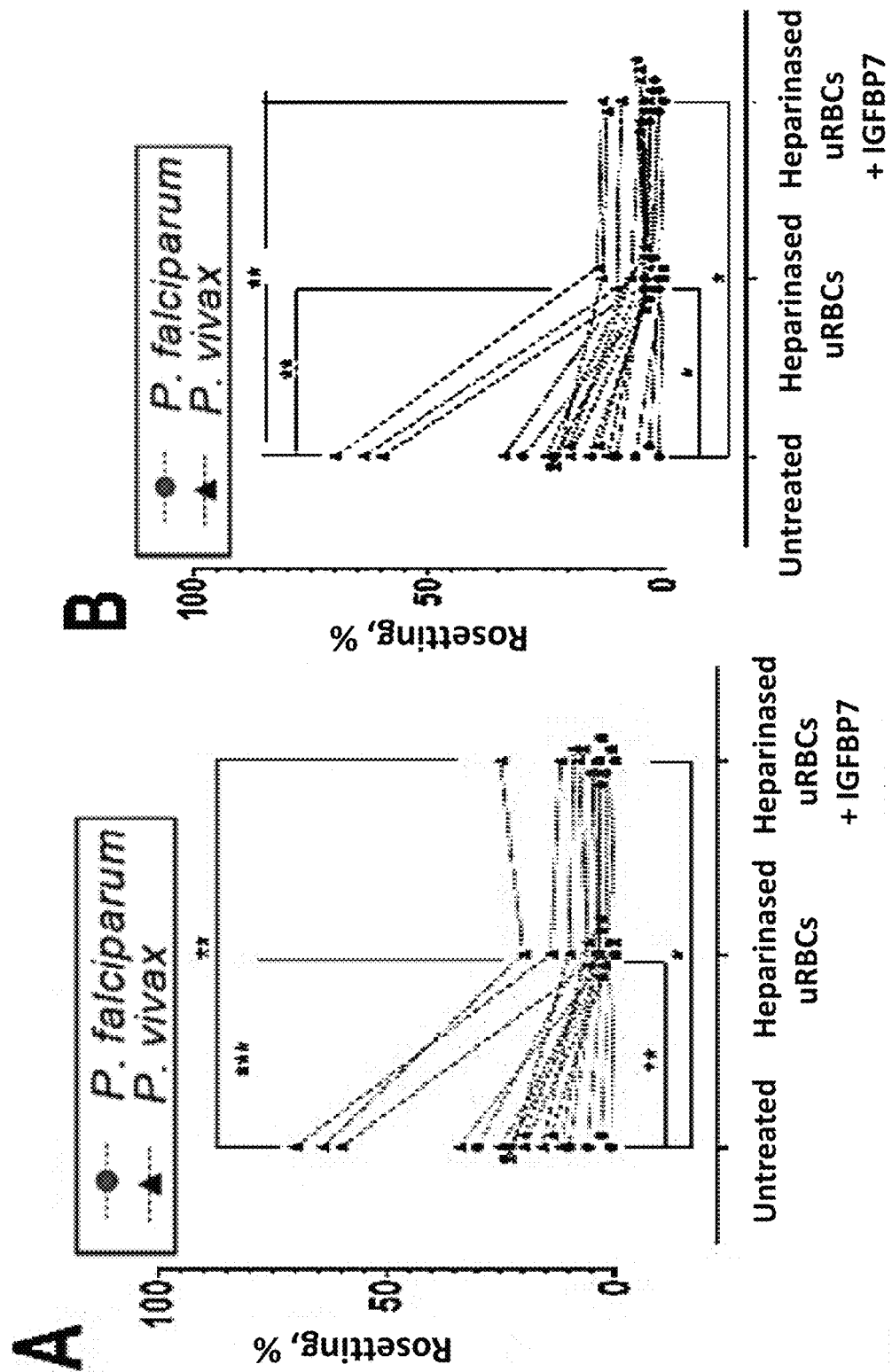
Figure 6C:
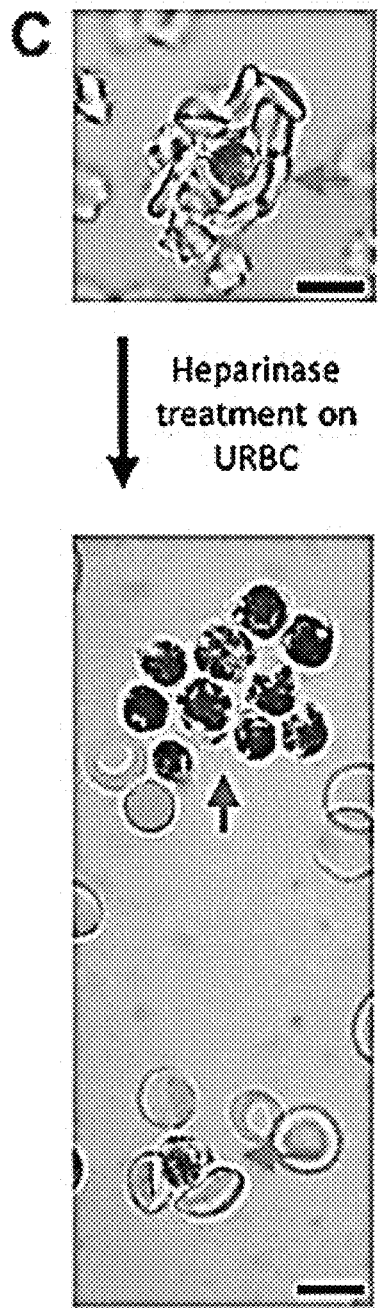

IGFBP7 has a heparin binding domain. We hypothesized that it might be involved in the rosetting effect. When URBC treated with either heparinase I (FIG. 6A) or heparinase III (FIG. 6B) were mixed with purified *P. falciparum*- or *P. vivax*-IRBC, IGFBP7 did not induce rosetting. Heparinases also affected the size of rosettes (numbers of URBC in a rosette) (FIG. 6C, green arrows). Notably, addition of IGFBP7 induced autoagglutination-like clustering of IRBC (which were not enzyme-treated) (FIG. 6C, red arrow). IRBC-autoagglutination was absent in the control groups (untreated and enzyme-treated groups without addition of IGFBP7) (data not shown).

Figure 6D:
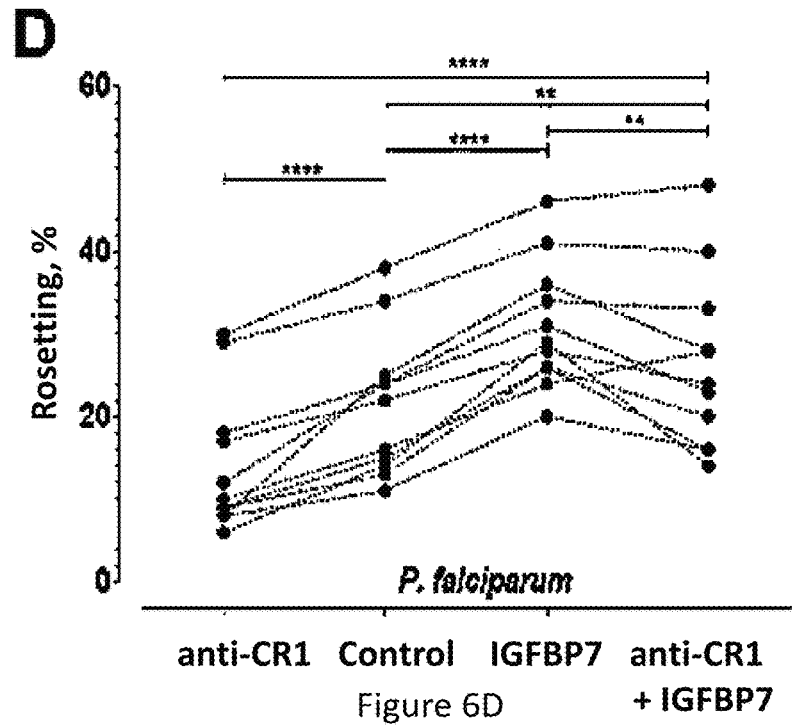
Figure 6E:
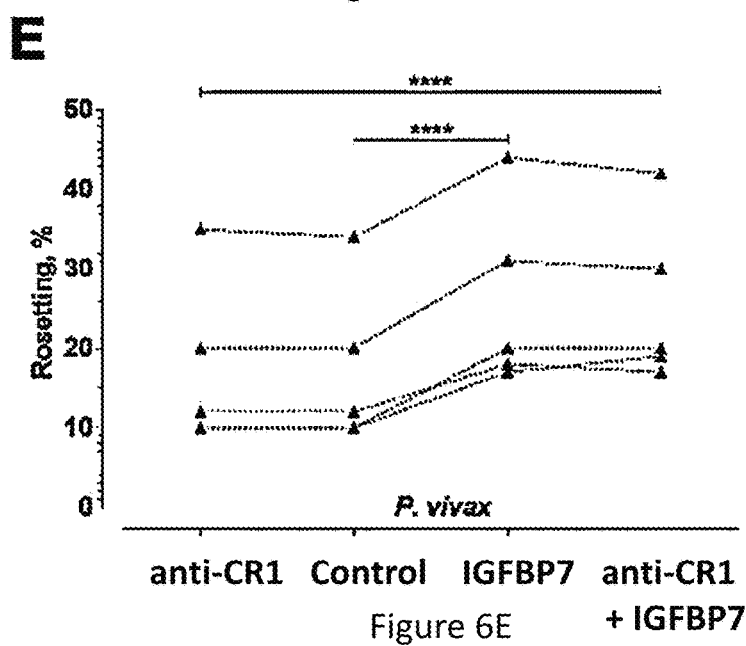
Figure 6F:
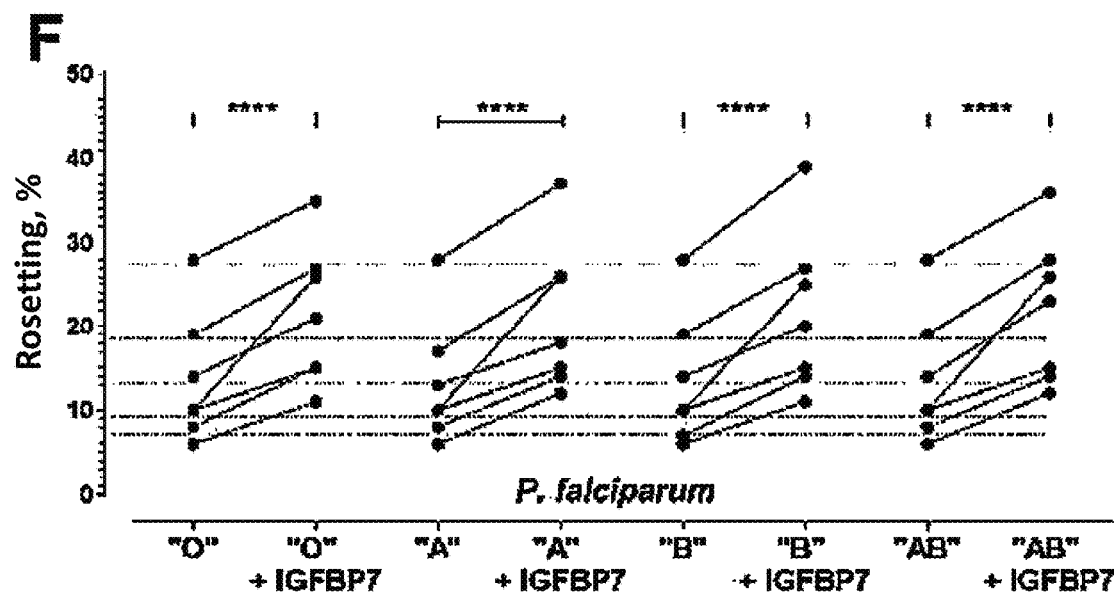
Figure 6G:
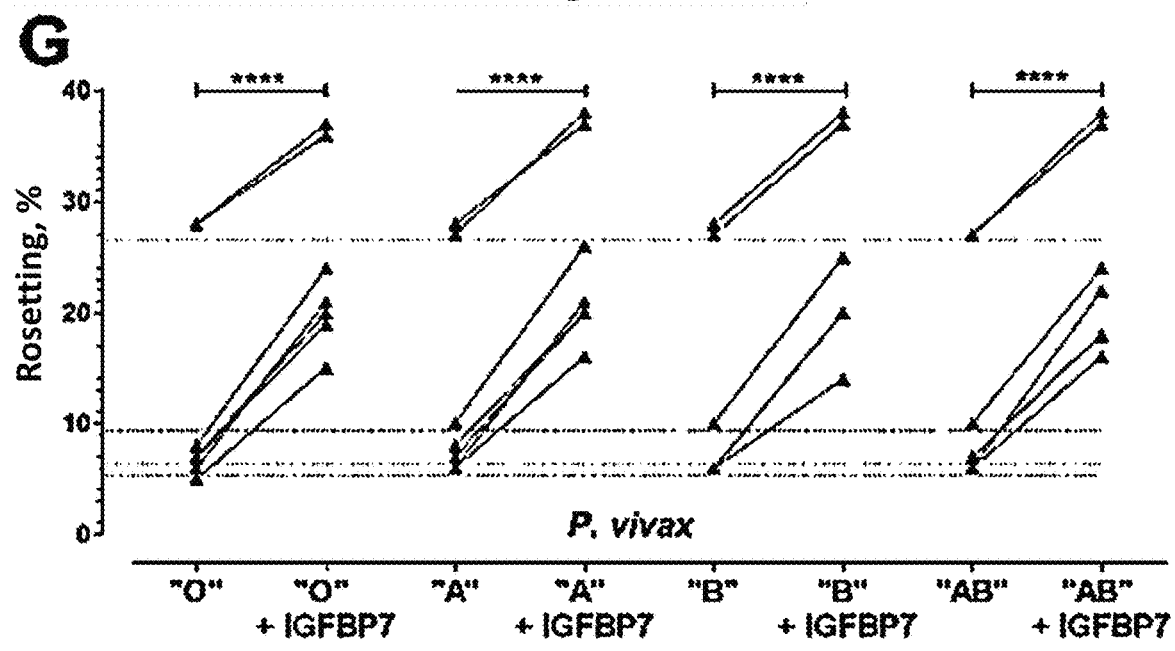
Figure 6H:
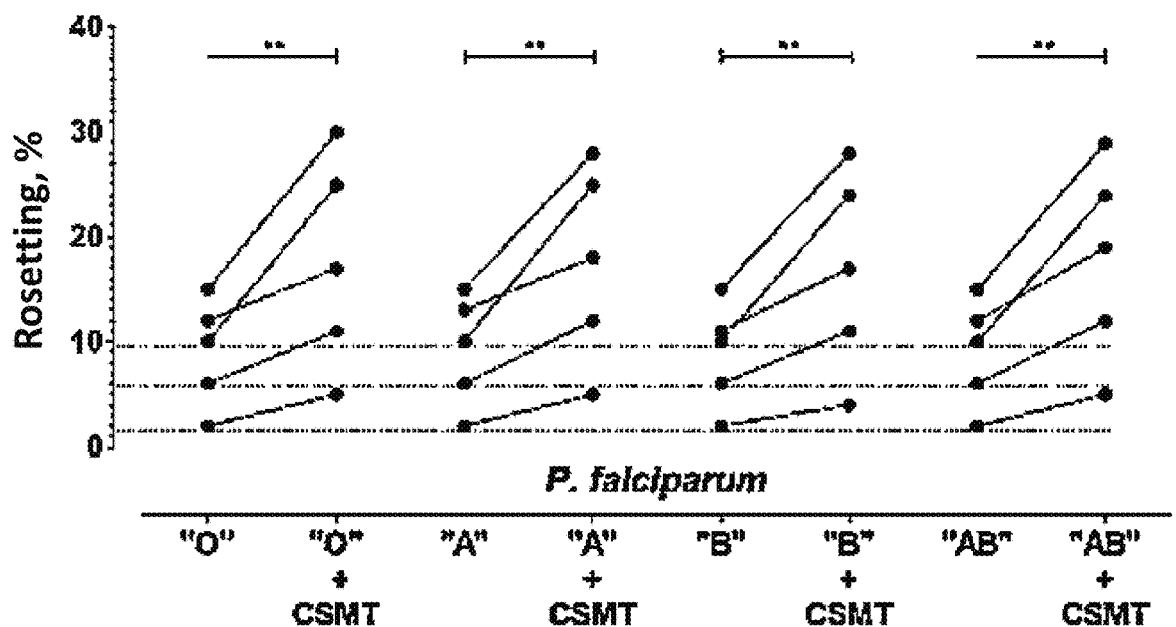
Figure 6I:
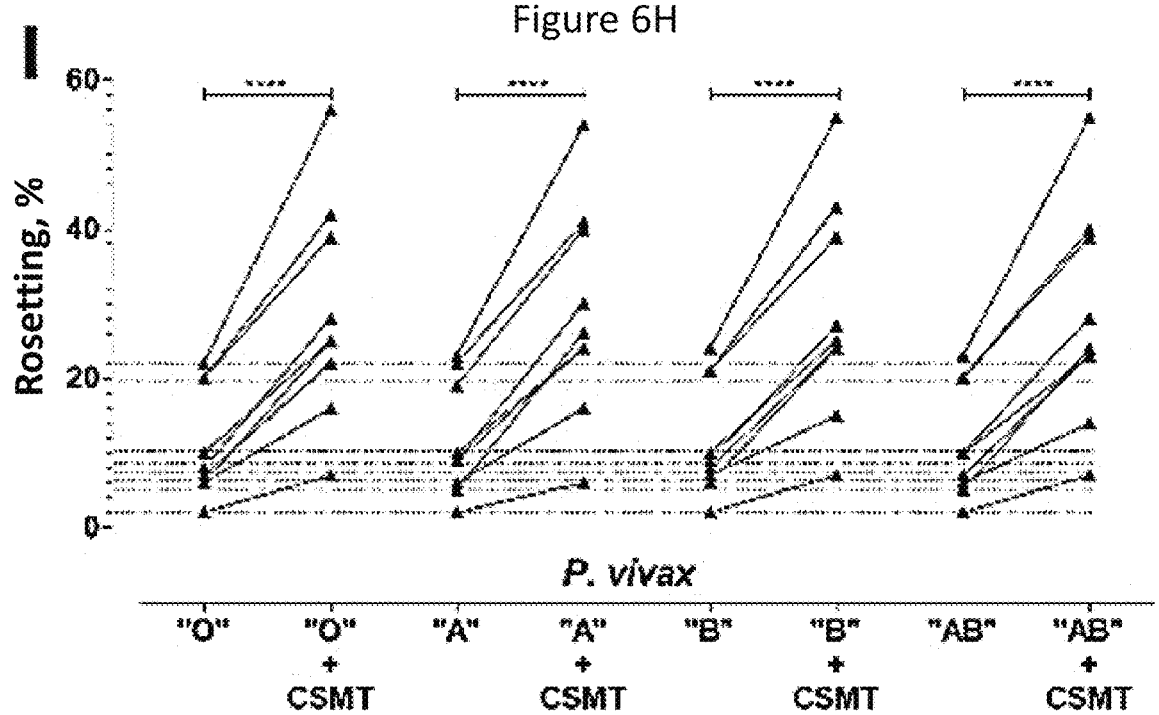

Complement receptor 1 (CR1) expressed on URBC is a receptor for PfEMP1 in *P. falciparum* rosetting39. However, it did not play a significant role in IGFBP7-mediated rosetting for both parasite species. Anti-CR1 mAb reduced *P. falciparum* rosetting rates in the absence of IGFBP7, confirming that this molecule is involved in the direct interaction between IRBC and URBC (FIG. 6D). However, anti-CR1 mAb had insignificant effect on IGFBP7-induced rosetting in *P. falciparum* (FIG. 6D). For *P. vivax*, anti-CR1 antibody did not inhibit rosetting, with or without addition of IGFBP7 to the culture (FIG. 6E). Likewise, For *P. falciparum* and *P. vivax* (FIGS. 6F and G), ABO blood groups did not play significant roles in IGFBP7-mediated rosetting, as well as rosetting mediated by other CSMT-derived rosette-stimulators (FIGS. 6H and I).

7. Serum-Derived Co-Factors in IGFBP7-Mediated Rosetting

All the experiments described above were performed using 20% human serum-enriched medium. However, serum filtration with a 0.45 μm filter abolished IGFBP7-induced rosetting (FIG. 7A). These results indicated that other large-sized serum-derived protein aggregates or multimers might be needed for the IGFBP7-mediated rosetting effect. We hypothesised that Von Willebrand factor (VWF) may be involved since VWF has been reported to absorb onto plasma-exposed surfaces. Addition of anti-VWF antibody (25 μg/ml) did not significantly alter the baseline rosetting rates (FIG. 7B). However, the presence of anti-VWF antibody prevented IGFBP7 from exerting its rosette-stimulatory effect. The specificity of rosette-inhibition by the antibodies was validated with experiments using antibody isotype controls at the same working concentration (25 µg/ml) (FIG. 11).

Figure 7C:
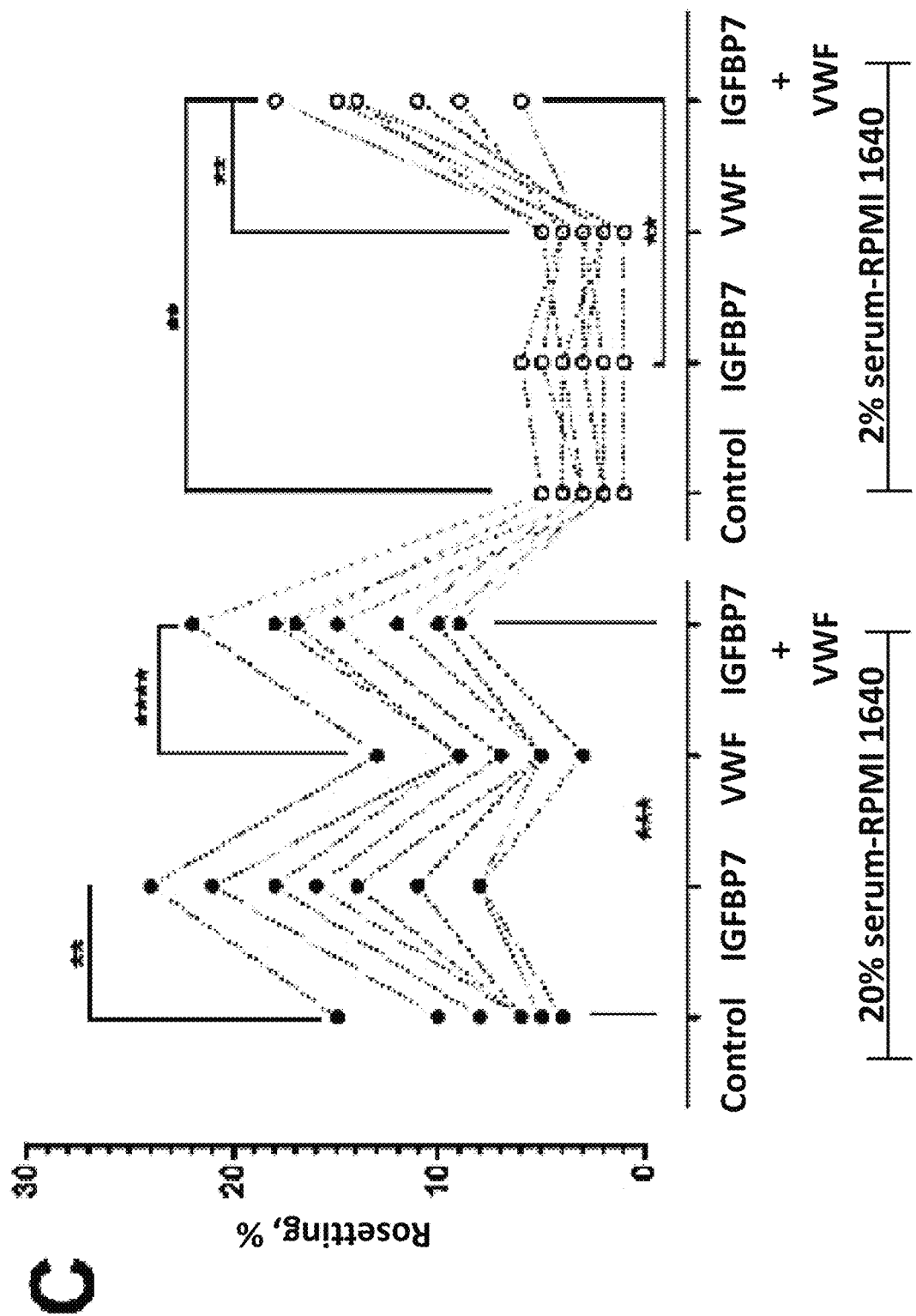
Figure 7D:
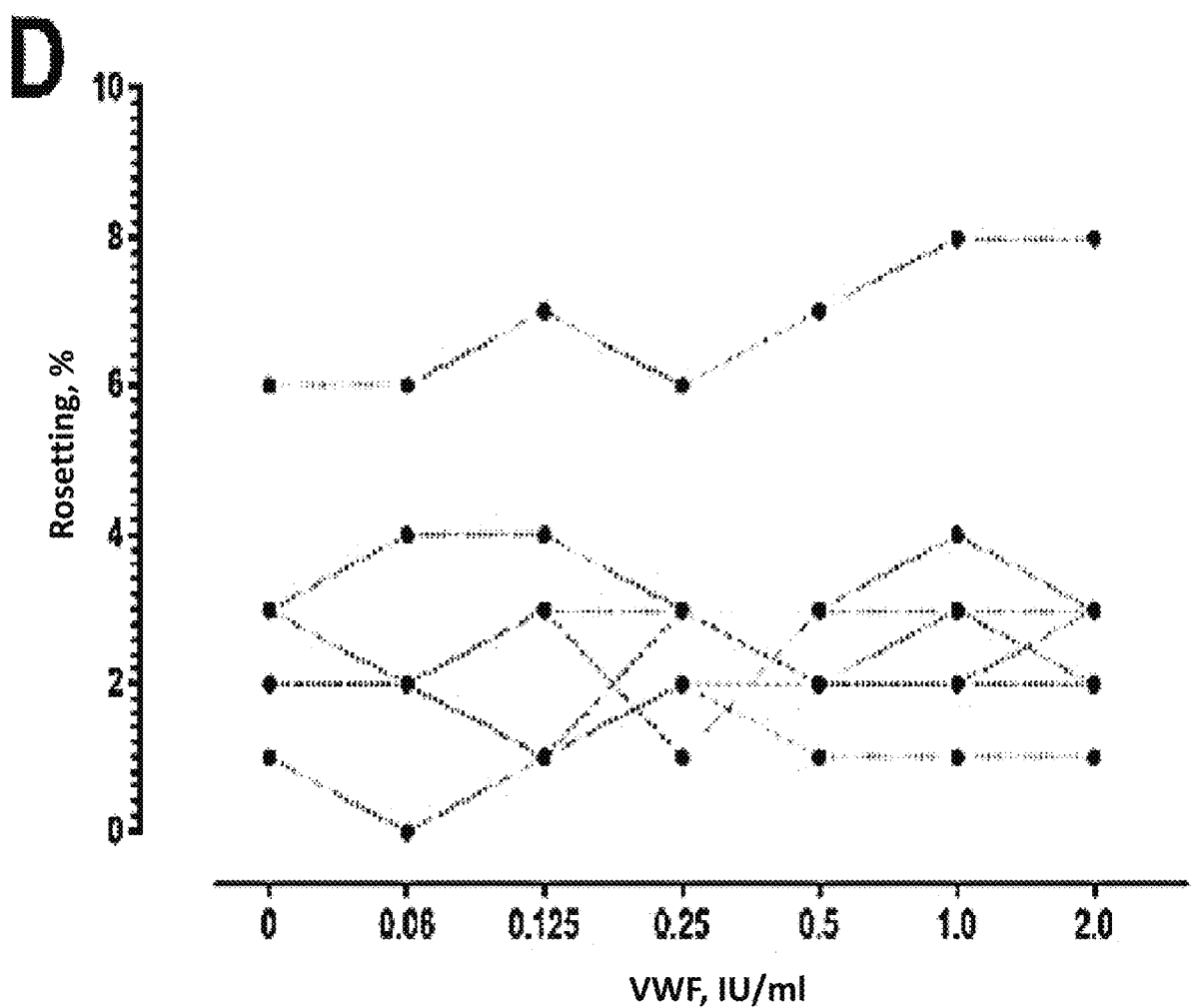

When we reduced the medium's serum enrichment to only 2%, IGFBP7 could not increase rosetting rates (FIG. 7C). The protein could only exert its rosette-stimulatory effect in 2% serum-enriched medium when VWF was added. Importantly, VWF by itself did not stimulate rosetting (FIG. 7C), disputing the possibility of this phenomenon as a non-specific adhesive effect of VWF and indicating that it is a co-factor of the IGFBP7-mediated rosetting. When the media's serum enrichment was replaced with Albumax II (a serum substitute), addition of IGFBP7 (100 ng/ml) and VWF did not significantly increase rosetting rates across the VWF concentration range tested (FIG. 7D). This suggested the need of other serum-derived factors mediating the IGFBP7 rosetting effect. We suspected that this second cofactor should either be needed in small quantity or present in high abundance in serum that even a 2% serum-supplied medium is adequate to sustain IGFBP7-mediated rosetting. In addition, this co-factor should be able to interact with some of the players identified above (PfEMP1, HS, VWF) to generate IGFBP7-mediated rosettes. One candidate was thrombospondin 1 (TSP-1) since it is known to bind to PfEMP142,43 and VWF44.

Figure 7E:
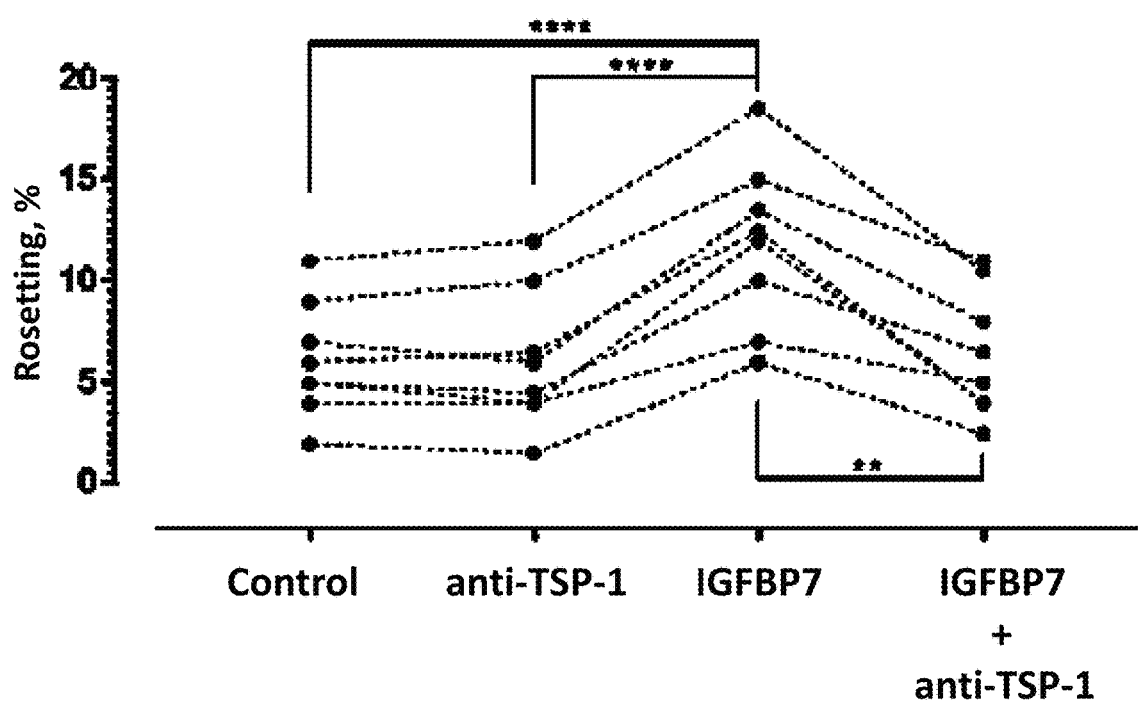

In serum-enriched medium, anti-TSP-1 antibody did not significantly alter baseline rosetting rates. Nevertheless, this antibody significantly blocked the IGFBP7-mediated rosette-stimulation (FIG. 7E). The specificity of rosette-inhibition by this antibody was validated with experiments using antibody isotype control (FIG. 11).

Figure 7F:
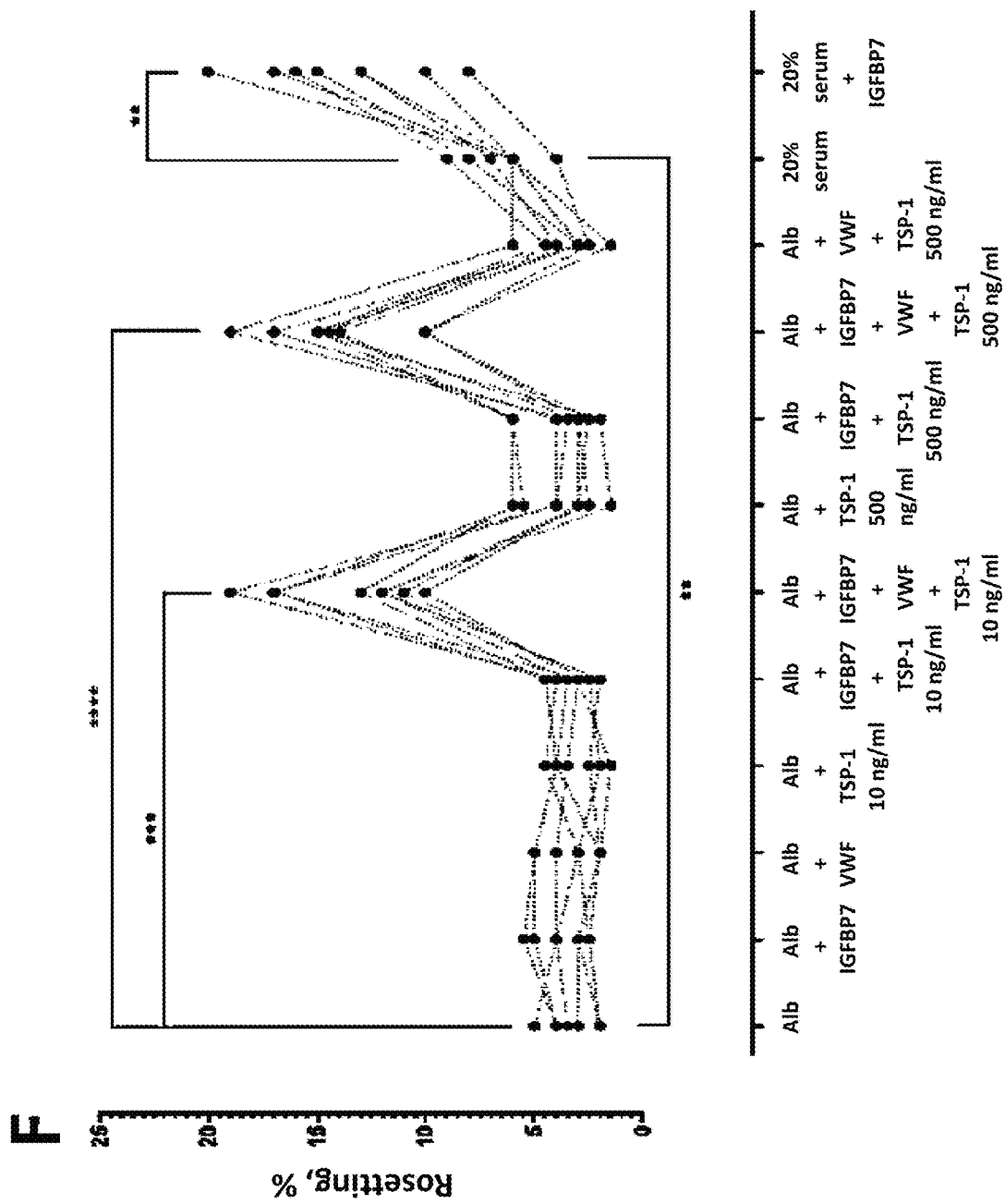
Figure 7G:
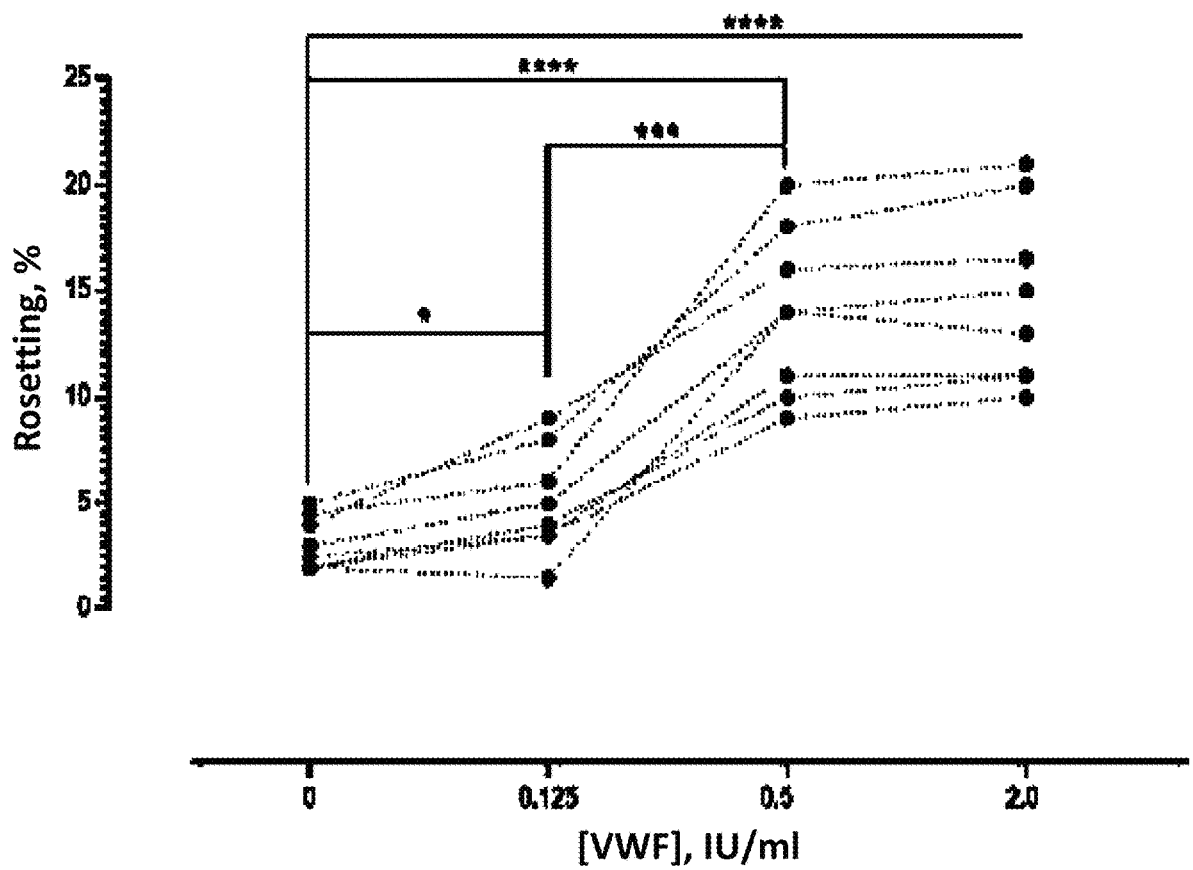

When TSP-1 was added to Albumax-supplemented medium, the rosetting rates were lower than those in serum-enriched medium (FIG. 7F). However, when added together (IGFBP7+VWF+TSP-1) to the Albumax-supplemented medium, significant rosette-stimulation was observed. A high-level TSP-1 (500 ng/ml) did not induce significantly higher rosetting stimulation than the lower level TSP-1 (10 ng/ml). With the addition of VWF (2 IU/ml) and TSP-1 (10 ng/ml) into Albumax-supplemented medium, IGFBP7 stimulated rosette formation to an extent similar to that of serum-enriched medium. Importantly, without IGFBP7, the presence of TSP-1 and VWF in Albumax-supplemented medium could not increase the rosetting rates, disputing the possibility of this event as a non-specific adhesive effect and reflecting their status as co-factors in IGFBP7-mediated rosetting. Lastly, we quantitated VWF needed to facilitate IGFBP7-mediated rosetting. When provided with IGFBP7 and TSP-1 in Albumax-supplemented medium, VWF as low as 0.125 IU/ml was sufficient to significantly increase rosetting rates, with an optimal increment attained at 0.5 IU/ml (FIG. 7G).

8. Quantification of IGFBP7 Secretion

Figures 8A, 8B:
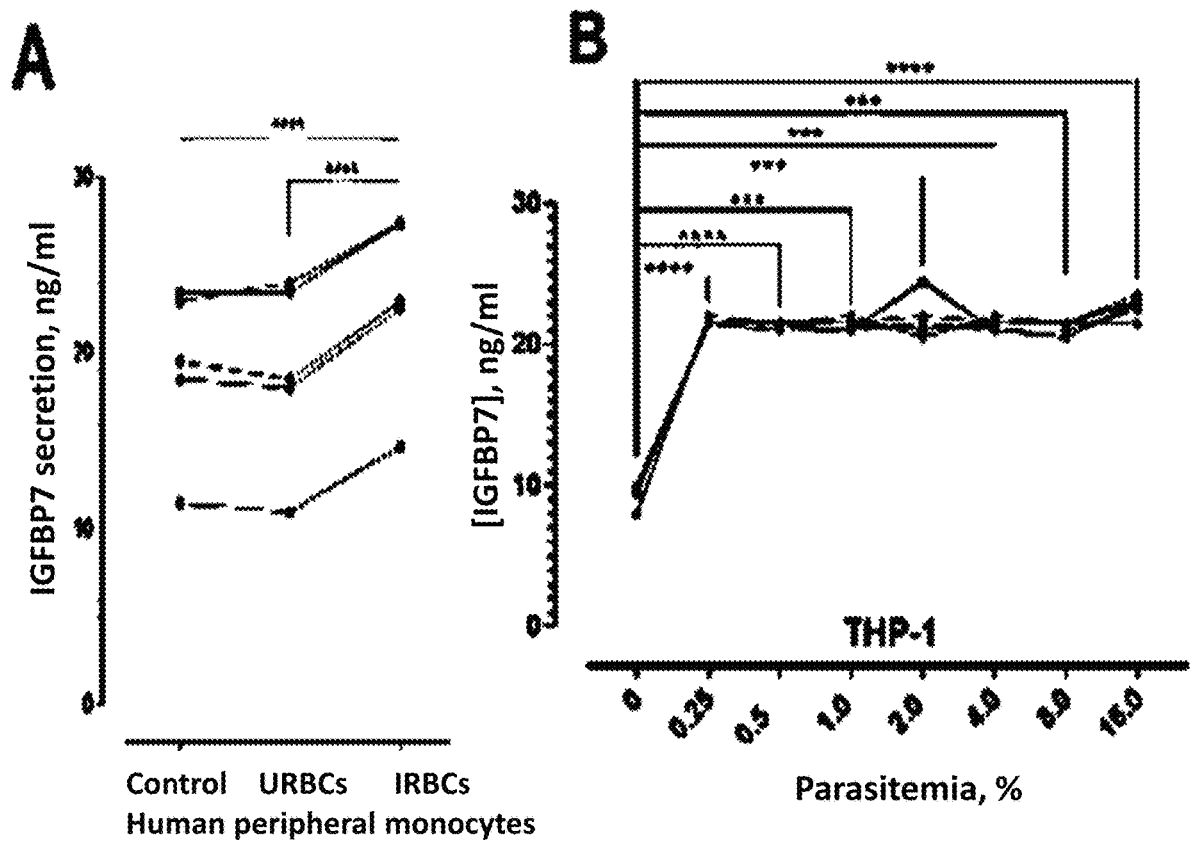

*P. falciparum* IRBC-exposed peripheral monocytes secreted significantly more IGFBP7 than their unexposed counterparts or those exposed to URBC (FIG. 8A). THP-1 also secreted more IGFBP7 after IRBC exposure (FIG. 8B). Interestingly, parasitemia as low as 0.25% was sufficient to significantly stimulate THP-1 to secrete more IGFBP7. Further increase in parasite density (up to 16% parasitemia) did not significantly increase IGFBP7 secretion any further.

9. Knockdown of IGFBP7 Expression by THP-1 Using RNAi Transduction

Figure 8C:
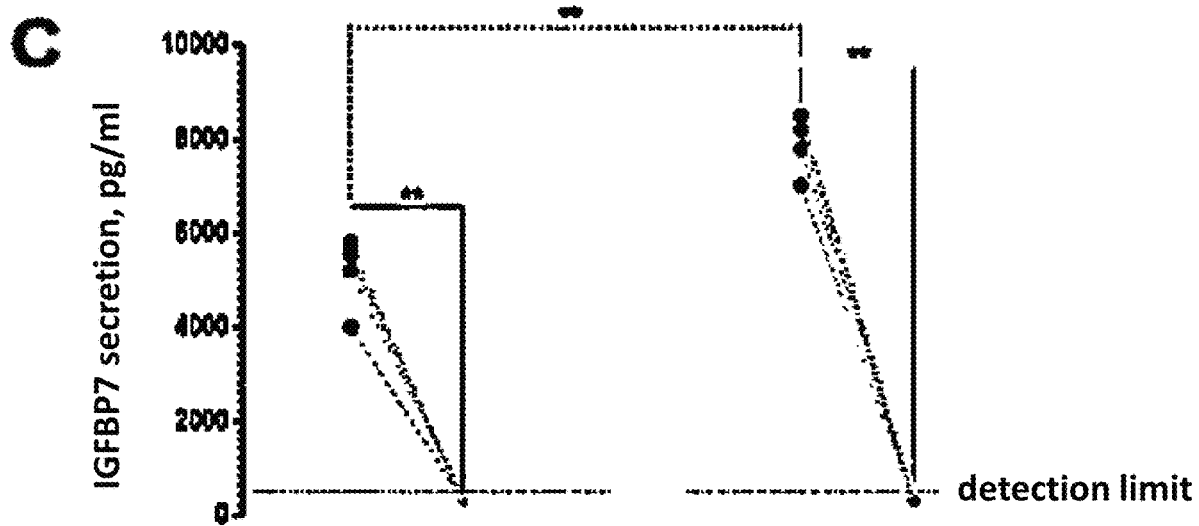
Figure 8D:
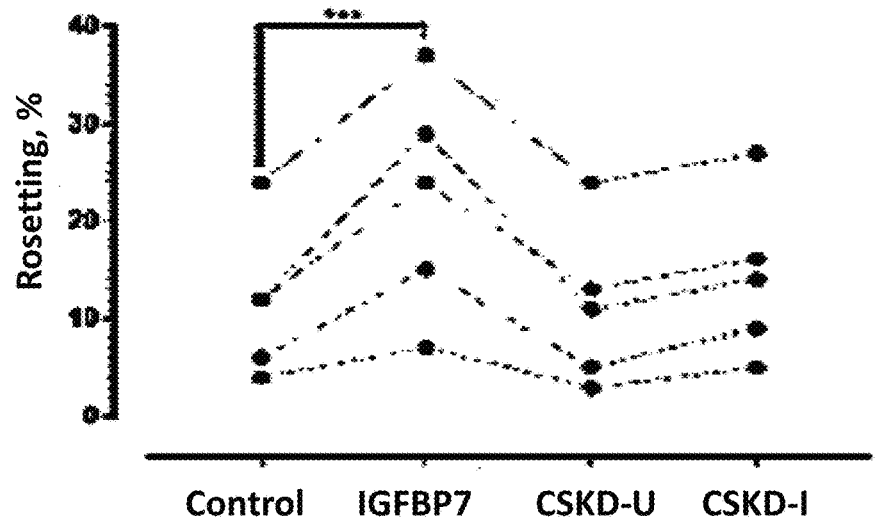

THP-1 with reduced expression (knock down) of IGFBP7 (referred to as IGFBP7-KD-THP-1) after ShRNA transduction were generated. IGFBP7 production was barely detected in IGFBP7-KD-THP-1 after URBC or IRBC stimulation (FIG. 8C). The URBC- and IRBC-conditioned supernatants from IGFBP7-KD THP-1 (hence referred to as CSKD-U and CSKD-I respectively) were collected for rosetting assay. CSKD-U and CSKD-I did not significantly increase rosetting rates of the *P. falciparum* parasites (FIG. 8D), indicating that IGFBP7 is the main rosette-stimulating factor in IRBC-stimulated THP-1 cells.

10. Phagocytosis Assessment

Figure 8E:
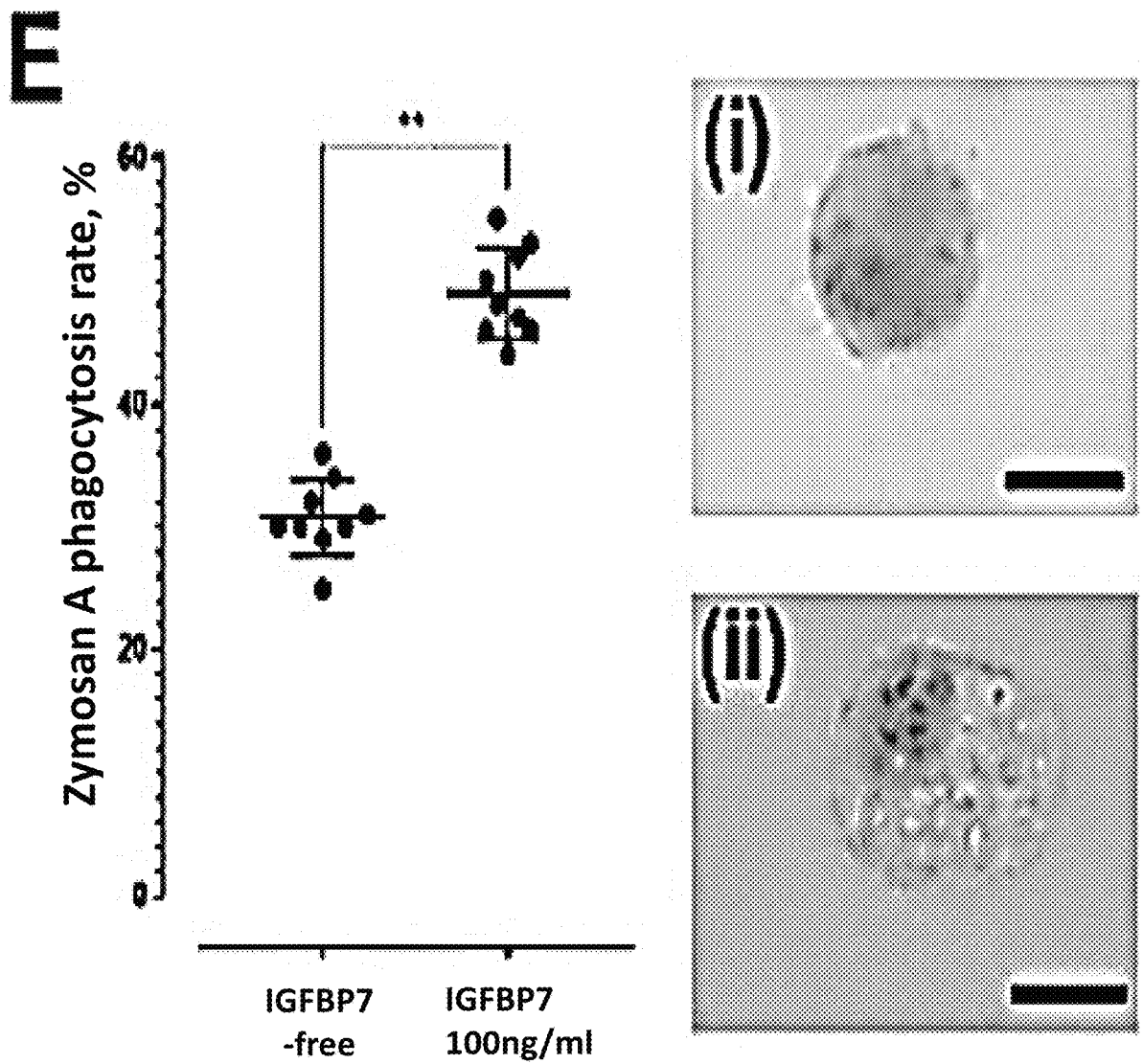
Figure 8F:
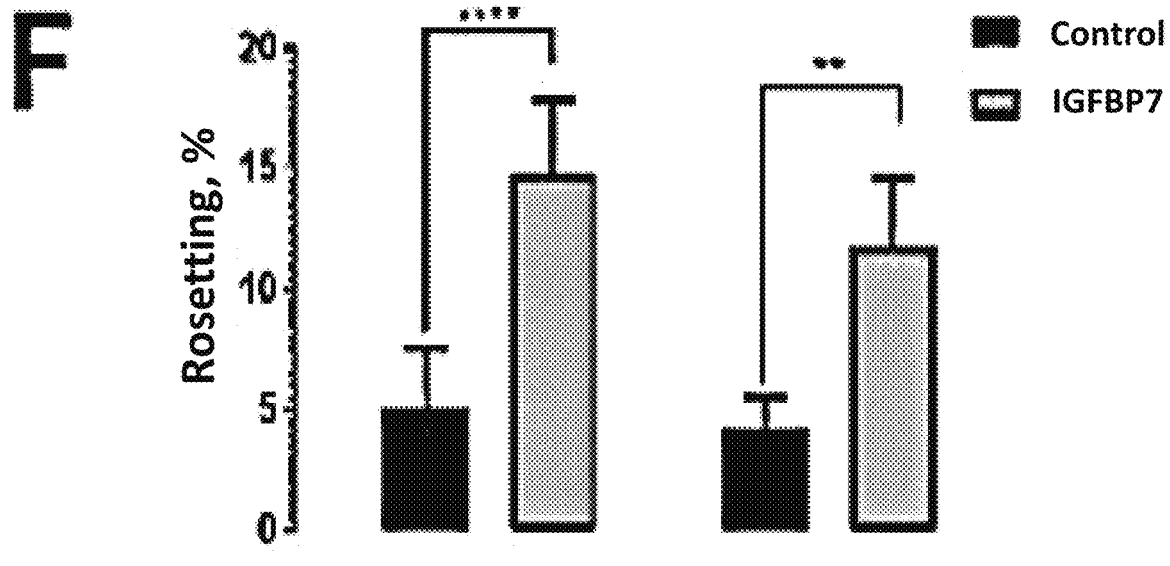
Figure 8G:
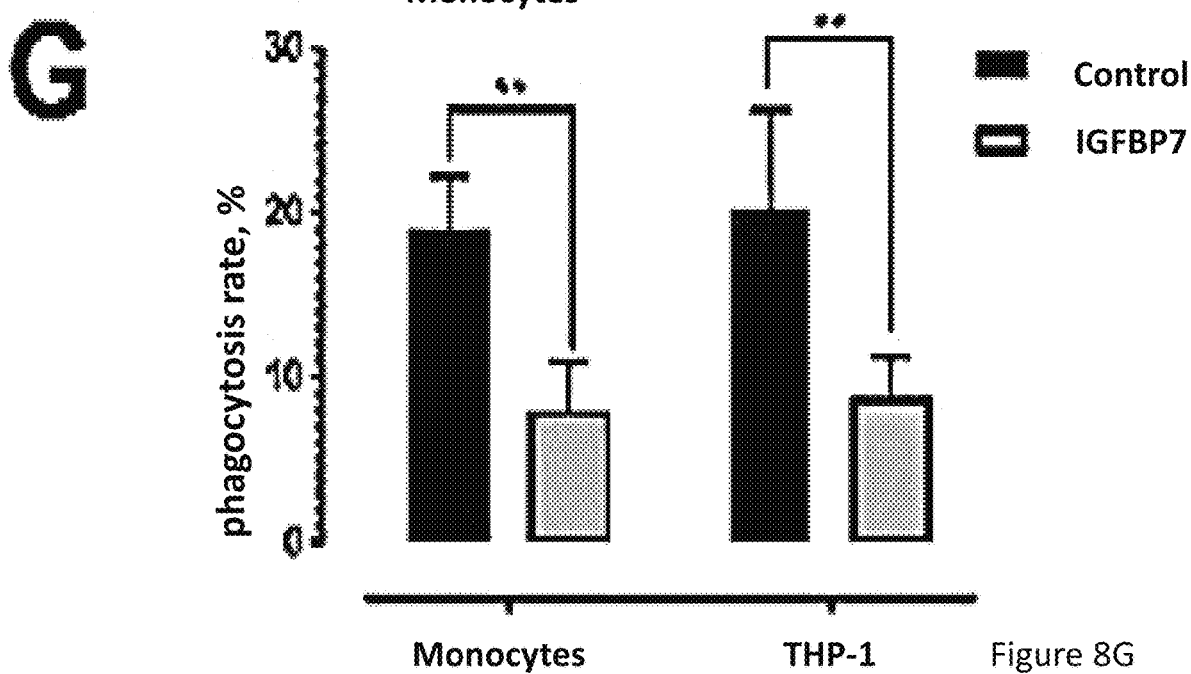
Figure 8H:
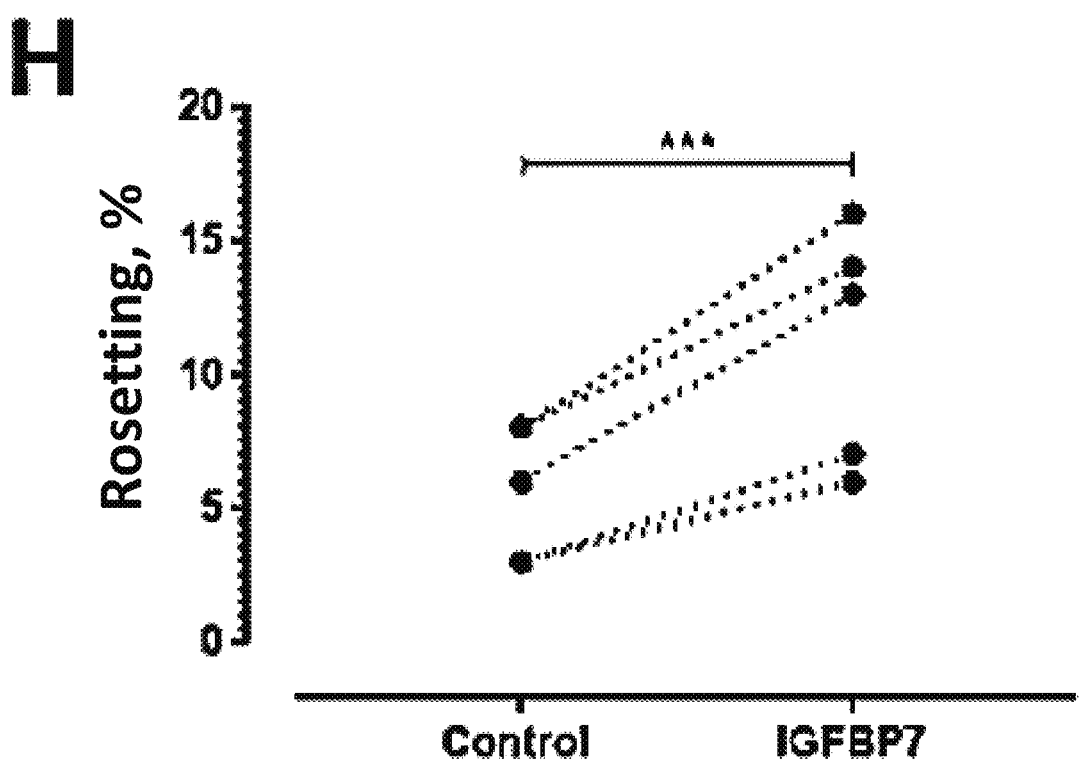
Figure 8I:
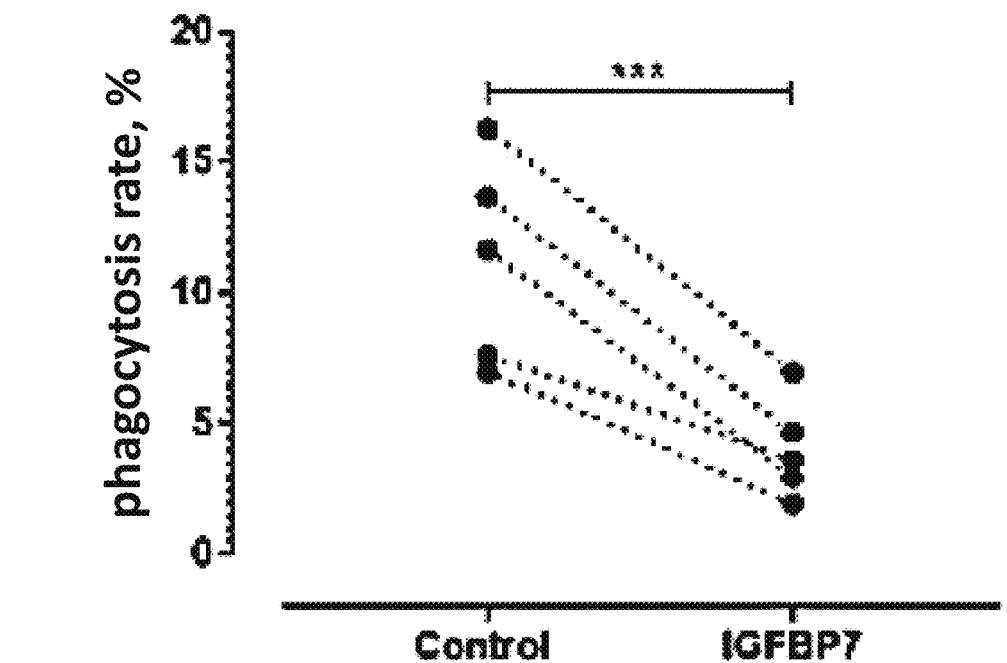
Figure 8J:
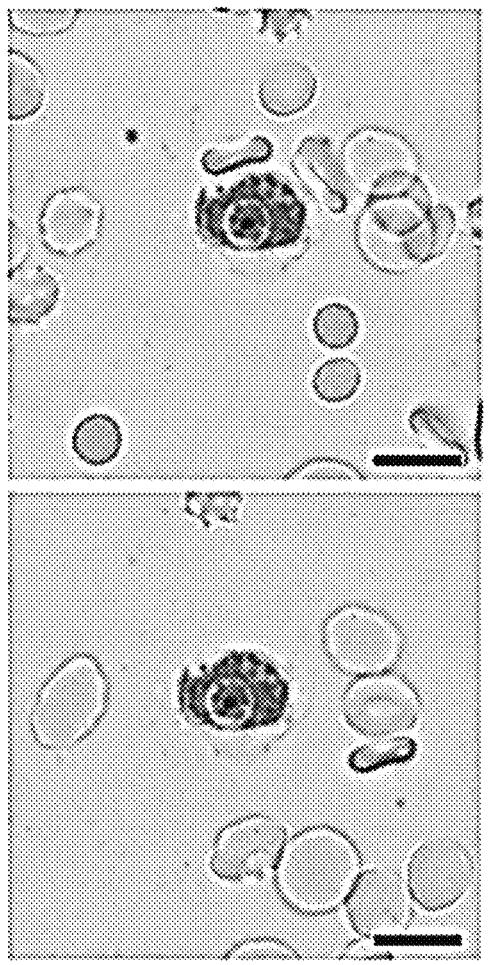
Figure 8K:
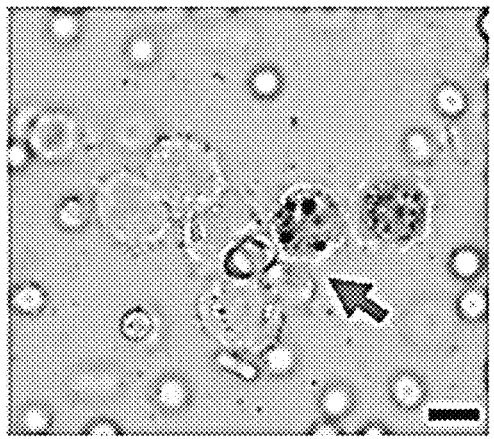
Figure 8L:
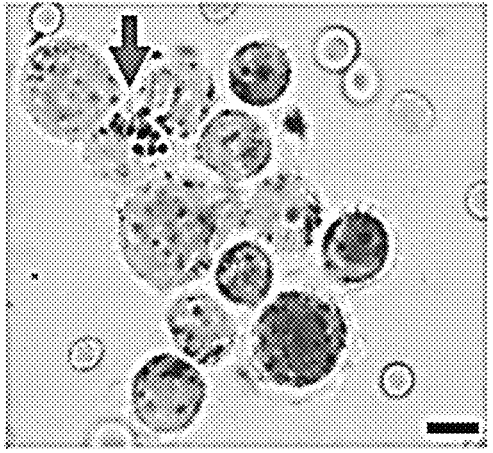

We hypothesized that IGFBP7-mediated rosetting could be a strategy used by the parasites to avoid phagocytosis. To test this, we performed a control experiment using Zymosan A (a protein-carbohydrate complex prepared from yeast cell wall, commonly used in phagocytosis assays) and showed that IGFBP7 by itself did not inhibit the phagocytosis ability of THP-1 (FIG. 8E). Unexpectedly, incubation with IGFBP7 increased the phagocytosis ability of THP-1. We next tested the phagocytic activity of THP-1 and of human primary monocytes in presence of IGFBP7-treated culture. As expected, the rosetting rates of the parasite increased after IGFBP7 exposure. (FIG. 8F and see Table 10). However, IRBC phagocytosis rates by both types of phagocytes were reduced significantly (FIG. 8G and see Table 11). Subsequently, we repeated this experiment with THP-1 using five different *P. falciparum* lines. All IGFBP7-incubated *P. falciparum* lines prior to THP-1 exposure formed more rosettes (FIG. 8H). They were significantly less phagocytosed than their non-IGFBP7-exposed counterparts (FIG. 8I). Individual phagocytes could engulf non-rosetting IRBC (8J). However, successful engulfment of a rosette was only observed when several phagocytes were recruited (FIGS. 8K and L).

TABLE 10

Raw data (rosetting rates, %) for the data set presented in bar graph (8F). R = biological replicate (same parasite, but different batches of cultures grown with different batches of URBCs).

| R | Monocytes IGFBP7-free | Monocytes IGFBP7 100 ng/ml | THP-1 IGFBP7-free | THP-1 IGFBP7 100 ng/ml |
|---|---|---|---|---|
| 1 | 2.0 | 10.0 | 4.0 | 10.0 |
| 2 | 5.0 | 14.0 | 6.0 | 11.0 |
| 3 | 7.0 | 18.0 | 5.0 | 13.0 |
| 4 | 8.0 | 15.0 | 3.0 | 16.0 |
| 5 | 4.0 | 17.0 | 4.0 | 9.0 |

TABLE 11

Raw data (phagocytosis rates, %) for the data set presented in bar graph (8G). R = biological replicate (same parasite, but different batches of cultures grown with different batches of URBCs).

| R | Monocytes IGFBP7-free | Monocytes IGFBP7 100 ng/ml | THP-1 IGFBP7-free | THP-1 IGFBP7 100 ng/ml |
|---|---|---|---|---|
| 1 | 20.0 | 4.0 | 30.0 | 8.0 |
| 2 | 16.0 | 6.0 | 18.0 | 10.0 |
| 3 | 17.0 | 10.0 | 14.0 | 10.0 |
| 4 | 24.0 | 9.0 | 19.0 | 5.0 |
| 5 | 19.0 | 11.0 | 21.0 | 11.0 |

Discussion

Rosetting is a common characteristic of late stage-IRBC in human malaria parasites, occurring frequently in *P. falciparum* and *P. vivax*9. It has been proposed to provide a survival advantage for the parasites11. Earlier studies have shown that rosetting occurs between the direct interactions of the parasite-derived ligands on the IRBC (i.e. PfEMP1, RIFIN and STEVOR proteins for P. falciparum) with various receptors on the URBC9,29,39,45-48.

Here we demonstrated the existence of a different type of rosetting, which we have called "type II rosetting" and it does not result from the direct interaction of IRBC with URBC. It was observed in all the P. falciparum and P. vivax isolates tested. This type II rosetting differs from the classical type I rosetting since it requires bridging by soluble mediators: IGFBP7, VWF and TSP-1 between a rosetting ligand on IRBC and HS expressed by URBC. The fast rosette-stimulating effect by the protein and its fast reversion after the protein removal from the culture suggest that IGFBP7 does not mediate rosetting via irreversible binding to neither the rosetting receptor nor ligand. Instead, it is more likely to be mediated by weaker forces. It also suggests that these soluble mediators need to be present at a minimum concentration for the rosettes to occur.

We have shown that PfEMP1 is likely the principal P. falciparum rosetting ligand in this IGFBP7-mediated type II rosetting via usage of trypsin treatments, genetically modified P. falciparum clones that cannot surface-express PfEMP1, and the late ring stages of P. falciparum, the stage of maturation that manages to surface-express only one rosetting ligand, PfEMP1. However, we cannot fully dismiss the involvement of other rosetting ligands such as STEVOR or RIFIN since these proteins are encoded by multigene families and there is a lack of tools to assess and evaluate the implication of these proteins thoroughly. To our surprise, P. vivax IRBC also interacted with IGFBP7 similarly. There are no PfEMP1 orthologues in P. vivax. Based on the rosetting trend of P. vivax post-trypsin treatments, we postulate that P. vivax has multiple rosetting ligands with different trypsin sensitivities, and the one required by IGFBP7 is highly sensitive to trypsin. IGFBP7 requires the HS moieties on URBC to exert its rosette-stimulatory effect. Interestingly, removal of HS from the surface of URBC by heparinase caused the clumping of untreated IRBC (which harboured both rosetting ligands and receptors) when supplied with IGFBP7. Importantly, without enzymatic interference, the presence of this protein does not induce non-specific binding of URBC to each other, or autoagglutination-like clumping of IRBC. We hypothesized that the IGFBP7-mediated binding occurs preferably between the URBC and IRBC under normal circumstances possibly due to electrostatic differences between the URBC and IRBC49.

IGFBP7 requires other serum factors, namely VWF and TSP-1 to exert its rosette-stimulating effect. For healthy individuals, the VWF levels in the serum range from 0.48 to 1.24 IU/ml (median 0.84 IU/ml), whereas individual having underlying pathological conditions have much higher levels of serum VWF50,51. Serum TSP-1 levels in healthy individuals vary greatly (0-12060 ng/ml)52,53. We found that under serum-free conditions (Albumax-supplemented medium), concentrations of VWF as low as 0.5 IU/ml and of TSP-1 at 10 ng/ml were enough to optimally facilitate IGFBP7-mediated rosette-stimulation at IGFBP7 of 100 ng/ml (the minimum concentration needed to stimulate type II rosetting). The rosette-stimulation by the presence of these three proteins were comparable to those of 20% serum-enriched medium supplied with IGFBP7, reinforcing that IGFBP7 is the limiting factor for the rosette-stimulation.

Based on the data presented here, we proposed the following mechanism of interactions for type II rosetting (FIG. 9). IGFBP7 binds to HS on URBC. The interaction between IGFBP7 and cell surface HS has been demonstrated and well-characterized54. IGFBP7 has also been shown to bind to the D4-CK region of VWF55-57. Although heparin is found to be interacting with the A1 region of VWF57, it is likely that HS does not interact directly with VWF58 since we did not observed any rosetting when VWF was added alone in the absence of IGFBP7. Therefore, the HS on URBC interacts with IGFBP7, which also interacts with VWF. In turn, VWF interacts with PfEMP1 on IRBC via TSP-142,57. While the extracellular domain of PfEMP1 that binds to TSP-1 has yet to be identified, it should be noted that TSP1 has been commonly associated with PfEMP142, 59. The pervasive role of TSP-1 may explain why a wide range of clinical isolates and laboratory-adapted parasite lines were capable of responding positively to IGFBP7 addition.

Induction of type II rosetting in P. falciparum and P. vivax is not attributed solely to IGFBP7. Previously, it has been shown that CFD in the serum can stimulate rosetting60. This molecule was also identified in our proteomic study. Experiments with anti-CFD antibodies showed that CFD could also induce type II rosetting but to a lesser extent. The knock down of IGFBP7 expression in THP-1 demonstrated that IGFBP7 is a major monocyte-derived rosette-stimulating factor. Culture supernatant from IGFBP7-KD-THP-1 collected after 18 hours of parasite exposure could not induce rosette-stimulation. Other rosette-stimulating factors may be secreted by the cells much later. Interestingly, IGFBP7 and VWF are components in Weibel-Palade bodies, the storage granules of endothelial cells55. Future work should characterize the effect of IRBC on the secretion of IGFBP7 by endothelial cells. Of note, the reported physiologic and pathological serum concentrations of IGFBP7 vary greatly, where most of the reported normal serum IGFBP7 concentrations fall below 50 ng/ml, and the serum IGFBP7 level in different pathological conditions (e.g. various vascular disorders and cancers) are higher (as high as ~1000 ng/ml)61-65. Therefore, the working concentration of IGFBP7 in this study (100 ng/ml) is still within the pathophysiologic range in clinical settings. It would be interesting to compare the serum/plasma IGFBP7 levels of uncomplicated and severe malaria patients from the same area to understand better the role of IGFBP7 in malaria pathogenesis.

The importance of monocytes/macrophages in eliminating Plasmodium during its course of infection has been reported66,67. Peripheral monocytes68,69, as well as the tissue-resident macrophages70,71, have been shown to engulf IRBC readily. To survive, parasites must counter or avoid this host's immune responses. The ability to perceive phagocyte's secreted IGFBP7 as 'approaching threats' signal and to respond by rosetting may provide survival advantage to the parasites.

In conclusion, the host-derived IGFBP7 is used as an "incoming phagocyte signal" by the IRBC, and the IRBC in turn use this protein, along with two serum factors, VWF and TSP-1, to stimulate rosette formation, which acts as an immune-evasion strategy by hampering phagocytosis of the IRBC. It is hoped that future clinical studies will investigate associations between IGFBP7 and malaria pathogenesis and immunity.

Whilst there has been described in the foregoing description preferred embodiments of the present invention, it will be understood by those skilled in the technology concerned that many variations or modifications in details of design or construction may be made without departing from the present invention.

The invention claimed is:

1. A composition comprising (i) insulin growth factor binding protein 7 (IGFBP7) and (ii) a Von Willebrand Factor (VWF), and/or a thrombospondin-1 (TSP-1), and/or one or more other anti-malarial drugs.

2. The composition according to claim 1, wherein the amount of VWF present in the composition is between 0.125 and 0.5 IU/ml.

3. The composition according to claim 1, wherein the amount of the TSP-1 present in the composition is about 10 ng/ml.

4. The composition according to claim 1, wherein the amount of IGFBP7 present in the composition is at least 100 ng/ml.

5. The composition according to claim 1, wherein the anti-malarial drugs are selected from artemisinin and its derivatives, artesunate and its derivatives, chloroquine, mefloquine pyrimethamine, sulfadoxine, amodiaquine, quinine, quinidine, halofantrine, atovaquone, proguanil, and doxycycline.

6. A method of treating an individual afflicted with malaria comprising administering to the individual an effective amount of insulin growth factor binding protein 7 (IGFBP7).

7. The method according to claim 6, wherein the method further comprises administering a Von Willebrand Factor (VWF) and/or a thrombospondin-1 (TSP-1).

8. The method according to claim 7, wherein the amount of VWF administered to the individual is between 0.125 and 0.5 IU/ml.

9. The method according to claim 7, wherein the amount of the TSP-1 administered to the individual is about 10 ng/ml.

10. The method according to claim 6, wherein the amount of IGFBP7 administered to the individual is at least 100 ng/ml.

11. The method according to claim 6, wherein the amount of IGFBP7 administered to the individual is effective for inhibiting infected red blood cell (IRBC)-endothelial cytoadherence.

12. The method according to claim 6, wherein the method further comprises administering to the individual one or more additional anti-malarial drugs.

13. The method according to claim 12, wherein the one or more anti-malarial drugs are selected from artemisinin and its derivatives, artesunate and its derivatives, chloroquine, mefloquine pyrimethamine, sulfadoxine, amodiaquine, quinine, quinidine, halofantrine, atovaquone, proguanil, and doxycycline.

14. A method of treating an individual afflicted with malaria comprising administering to the individual an effective amount of the composition of claim 1.

* * * * *